(12) United States Patent
Schmidt et al.

(10) Patent No.: US 8,865,880 B2
(45) Date of Patent: *Oct. 21, 2014

(54) IDENTIFICATION OF A NOVEL BHD GENE

(75) Inventors: Laura S. Schmidt, Mt. Airy, MD (US); Michelle Warren, New Market, MD (US); Jorge R. Toro, Washington, DC (US); Berton Zbar, Garrett Park, MD (US); Michael L. Nickerson, Shepherdston, WV (US); Marston W. Linehan, North Bethesda, MD (US); Maria L. Turner, Washington, DC (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 108 days.

This patent is subject to a terminal disclaimer.

(21) Appl. No.: 13/179,853

(22) Filed: Jul. 11, 2011

(65) Prior Publication Data

US 2011/0288031 A1 Nov. 24, 2011

Related U.S. Application Data

(62) Division of application No. 12/334,361, filed on Dec. 12, 2008, now Pat. No. 8,003,764, which is a division of application No. 10/514,744, filed as application No. PCT/US03/17227 on May 30, 2003, now Pat. No. 7,485,709.

(60) Provisional application No. 60/385,181, filed on May 31, 2002, provisional application No. 60/390,291, filed on Jun. 20, 2002.

(51) Int. Cl.
| | |
|---|---|
| *C07H 21/04* | (2006.01) |
| *C12Q 1/68* | (2006.01) |
| *C07K 14/47* | (2006.01) |
| *A61K 38/00* | (2006.01) |

(52) U.S. Cl.
CPC .............. *C07K 14/47* (2013.01); *C12Q 1/6876* (2013.01); *C12Q 2600/154* (2013.01); *A61K 38/00* (2013.01)
USPC ........................................ 536/23.1; 536/24.3

(58) Field of Classification Search
None
See application file for complete search history.

(56) References Cited

U.S. PATENT DOCUMENTS

| | | | | |
|---|---|---|---|---|
| 5,474,796 | A * | 12/1995 | Brennan | 427/2.13 |
| 6,653,084 | B1 | 11/2003 | King et al. | |
| 7,060,802 | B1 | 6/2006 | Trakht et al. | |
| 7,485,709 | B2 | 2/2009 | Schmidt et al. | |
| 2001/0053519 | A1 * | 12/2001 | Fodor et al. | 435/6 |
| 2006/0057582 | A1 * | 3/2006 | Rosen et al. | 435/6 |

FOREIGN PATENT DOCUMENTS

| | | | | |
|---|---|---|---|---|
| WO | 2005058473 | * | 10/2000 | |
| WO | WO 02/083876 | * | 10/2002 | C12Q 1/68 |

OTHER PUBLICATIONS

Genbank Accession No. BM545992 (Feb. 20, 2002).*
NEB catalog (1998/1999), pp. 121, 284.*
Birren et al. (Genbank Accession No. AC007775, Jun. 30, 2000. ).*
Birren et al. (*Homosapiens* chromosome 17 clone RP5-962P8, Genbank Accession No. AC007775, Jun. 30, 2000).*
Bendayan, "Possibilities of False Immunocytochemical Results Generated by the Use of Monoclonal Antibodies: The Example of the Anti-proinsulin Antibody," *The Journal of Histochemistry and Cytochemistry*, 43(9): 881-886, 1995.
Birt et al., "Hereditary multiple fibrofolliculomas with trichodiscomas and acrochordons," *Arch. Dermatol.*, 113: 1674-1677, 1997 (abstract only).
Bost et al., "Antibodies Against a Peptide Sequence Within the HIV Envelope Protein Crossreacts with Human Interleukin-2," *Immunological Investigations*, 17(6&7): 577-586, 1988.
GenBank Accession No. BC025820.1: *Mus musculus*, similar to Unknown (protein for MGC:23445) (*H. sapiens*), clone MGC:37841 (gi:19387934), Sep. 20, 2002.
Hornstein et al., "Perifollicular fibromatosis cutis with polyps of the colon—a cutaneo-intestinal syndrome sui generis," *Arch. Derm. Res.*, 253: 161-175, 1975 (abstract only).
Hornstein, "Generalized dermal perifollicular fibroma with polyps of the colon," *Hum. Genet.*, 33: 193-197, 1976 (abstract only).
Kingsman et al., "High-Efficiency Yeast Expression Vectors Based on the Promoter of the Phosphoglycerate Kinase Gene," *Meth Enzymol*, 185: 329-341, 1990.
Lederman et al., "A Single Amino Acid Substitution in a Common African Allele of the CD4 Molecule Ablates Binding of the Monoclonal Antibody, OKT4," *Molecular Immunology*, 28(11): 1171-1181, 1991.
Li et al., "β-Endorphin omission analogs: Dissociation of immunoreactivity from other biological activities," *Proc. Natl. Acad. Sci. USA*, 77(6): 3211-3214, 1980.
Nickerson et al., "*Homo sapiens* folliculin (BHD) mRNA, complete cds," Aug. 15, 2002, GenBank Accession No. AF517523.
Nickerson et al., "Mutations in a novel gene lead to kidney tumors, lung wall defects, and benign tumors of the hair follicle in patients with the Birt-Dubé syndrome," *Cancer Cell*, 2: 157-167, 2002.
Schmidt et al., "Birt-Hogg-Dubé syndrome, a genodermatosis associated with spontaneous pneumothorax and kidney neoplasia, maps to chromosome 17p11.2," *Am. J. Hum. Genet.*, 69:876-882, 2001.
Toro et al., "Birt-Hogg-Dubé syndrome: a novel marker of kidney neoplasia," *Arch. Dermatol.*, 135:1195-1202, 1999 (abstract only).
Zbar et al., "Risk of renal and colonic neoplasms and spontaneous pneumothorax in the Birt-Hogg-Dubé syndrome," *Cancer Epidem. Bio. Prev.*, 11:393-400, 2002.

* cited by examiner

*Primary Examiner* — Jeanine A Goldberg
(74) *Attorney, Agent, or Firm* — Klarquist Sparkman, LLP

(57) ABSTRACT

The present disclosure relates to Birt-Hogg-Dubé syndrome, nucleic acids encoding the BHD gene, and methods of using the nucleic acids and proteins encoded thereby. In particular, the present disclosure relates to methods of diagnosing BHD disease and related conditions, such as spontaneous pneumothorax and kidney cancer, and methods of treating BHD skin lesions.

11 Claims, 4 Drawing Sheets

FIG. 5A

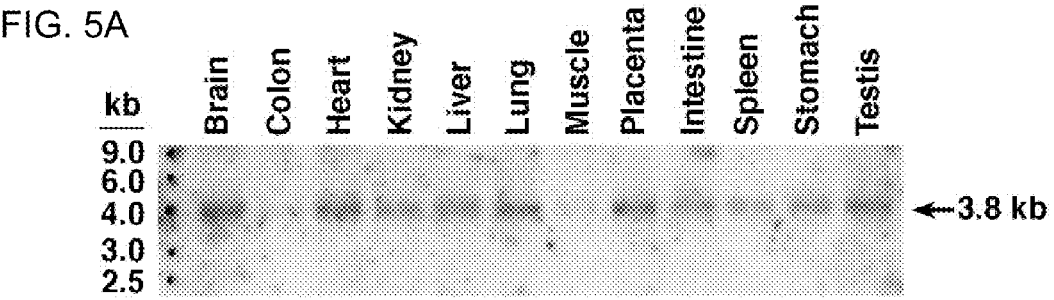

FIG. 5B

```
  1 MNAIVALCHFCELHGPRTLFCTEVLHAPLPQGDGNEDSPGQGEQAEEEEGGIQMNSRMRA
 61 HSPAEGASVESSSPGPKKSDMCEGCRSLAAGHPGYISHDKETSIKYVSHQHPSHPQLFSI
121 VRQACVRSLSCEVCPGREGPIFFGDEQHGFVFSHTFFIKDSLARGFQRWYSIITIMMDRI
181 YLINSWPFLLGKVRGIIDELQGKALKVFEAEQFGCPQRAQRMNTAFTPFLHQPNGNAARS
241 LTSLTSDDNLWACLHTSFAWLLKACGSRLTEKLLEGAPTEDTLVQMEKLADLEEESESWD
301 NSEAEEEEKAPVSPESTEGPELTQGPAESSSLSGCGSWQPRKLPVFKSLPHMRQVLGAPS
361 FRMLAWHVLMGNQVIWKSRDVDLVQSAFEVLRTMLPVGCVRIIPYSSQYEEAYRCNFLGL
421 SPHVQIPPMVLSSEFAVIVEVHAAARSTLHPVGCEDDQSLSKYEFVVTSGSPVAADRVGP
481 TILNKIEAALTMQNLSVDVVDQCLVCLKEEWMNKVKVLFKFTKVDSRPKEDTQKLLSILG
561 ASEEDNVKLLKFWMTGLSKTYKSHLMSTVRSPTASESRN.
```

FIG. 6

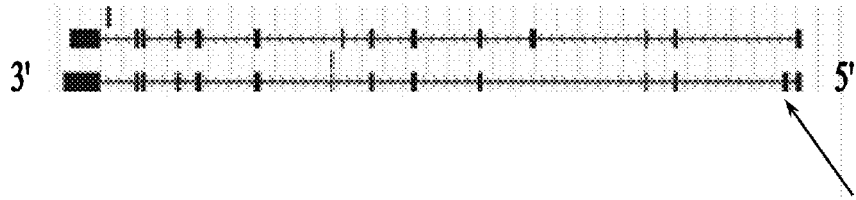

IDENTIFICATION OF A NOVEL BHD GENE

CROSS-REFERENCE TO RELATED APPLICATIONS

This is a divisional of U.S. application Ser. No. 12/334,361, filed Dec. 12, 2008 now U.S. Pat. No. 8,003,764; which is a divisional of U.S. application Ser. No. 10/514,744, filed Nov. 16, 2004, now issued as U.S. Pat. No. 7,485,709; which is the §371 U.S. National Stage of International Application No. PCT/US03/17227, filed on May 30, 2003, which was published in English under PCT Article 21(2), and which in turn claims the benefit of U.S. Provisional Application No. 60/385,181, filed May 31, 2002, and U.S. Provisional Application No. 60/390,291, filed Jun. 20, 2002. Each of these previous applications is incorporated by reference herein in its entirety.

FIELD OF THE DISCLOSURE

The present disclosure relates to Birt-Hogg-Dubé syndrome, nucleic acids encoding the BHD gene, and methods of using the nucleic acids.

BACKGROUND

The triad of dermatologic lesions, including fibrofolliculomas, trichodiscomas and achrocordons, known as the Birt-Hogg-Dubé (BHD) syndrome, was originally described in a Canadian kindred in 1977 (Birt et al., *Arch. Dermatol.* 113: 1674-1677, 1977). Other phenotypic features were found to be associated with BHD syndrome including renal neoplasia (Roth et al., *J. Amer. Acad. Derm.* 29:1055-1056, 1993) and lung cysts and/or spontaneous pneumothorax (Toro et al., *Arch Dermatol.* 135:1195-1202, 1999). When adjusted for age, patients with fibrofolliculomas (benign tumors of the hair follicle) have about a seven-fold increased risk for developing renal neoplasms and a 50-fold increased risk for developing spontaneous pneumothorax compared with their unaffected siblings. Lung cysts develop frequently (83%) in affected members of BHD families (Zbar et al., *Cancer Epidem. Bio. Prev.* 11:393-400, 2002). Although colon polyps have been reported in BHD patients (Hornstein et al., *Hum. Genet.* 33:193-197, 1976; Hornstein et al., *Arch. Derm. Res.* 253:161-175, 1975), the frequency is not statistically significant compared to unaffected siblings (Zbar et al., *Cancer Epidem. Bio. Prev.* 11:393-400, 2002). Previously, the present inventors used the original BHD family of Birt, Hogg and Dubé to perform a genome-wide scan for linkage and localized the disease gene locus by linkage analysis in 8 additional families to a 4 cM region of chromosome 17p11.2 between D17S1857 and D17S805 (Schmidt et al., *Am. J. Hum. Genet.* 69:876-882, 2001). Linkage to 17p12-q11.2 was also reported in a Swedish BHD pedigree with associated renal neoplasms (Khoo et al., *Oncogene* 20, 5239-5242, 2001). The BHD encoding sequence, however, is unknown.

SUMMARY OF THE DISCLOSURE

Disclosed herein is a BHD encoding sequence and methods of use, several specific mutant BHD encoding sequences, and the proteins (folliculins) encoded by these nucleic acid molecules. Also disclosed is a BHD consensus sequence. Specific embodiments are methods of diagnosing BHD disease and related conditions. Also provided are methods of treating BHD skin lesions.

In certain embodiments, the BHD encoding sequence is used in methods for the differential diagnosis of BHD disease, and in particular examples the BHD encoding sequence is used in a diagnostic test for BHD mutations performed using a blood sample. This test is particularly useful in detecting asymptomatic mutation carriers in BHD families.

Also disclosed are novel therapies for treatment of BHD skin lesions (fibrofolliculomas). For example, in certain embodiments the methods are methods of treating BHD skin lesions using a cream containing the BHD protein, folliculin. Such methods are expected to reduce the size and appearance of the benign hair follicle tumors. Further embodiments are methods of using the BHD encoding sequence in the differential diagnosis of sporadic kidney cancer. The BHD encoding sequence is the third gene found to be responsible for inherited kidney cancer, and mutation testing allows for diagnosis and initiation of the proper treatment, which is different for each of the types of kidney cancer caused by the three genes.

In some embodiments, the methods are methods of using the BHD encoding sequence in the differential diagnosis for spontaneous pneumothorax or collapsed lung. Collapsed lung can be caused by several factors, and a BHD diagnostic test allows a physician to determine if the emergency situation resulting from the subject's collapsed lung will recur, and whether the subject carries the predisposition to develop additional spontaneous pneumothoraces due to a BHD encoding sequence mutation.

The foregoing and other features and advantages will become more apparent from the following detailed description of a several embodiments.

BRIEF DESCRIPTION OF THE FIGURES

FIG. 2 is a physical map of the BHD critical region on 17p11.2 defined by critical recombinants in Families 243, 210 and 216 showing location of the BHD gene.

FIG. 3 is a series of pedigrees showing mutation analysis of the BHD gene and cosegregation with disease in Families 200, 202, and 230.

FIG. 4 shows the results of mutation analysis of the BHD gene and cosegregation with disease in Family 228. Sequence analysis of a subcloned PCR product from a BHD affected individual showed a 28 bp duplication (nt 1378-1405) in exon 9.

FIG. 5A. Northern blot analysis of BHD expression. A 3.8 kb transcript was detected in all tissues when a Northern blot (Origene, Rockville, Md.) with 12 major tissues was hybridized with an exon 11 amplicon of the BHD gene. The same size band was detected on a minor tissue Northern blot (Origene, Rockville, Md.), which included skin, and a fetal blot (Clontech, Mountain View, Calif.) containing lung, kidney, liver, and brain. Hybridization of the blots with an exon 4 amplicon produced the same 3.8 kb transcript. All lanes were loaded with 2 micrograms poly A+ RNA. FIG. 5B. Amino acid sequence of the BHD protein, folliculin, consisting of 579 amino acids (SEQ ID NO: 2). The locations of mutations identified in BHD patients are double-underlined. The predicted motifs in black boxes include: a conserved SLS potential phosphorylation site (aa 128-130), a glutamic acid-rich coiled-coil domain (aa 283-313), and a N-glycosylation site (aa 494-497). Three myristoylation sites are triple-underlined (aa 52-57, aa 266-271, aa 470-475). Regions of high homology in other species are underlined in black.

FIG. 6 is a schematic diagram of a putative BHD exon sequence involved in an alternatively spliced variant (SEQ ID NO: 13). This exon (indicated by the arrow) falls between the first and second exon of the wildtype human BHD cDNA, and the resultant alternative cDNA sequence does not include exon 4 of the wildtype sequence.

BRIEF DESCRIPTION OF THE SEQUENCE LISTINGS

Figure 1:
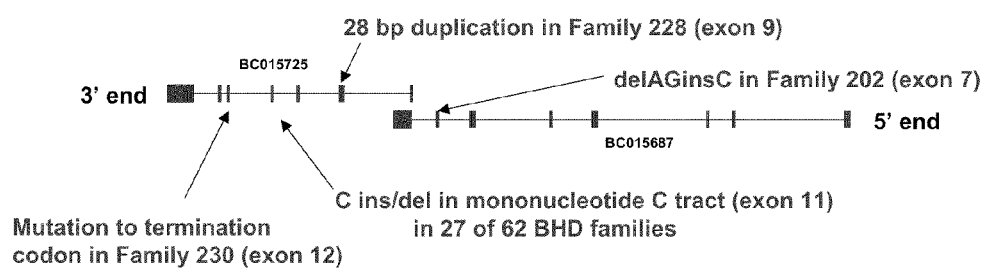
FIG. 1 is a schematic diagram summarizing some specific BHD gene mutations

The nucleic acid and protein sequences listed in the accompanying sequence listing is shown using standard letter abbreviations for nucleotide bases, and triple letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named SeqList-64802-04.txt, created on Jul. 8, 2011, 103 KB, which is incorporated by reference herein.

In the accompanying Sequence Listing:

SEQ ID NO: 1 shows the sequence of the human BHD cDNA, along with the sequence of the encoded protein.

SEQ ID NO: 2 shows the sequence the human BHD protein, folliculin.

SEQ ID NO: 3 shows the sequence of the mutant human BHD cDNA containing the 1087delAGinsC mutation, along with the sequence of the encoded protein.

SEQ ID NO: 4 shows the sequence of a mutant truncated human folliculin.

SEQ ID NO: 5 shows the sequence of the human BHD cDNA containing the 1378→1405dup mutation, along with the sequence of the encoded protein.

SEQ ID NO: 6 shows the sequence of a mutant truncated human folliculin.

SEQ ID NO: 7 shows the sequence of the human BHD cDNA containing the 1733insC mutation, along with the sequence of the encoded protein.

SEQ ID NO: 8 shows the sequence of a mutant truncated human folliculin.

SEQ ID NO: 9 shows the sequence of the human BHD cDNA containing the 1733delC mutation, along with the sequence of the encoded protein.

SEQ ID NO: 10 shows the sequence of a mutant truncated human folliculin.

SEQ ID NO: 11 shows the sequence of the human BHD cDNA containing the C1844G mutation, along with the sequence of the encoded protein.

SEQ ID NO: 12 shows the sequence of a mutant truncated human folliculin.

SEQ ID NO: 13 shows a putative BHD exon sequence involved in an alternatively spliced variant. This exon falls between the first and second exon of the wildtype human BHD cDNA, and the resultant alternative cDNA sequence does not include exon 4 of the wildtype sequence.

SEQ ID NO: 14 shows the sequence of the mouse BHD cDNA, along with the sequence of the encoded protein.

SEQ ID NO: 15 shows the sequence of the mouse BHD protein.

SEQ ID NO: 16 shows the sequence of the SKB1 forward primer.

SEQ ID NO: 17 shows the sequence of the SKB2 reverse primer.

SEQ ID NO: 18 shows the sequence of the SKB3 forward primer.

SEQ ID NO: 19 shows the sequence of the SKB4 reverse primer.

SEQ ID NO: 20 shows the sequence of the SKB5 forward primer.

SEQ ID NO: 21 shows the sequence of the SKB6 reverse primer.

SEQ ID NO: 22 shows the sequence of the SKB7 forward primer.

SEQ ID NO: 23 shows the sequence of the SKB8 reverse primer.

SEQ ID NO: 24 shows the sequence of the SKB9 forward primer.

SEQ ID NO: 25 shows the sequence of the SKB10 reverse primer.

SEQ ID NO: 26 shows the sequence of the SKB11 forward primer.

SEQ ID NO: 27 shows the sequence of the SKB12 reverse primer.

SEQ ID NO: 28 shows the sequence of the SKB13 forward primer.

SEQ ID NO: 29 shows the sequence of the SKB14 reverse primer.

SEQ ID NO: 30 shows the sequence of the SKA1 forward primer.

SEQ ID NO: 31 shows the sequence of the SKA2 reverse primer.

SEQ ID NO: 32 shows the sequence of the SKA3 forward primer.

SEQ ID NO: 33 shows the sequence of the SKA4 reverse primer.

SEQ ID NO: 34 shows the sequence of the SKA5 forward primer.

SEQ ID NO: 35 shows the sequence of the SKA6 reverse primer.

SEQ ID NO: 36 shows the sequence of the SKA7 forward primer.

SEQ ID NO: 37 shows the sequence of the SKA8 reverse primer.

SEQ ID NO: 38 shows the sequence of the SKA9 forward primer.

SEQ ID NO: 39 shows the sequence of the SKA10 reverse primer.

SEQ ID NO: 40 shows the sequence of the SKA11 forward primer.

SEQ ID NO: 41 shows the sequence of the SKA12 reverse primer.

SEQ ID NO: 42 shows the sequence of the BHD consensus sequence.

DETAILED DESCRIPTION

I. Abbreviations
   BHD: Birt-Hogg-Dubé
   bp: base pair(s)
   DNA: deoxyribonucleic acid
   ELISA: enzyme-linked immunosorbant assay
   PCR: polymerase chain reaction II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Altered expression: Expression of a biological molecule (for example, mRNA or protein) in a subject or biological sample from a subject that deviates from expression if the same biological molecule in a subject or biological sample from a subject having normal characteristics for the biological condition associated with the molecule. Normal expression can be found in a control, a standard for a population, etc. For instance, characteristics of normal expression might include an individual who is not suffering from BHD syndrome, a population standard of individuals believed not to be suffering from BHD syndrome, etc.

Altered expression of a biological molecule may be associated with a disease. The term "associated with" includes an increased risk of developing the disease as well as the disease itself. For instance, certain altered expression, such as altered BHD nucleic acid or BHD protein (folliculin) expression, can be described as being associated with BHD syndrome.

Altered protein expression, such as altered BHD protein expression, refers to expression of a protein that is in some manner different from expression of the protein in a normal (wild type) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of a decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Controls or standards appropriate for comparison to a sample, for the determination of altered expression, include samples believed to express normally as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Animal: Living multi-cellular vertebrate organisms, a category that includes for example, mammals and birds.

Antisense, Sense, and Antigene: Double-stranded DNA (dsDNA) has two strands, a 5'->3' strand, referred to as the plus strand, and a 3'->5' strand (the reverse compliment), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Biological condition: Designates a condition of a subject that can be assessed through observation or through the analysis of a biological sample, for example, expression level of BHD protein.

Biological sample: Any sample in which the presence of a protein and/or ongoing expression of a protein may be detected. Suitable biological samples include samples containing genomic DNA or RNA (including mRNA), obtained from body cells of a subject, such as those present in peripheral blood, urine, saliva, tissue biopsy, surgical specimen, amniocentesis samples and autopsy material.

BHD Protein: (see Folliculin).

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

DNA (deoxyribonucleic acid): A long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side being joined together.

Effective amount of a compound: A quantity of compound sufficient to achieve a desired effect in a subject being treated. An effective amount of a compound can be administered in a single dose, or in several doses, for example, daily, during a course of treatment. However, the effective amount of the compound will be dependent on the compound applied, the subject being treated, the severity and type of the affliction, and the manner of administration of the compound.
The general term "administering to the subject" is understood to include all animals (for example, humans, apes, dogs, cats, horses, and cows) that have or may develop a tumor.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Folliculin: A BHD protein that has a coiled-coil domain, three myristoylation sites, and an N-glycosylation site. In some examples, folliculin is the 579 amino acid BHD protein shown in SEQ ID NO: 2. Wild-type human folliculin (SEQ ID NO: 2) shows no homology to any known proteins. Specific, non-limiting examples of mutant folliculin proteins are shown in SEQ ID NOs: 4, 6, 8, 10, and 12, and are described in Table 2.

Folliculin has been identified in a number of non-human species. Mouse folliculin (SEQ ID NO: 14; MGC37841 gene product, AAH25820 protein) is 92% identical to human folliculin (SEQ ID NO: 2). *Drosophila melanogaster* folliculin (CG8616 gene product) is 22-36% identical (44-56% positive) to human folliculin. *Caenorhabditis elegans* folliculin (F22D3.2 gene product, AAK31497 protein) is 27-28% identical (44-52% positive) to human folliculin.

Mutations in the BHD gene, for example, mutations that produce truncated folliculin proteins, lead to BHD disease. Mutations are particularly likely to occur in residues 1733-1740 of SEQ ID NO:1, which represent a "hot spot" for expansion or contraction mutations in the BHD encoding sequence.

Functional fragments and variants of a polypeptide: Included are those fragments and variants that maintain at least one function of the parent polypeptide. It is recognized that the gene or cDNA encoding a polypeptide can be considerably mutated without materially altering one or more of the polypeptide's functions. First, the genetic code is well known to be degenerate, and thus different codons encode the same amino acids. Second, even where an amino acid substitution is introduced, the mutation can be conservative and have no material impact on the essential functions of a protein (see Stryer, *Biochemistry* 4$^{th}$ Ed., (c) W. Freeman & Co., New York, N.Y., 1995). Third, part of a polypeptide chain can be deleted without impairing or eliminating all of its functions. For example, sequence variants in a protein, such as a 5' or 3' variant, may retain the full function of an entire protein. Fourth, insertions or additions can be made in the polypeptide chain, for example, adding epitope tags, without impairing or eliminating its functions (Ausubel et al., *Current Protocols in Molecular Biology*, Greene Publ. Assoc. and Wiley-Intersciences, 1998). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, sumoylation, labeling, for example, with radionuclides, and various enzymatic modifications, as will be readily appreciated by those well skilled in the art. A variety of methods for labeling polypeptides and labels useful for such purposes are well known in the art, and include radioactive isotopes such as $^{32}P$, ligands that bind to or are bound by labeled specific binding partners (for example, antibodies), fluorophores, chemiluminescent agents, enzymes, and antiligands. Functional fragments and variants can be of varying length. For example, a fragment may consist of 10 or more, 25 or more, 50 or more, 75 or more, 100 or more, or 200 or more amino acid residues.

Heterologous: A type of sequence that is not normally (for example, in the wild-type sequence) found adjacent to a second sequence. In one embodiment, the sequence is from a different genetic source, such as a virus or organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

In vitro amplification: When used in reference to a nucleic acid, techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744, 311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: A biological component (such as a nucleic acid molecule, protein or organelle) that has been substantially completely separated or purified away from other biological components in the cell of the organism in which the component naturally occurs, for example, other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

Labeled: A biomolecule attached covalently or noncovalently to a detectable label or reporter molecule. Typical labels include radioactive isotopes, enzyme substrates, cofactors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, CSHL, New York, 1989 and Ausubel et al., *Current Protocols in Molecular Biology*, Greene Publ. Assoc. and Wiley-Intersciences, 1998. For example, ATP can be labeled in any one of its three phosphate groups with radioisotopes such as $^{32}P$ or $^{33}P$, or in its sugar moiety with a radioisotope such as $^{35}S$.

Mammal: This term includes both human and non-human mammals. Similarly, the term subject includes both human and veterinary subjects.

Modulator: An agent that increases or decreases (modulates) the activity of a protein as measured by the change in an experimental parameter. A modulator can be essentially any compound, such as a chemotherapeutic agent, a polypeptide, a hormone, a nucleic acid, a sugar, a lipid and the like.

Mutation: Any change of the DNA sequence within a gene or chromosome. In some instances, a mutation will alter a characteristic or trait (phenotype), but this is not always the case. Types of mutations include base substitution point mutations (for example, transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance, those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as defined below, but generally refers to the subset of constitutional alterations that have arisen within the past few generations in a kindred and that are not widely disseminated in a population group. In particular embodiments, the term is directed to those constitutional alterations that have major impact on the health of affected individuals.

Nucleotide: This term includes, but is not limited to, a monomer that includes a base linked to a sugar, such as a pyrimidine, purine, or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example, a sequence (such as DNA or RNA) that is at least 6 bases, for example, at least 8, 10, 15, 20, 25, 30, 35, 40, 45, 50, 100 or even 200 bases long, or from about 6 to about 50 bases, for example, about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Pharmaceutically acceptable carriers: The pharmaceutically acceptable carriers useful with the compositions provided herein are conventional. Martin, *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Polypeptide: A polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragments of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

The term soluble refers to a form of a polypeptide that is not inserted into a cell membrane.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity can be found at the NCBI website.

Polymorphism: Variant in a sequence of a gene, usually carried from one generation to another in a population. Polymorphisms can be those variations (nucleotide sequence differences) that, while having a different nucleotide sequence, produce functionally equivalent gene products, such as those variations generally found between individuals, different ethnic groups, or geographic locations. The term polymorphism also encompasses variations that produce gene products with altered function, for example, variants in the gene sequence that lead to gene products that are not functionally equivalent. This term also encompasses variations that produce no gene product, an inactive gene product, or decreased or increased activity of the gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (for example, an alteration of a secondary structure such as a stem-loop, or an alteration of the binding affinity of the nucleic acid for associated molecules, such as polymerases, RNases, and so forth).

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of BHD encoding nucleotide will anneal to a target sequence, such as a BHD encoding sequence homolog from the gene family contained within a human genomic DNA library, with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of BHD nucleotide sequences.

The disclosure thus includes isolated nucleic acid molecules that comprise specified lengths of the disclosed BHD cDNA sequences. Such molecules can comprise at least 17, 20, 23, 25, 30, 35, 40, 45, or 50 consecutive nucleotides of these sequences, and can be obtained from any region of the disclosed sequences. By way of example, the BHD cDNA sequences can be apportioned into halves, thirds or quarters based on sequence length, and the isolated nucleic acid molecules can be derived from the first or second halves of the molecules, from any of the three thirds or any of the four quarters. By way of example, the human BHD cDNA, ORF, coding sequence and gene sequences can be apportioned into about halves, thirds or quarters based on sequence length, and the isolated nucleic acid molecules (for example, oligonucleotides) can be derived from the first or second halves of the molecules, from any of the three thirds, or any of the four quarters. The cDNA also could be divided into smaller regions, for example, about eighths, sixteenths, twentieths, fiftieths and so forth, with similar effect.

Another mode of division is to select the 5' (upstream) and/or 3' (downstream) region associated with a BHD encoding sequence, or to select an intron or portion thereof.

Protein: A biological molecule expressed by a gene and comprised of amino acids.

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one embodiment, the molecule is a polypeptide that is at least 50% free of other proteins, lipids, carbohydrates, or other materials with which it is naturally associated. In another embodiment, the polypeptide is at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the BHD protein, and the corresponding cDNA sequence, will possess a relatively high degree of sequence identity when aligned using standard methods. This homology will be more significant when the orthologous proteins or cDNAs are derived from species that are more closely related (for example, human and chimpanzee sequences), compared to species more distantly related (for example, human and *C. elegans* sequences).

By way of example, the mouse ortholog (SEQ ID NO: 14; MGC37841 gene product, AAH25820 protein) is 92% identical to human folliculin (SEQ ID NO: 2). The *Drosophila melanogaster* ortholog (CG8616 gene product) is 22-36% identical (44-56% positive) to the human folliculin. Finally, the *Caenorhabditis elegans* ortholog (F22D3.2 gene product, AAK31497 protein) is 27-28% identical (44-52% positive) to the human folliculin.

Methods of alignment of sequences for comparison are well known in the art. Various programs and alignment algorithms are described in: Smith and Waterman *J. Mol. Biol.* 147(1):195-197, 1981; Needleman and Wunsch *J. Mol. Biol.* 48: 443-453, 1970; Pearson and Lipman *Proc. Natl. Acad. Sci. USA* 85: 2444-2448, 1988; Higgins and Sharp *Gene,* 73: 237-244, 1988; Higgins and Sharp *CABIOS* 5: 151-153, 1989; Corpet et al. *Nuc. Acids Res.* 16, 10881-10890, 1988; Huang et al. *Computer Appls. in the Biosciences* 8, 155-165, 1992; and Pearson et al. *Meth. Mol. Bio.* 24, 307-331, 1994. Furthermore, Altschul et al. (*J. Mol. Biol.* 215:403-410, 1990) present a detailed consideration of sequence alignment methods and homology calculations.

The NCBI Basic Local Alignment Search Tool (BLAST) (Altschul et al. *J. Mol. Biol.* 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. The Search Tool can be accessed at the NCBI website, together with a description of how to determine sequence identity using this program.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) *Molecular Cloning: A Laboratory Manual*, CSHL, New York and Tijssen (1993) *Laboratory Techniques in Biochemistry and Molecular Biology—Hybridization with Nucleic Acid Probes* Part I, Chapter 2, Elsevier, New York. Nucleic acid molecules that hybridize under stringent conditions to a human BHD encoding sequence will typically hybridize to a probe based on either an entire human BHD encoding sequence or selected portions of the gene under wash conditions of 2×SSC at 50° C. A more detailed discussion of hybridization conditions is presented below.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Small interfering RNAs: Synthetic or naturally-produced small double stranded RNAs (dsRNAs) that can induce gene-specific inhibition of expression in invertebrate and vertebrate species are provided. These RNAs are suitable for interference or inhibition of expression of a target gene and comprise double stranded RNAs of about 15 to about 40 nucleotides containing a 3' and/or 5' overhang on each strand having a length of 0- to about 5-nucleotides, wherein the sequence of the double stranded RNAs is essentially identical to a portion of a coding region of the target gene for which interference or inhibition of expression is desired. The double-stranded RNAs can be formed from complementary ssRNAs or from a single stranded RNA that forms a hairpin or from expression from a DNA vector.

Specific binding agent: An agent that binds substantially only to a defined target. Thus, a BHD protein-specific binding agent binds substantially only the BHD protein. As used herein, the phrase BHD protein-specific binding agent includes anti-BHD protein antibodies (such as monoclonal antibodies) and other agents (such as soluble receptors) that bind substantially only to the BHD protein. BHD specific binding agents can also be produced that bind substantially only to mutant BHD protein and not to wild-type BHD protein, or that bind substantially only to wild-type BHD protein and not to mutant BHD protein. Such specific binding agents are described in greater detail below. Such specific binding agents are useful in the detection of BHD disease.

Anti-BHD protein antibodies can be produced using standard procedures described in a number of texts, including Harlow and Lane (*Antibodies, A Laboratory Manual*, CSHL, New York, 1988). The determination that a particular agent binds substantially only to the BHD protein can readily be made by using or adapting routine procedures. One suitable in vitro assay makes use of the Western blotting procedure (described in many standard texts, including Harlow and Lane, *Antibodies, A Laboratory Manual*, CSHL, New York, 1988). Western blotting can be used to determine that a given BHD protein (folliculin) binding agent, such as an anti-BHD protein monoclonal antibody, or folliculin amino- or carboxy-terminal peptide-derived polyclonal antibody, binds substantially only to the BHD protein. A phosphospecific binding agent specifically binds to a peptide containing a phosphorylated residue.

Shorter fragments of antibodies can also serve as specific binding agents. For instance, Fabs, Fvs, and single-chain Fvs (SCFvs) that bind to folliculin would be BHD-specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody (SCA), a genetically engineered molecule containing the variable region of the light chain, the variable region of the heavy chain, linked by a suitable polypeptide linker as a genetically fused single chain molecule. Methods of making these fragments are routine.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example, under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference.

The following is an exemplary set of hybridization conditions:

Very High Stringency (Detects Sequences that Share 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share 80% Identity or Greater)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share Greater than 50% Identity)
Hybridization: 6×SSC at RT to 55° C. for 16-20 hours
Wash at least twice: 2×-3×SSC at RT to 55° C. for 20-30 minutes each.

Subject: Living multi-cellular vertebrate organisms, a category that includes both human and non-human mammals.

Target sequence: "Target sequence" is a portion of ssDNA, dsDNA, or RNA that, upon hybridization to a therapeutically effective oligonucleotide or oligonucleotide analog, results in the inhibition of expression. For example, hybridization of therapeutically effectively oligonucleotide to a BHD target sequence results in inhibition of BHD expression. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Test compound: A test compound can be essentially any compound, such as a chemotherapeutic, a polypeptide, a hormone, a nucleic acid, a sugar, a lipid and the like.

Therapeutically effective amount of a folliculin protein: A quantity of folliculin protein sufficient to achieve a desired effect in a subject being treated. For instance, this can be the amount necessary to inhibit or to measurably reduce a skin lesion associated with BHD syndrome.

An effective amount of a folliculin protein may be administered in a single dose, or in several doses, for example, daily or more often, during a course of treatment. However, the effective amount of folliculin or a fragment thereof will be dependent on the folliculin protein applied, the subject being treated, the severity and type of the affliction, and the manner of administration of the fusion protein.

The fusion proteins disclosed in the present invention have equal application in medical and veterinary settings. Therefore, the general term "subject being treated" is understood to include all animals (for example, humans, apes, dogs, cats, horses, and cows) that are or may display a symptom of BHD syndrome that is susceptible to folliculin protein-mediated amelioration.

Transfected: A process by which a nucleic acid molecule is introduced into cell, for instance by molecular biology techniques, resulting in a transfected cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Treating a disease: Includes inhibiting or preventing the partial or full development or progression of a disease, for example, in a person who is known to have a predisposition to a disease. Furthermore, treating a disease refers to a therapeutic intervention that ameliorates at least one sign or symptom of a disease or pathological condition, or interferes with a pathophysiological process, after the disease or pathological condition has begun to develop.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprises" means "includes." Hence "comprising A or B" means include A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Identification of a BHD Encoding Sequence

This disclosure provides BHD encoding sequences and proteins. These were identified by recombination mapping, which showed a disease-segregating insertion/deletion mutation within a previously uncharacterized gene. The full-length BHD cDNA sequence (SEQ ID NO: 1) was then isolated and sequenced from multiple cDNA libraries, and the predicted protein product (SEQ ID NO: 2) was based on computer-generated predictions. Methods of using these BHD encoding sequences and proteins are also provided herein.

Recombination mapping was used to narrow the minimal BHD region to 700 kb. Known candidate genes and uncharacterized mRNAs from within this 700 kb region were then screened for mutations in a panel of subjects who had been diagnosed with BHD. In five of nine BHD kindreds, a disease-cosegregating insertion/deletion mutation was identified in a mononucleotide $(C)_8$ tract within a previously uncharacterized gene (residues 1733-1740 of SEQ ID NO: 1). This mutation produced a frameshift predicting a premature termination of the protein translation. An additional 22 of 53 BHD family probands were tested that were found to harbor the mononucleotide C tract insertion/deletion mutation, indicating that this sequence (residues 1733-1740 of SEQ ID NO: 1) is a "hot spot" for expansion or contraction mutations in the BHD encoding sequence. Thus, other mutations are likely to be found in this region, in particular. In addition, several other germline BHD encoding sequence mutations were identified in the patient panel that resulted in frameshifts and predicted protein truncations. All of the mutations cosegregated with disease in BHD families, and none were present in 160 normal individuals tested for the mutations.

The full-length BHD cDNA sequence (SEQ ID NO: 1) was then isolated and sequenced from multiple cDNA libraries. Northern blot analysis revealed a 3.8 kb transcript expressed in most normal fetal and adult tissues, including lung, kidney and skin. The predicted 579 amino acid BHD protein (SEQ ID NO: 2), also referred to herein as folliculin, has a coiled-coil domain, three myristoylation sites, and an N-glycosylation site, based on computer program-generated predictions. The protein sequence shows no homology to any known proteins. The identified mutant BHD mRNA sequences and encoded mutant folliculin proteins are shown in SEQ ID NOs: 3-12, and are described more fully below and in Table 2. A BHD consensus sequence is shown in SEQ ID NO: 42. One embodiment of the disclosure is a cell, for example, a human cell that has been transformed with a BHD nucleic acid sequence.

The discovery of germline BHD encoding sequence mutations responsible for the BHD syndrome makes possible the understanding of the biological role of the BHD protein, folliculin, in pathways common to skin, lung and kidney organogenesis, and to new treatments for BHD skin lesions and more effective therapies for renal cancer. In particular, mutations in the gene can be used in the differential diagnosis of BHD disease and in a DNA diagnostic test for BHD mutations, for instance using a blood sample. Such tests are particularly useful in detecting asymptomatic mutation carriers in BHD families.

Identification of the BHD encoding sequence also makes possible novel therapies for treatment of BHD skin lesions (fibrofolliculomas). For example, creams or other preparations containing the BHD protein, folliculin, are proposed for use to reduce the size and appearance of the benign hair follicle tumors. Furthermore, the BHD encoding sequence is used in the differential diagnosis of sporadic kidney cancer; the BHD encoding sequence is the third gene found to be responsible for inherited kidney cancer, and mutation testing allows diagnosis and initiation of the proper treatment, which is different for each of the types of kidney cancer caused by the three genes.

Additionally, the BHD encoding sequence is used in the differential diagnosis for spontaneous pneumothorax or collapsed lung, as well as in diagnosing a propensity to develop spontaneous pneumothorax. Collapsed lung can be caused by several factors, and a BHD diagnostic test allows a physician to determine if the emergency situation resulting from the subject's collapsed lung is likely to recur, and whether the subject carries the predisposition to develop additional spontaneous pneumothoraces due to a BHD encoding sequence mutation. Furthermore, the BHD encoding sequence is used in the differential diagnosis for renal neoplasms and fibrofolliculomas, as well as in diagnosing a propensity to develop renal neoplasms and fibrofolliculomas.

Other embodiments are isolated nucleic acid sequences that hybridize with BHD nucleic acid sequence under low stringency, high stringency, or very high stringency conditions. A further embodiment is a pharmaceutical composition that includes a folliculin protein and a pharmaceutically acceptable carrier or diluent. The pharmaceutical composition is used, for example, in treating BHD disease.

Still other embodiments are single-stranded oligonucleotides that hybridize under highly stringent conditions to a nucleic acid molecule having the sequence of a mutant BHD sequence that encodes a truncated BHD protein associated with BHD disease, but that does not hybridize under highly stringent conditions to SEQ ID NO: 1. For example, in certain embodiments, the oligonucleotide hybridizes under highly stringent conditions to the mutant BHD sequence encoding the protein sequence shown in SEQ ID NOs: 4, 6, 8, 10, or 12. In some embodiments, the oligonucleotide includes at least 10 consecutive nucleotides of the complements of the mutant BHD sequence encoding the protein sequence shown in SEQ ID NOs: 4, 6, 8, 10, or 12. In yet still another embodiment, the oligonucleotide is included in an array of nucleic acid molecules attached to a solid support. In particular embodiments, the oligonucleotide recognizes one or more of the following mutations: a) deletion of the guanosine of position 1088 of SEQ ID NO: 1, b) insertion of the nucleic acid sequence GTGTTGCCAGAGAGTACAGAAAGCCCCT (nucleotides 1389-1416 of SEQ ID NO: 42) at position 1389 of SEQ ID NO: 1, c) insertion of a cytosine at position 1741 of SEQ ID NO: 1, d) deletion of the cytosine at position 1740 of SEQ ID NO: 1, or e) substitution of a cytosine for the guanine at position 1844 of SEQ ID NO: 1.

Yet still another embodiment is an antisense oligonucleotide that inhibits the expression of the BHD protein encoded by SEQ ID NO: 1. Further embodiments are methods that include obtaining a sample of nucleic acid from a subject, and determining an identity of a nucleotide that results in truncation of the BHD protein. In certain examples, the determining step includes amplifying at least a portion of a nucleic acid molecule comprising the BHD gene. In certain other examples the determining step includes sequencing at least a portion of a nucleic acid molecule comprising the BHD gene. In still other examples, the method includes determining a propensity to develop a condition associated with BHD disease, and in particular examples, the condition includes fibrofolliculoma, renal neoplasia, or spontaneous pneumothorax.

Other embodiments include a purified polypeptide having an amino acid sequence that includes the sequence as set forth in SEQ ID NO: 2 or sequences having at least 95% sequence identity to SEQ ID NO: 2. In certain examples, sequence has at least 98% sequence identity to SEQ ID NO: 2. Also disclosed is a nucleic acid that encodes a purified polypeptide having an amino acid sequence comprising the sequence as set forth in SEQ ID NO: 2 or sequences having at least 95% sequence identity to SEQ ID NO: 2. In particular examples, the purified polypeptide includes SEQ ID NO: 2 with 0 to 10 conservative amino acid substitutions.

Still other embodiments are purified polypeptides that bind specifically to an antibody that binds specifically to BHD protein. Some examples include a purified antibody that selectively binds to an epitope of a BHD protein. In some examples, the epitope is a region on the BHD protein that is truncated in BHD disease. In particular examples, the epitope is within amino acid residues 479 to 579 of SEQ ID NO: 2, and in certain examples the antibody binds specifically to a mutant form of BHD but not to a normal form of BHD.

EXAMPLES

Example 1

Identification and Characterization of the BHD Gene

The triad of dermatologic lesions, including fibrofolliculomas, trichodiscomas and achrocordons, known as the Birt-Hogg-Dubé syndrome (BHD), was originally described in a Canadian kindred in 1977 (Birt et al., *Arch. Dermatol.* 113: 1674-1677, 1977). Other phenotypic features were found to be associated with BHD including renal neoplasia (Roth et al., *J. Amer. Acad. Derm.* 29:1055-1056, 1993; Toro et al., *Arch. Dermatol.* 135:1195-1202, 1999), lung cysts and/or spontaneous pneumothorax (Toro et al., *Arch. Dermatol.* 135: 1195-1202, 1999; Binet et al., *Ann. Dermatol. Venereol.* 113: 928-930, 1986). When adjusted for age, patients with fibrofolliculomas have a seven-fold increased risk for developing renal neoplasms and a 50-fold increased risk for developing spontaneous pneumothorax compared with their unaffected siblings (Zbar et al., *Cancer Epidem. Bio. Prev.* 11:393-400, 2002). Lung cysts develop frequently (83%) in affected members of BHD families (Roth et al., *J. Amer. Acad. Derm.* 29:1055-1056, 1993; Toro et al., *Arch. Dermatol.* 135:1195-1202, 1999; Zbar et al., *Cancer Epidem. Bio. Prev.* 11:393-400, 2002). Renal tumors associated with BHD include chromophobe (the predominant histologic variant), oncocytoma, oncocytic hybrid (a newly described hybrid between chromophobe and oncocytoma; Tickoo et al., *Amer. J. Surg. Pathol.* 23:1094-1101, 1999) and clear cell (Zbar et al., *Cancer Epidem. Bio. Prev.* 11:393-400, 2002). The BHD disease locus was initially localized by linkage analysis in nine families to a 4 cM region of chromosome 17p11.2 between D17S1857 and D17S805 (Schmidt et al., *Am. J. Hum. Genet.* 69:876-882, 2001). Linkage to a 35 cM overlapping region spanning 17p12-q11.2 was reported in a Swedish BHD pedigree with associated renal neoplasms (Khoo et al., *Oncogene* 20:5239-5242, 2001).

Methods

Patient Recruitment and Sampling

Families affected with BHD were recruited and evaluated at the Clinical Center, National Institutes of Health, and also on field trips. Patients were interviewed for a prior history of renal tumors and spontaneous pneumothorax, and were evaluated by a dermatologist. Affected status was confirmed by the presence of 10-100 skin papules on the face, neck or upper torso with at least one histologically proven fibrofolliculoma. Blood samples were drawn for DNA preparation and to establish EBV-immortalized B cell lines.

Development of Microsatellites

To increase the density of microsatellite markers in the region of BHD linkage, we identified new polymorphic di-, tri- and tetranucleotide tracts by BLAST of $(CA)_{16}$, $(TATG)_8$ and $(TGC)_8$ against the BAC genomic sequences from the region. Primers were designed to amplify potential polymorphic microsatellites and selected for a heterozygosity >0.6 in a panel of 8 unrelated individuals. Microsatellite genotyping and haplotype analysis was performed as described (Schmidt et al., Am. J. Hum. Genet. 69:876-882, 2001).

Candidate Gene Selection and Analysis

The BHD critical region at 17p11.2 was examined for known genes, uncharacterized mRNAs, spliced EST clusters, unspliced EST clusters, and predicted gene exons (in that order). These categories are clearly delineated by the University of California, Santa Cruz (UCSC) human genome browser, which served as a primary reference. Additional details were obtained from Celera, NCBI, and Ensembl human and mouse genome assemblies, and annotation of individual BAC clones by Doubletwist.

Exon/intron boundaries were determined by BLAST alignment of the cDNA of each candidate gene with BAC genome sequence. Primers located in neighboring introns at least 20 base pairs from the splice junctions were designed with the aid of Oligo Tech ver. 1 (Oligos Etc & Oligo Therapeutics). For large exons, overlapping amplicons were generated which covered the entire coding sequence.

Candidate gene exons were amplified from a panel of patients representing nine families affected with BHD and 3 unaffected individuals to detect nondisease-related mutations. Standard PCR conditions were employed with AMPLITAQ® (Perkin Elmer, Waltham, Mass.) or Taq polymerases (Invitrogen, Carlsbad, Calif.). PCR products were quantitated by agarose gel electrophoresis and purified using Multiscreen PCR cleanup plates (Millipore, Billerica, Mass.). Double-stranded sequencing reactions (10 µl) using BIGDYE® Terminators ready reaction mix (Applied Biosystems, Carlsbad, Calif.) were purified using PERFORMA® plates (Edge Biosystems, Gaithersburg, Md.) and electrophoresed on an ABI 3700 genetic analyzer.

Chromatograms were aligned and analyzed using LASERGENE® software (DNAStar, Madison, Wis.). Alignments were examined using the conflict finder to locate Phred-identified discrepancies, then forward and reverse chromatograms from each affected patient were manually examined to locate additional secondary peaks. Sequence variants found in one or more affected patients (but not in unaffected individuals) were examined for cosegregation with disease in their respective families by denaturing high performance liquid chromatography (DHPLC) or single-stranded sequencing. Insertions and deletions were subcloned with a TOPO® Cloning Kit (Invitrogen, Carlsbad, Calif.) and sequenced. A minimum of 160 normal individuals were examined for the presence of each disease-associated sequence variant. DHPLC was performed using a Transgenomic WAVE® chromatography system with a DNASEP® column. Temperature predictions were obtained by the Stanford melt algorithm or WAVE-MAKER™ software (Transgenomic, Omaha, Nebr.). Runs were nine minutes and included a 75% acetonitrile wash followed by a high A buffer rinse (to clear acetonitrile).

Analysis of the BHD Gene

Two overlapping, uncharacterized, full-length transcripts were sequenced by the NIH Mammalian Gene Collection project and deposited in GenBank on Oct. 9 and 11, 2001. The mRNAs (GenBank Accession nos. BC015725 and BC015687) were derived from skin melanoma and were included in the UCSC Genome Browser release of Dec. 22, 2001. These transcripts highlighted a spliced EST cluster located in BAC clone RP11-45M22 (GenBank Accession no. AC055811), which were analyzed for mutations. Intronic primers were designed to amplify 14 coding exons and splice junctions for sequencing. PCR reaction components were standard. Cycling conditions: 95° C. for 3 minutes, 94° C. for 45 seconds, annealing $T_m$ for 1 minute, 72° C. for 1 minute for 40 cycles. Primer sequences are shown in Table 1.

Cosegregation of mononucleotide insertion/deletion mutations with affected haplotype carriers in BHD was determined by single-stranded sequencing of exon 11 amplicons from patient DNA. A 28 bp duplication allele associated with BHD in Family 228 was separated from the wild-type allele by electrophoresis on a 4-20% gradient polyacrylamide gel (Novex) according to manufacturer's protocols. Family consegregation studies of missense mutations were conducted using DHPLC.

Northern Blot Analysis

Expression of the BHD gene transcript was evaluated with human poly A+ RNA blots (Origene Technologies, Inc., Rockville, Md.) containing 12 major tissues, including lung and kidney, and 6 minor tissues, including skin. A human fetal poly A+ RNA blot containing kidney, lung, brain, and liver was purchased from Clontech, Mountain View, Calif. The exon 11 amplicon of the BHD gene was used as a template for RNA antisense probe labeling using STRIP-EZ™ Probe Synthesis and Removal Kit (Ambion, Inc., Austin, Tex.) in a linear PCR reaction with $^{32}$P-dATP and the antisense gene specific primer according to the manufacturer's protocols. Hybridizations were carried out in ULTRAHYB® hybridization solution with a one hour prehybridization (Ambion, Inc., Austin, Tex.) at 42° C. overnight, and washed by standard methods.

TABLE 1

| Exon | Forward Primer | Reverse Primer | Amplicon size (bp) | Annealing temp (C) |
|---|---|---|---|---|
| 1 | SEQ ID NO: 16 SKB1: GGACTCTGGCCCTAAACCC | SEQ ID NO: 17 SKB2: GTACGGCTCAGGGAGTCAC | 385 | 64 |
| 2 | SEQ ID NO: 18 SKB3: GACAGCAAGCCTGGGCCAAG | SEQ ID NO: 19 SKB4: CATGCTACGAAGGCCTCTAATC | 225 | 64 |
| 3 | SEQ ID NO: 20 SKB5: AAGGACGATGTGCATGGTGG | SEQ ID NO: 21 SKB6: CACTGCCAGCCCAGCTAAG | 256 | 64 |

TABLE 1-continued

| Exon | Forward Primer | Reverse Primer | Amplicon size (bp) | Annealing temp (C) |
|---|---|---|---|---|
| 4 | SEQ ID NO: 22 SKB7: CACTGCTCTCAGGTCCTCC | SEQ ID NO: 23 SKB8: GGAGGTTTCATGGAGTCAATAGG | 406 | 64 |
| 5 | SEQ ID NO: 24 SKB9: AGTGCCTGCCTCCCTGTGC | SEQ ID NO: 25 SKB10: ACCTAAGAGAGTTTGTCGCCCTG | 310 | 64 |
| 6 | SEQ ID NO: 26 SKB11: TCAGCACAGAGCGGCTCATG | SEQ ID NO: 27 SKB12: GAAGAGGCTTTGATTTGGTGTCAC | 354 | 64 |
| 7 | SEQ ID NO: 28 SKB13: CCAATGTATCGTGACTGCTCTATC | SEQ ID NO: 29 SKB14: GGTCCGAGCTGCTGGCAG | 278 | 64 |
| 8 | SEQ ID NO: 30 SKA1: GCCCCAGATCAGGAACCTG | SEQ ID NO: 31 SKA2: CTGGGTGAGCGTCAGGTTTGC | 607 | 64 |
| 9 | SEQ ID NO: 32 SKA3: CCATGACTGGCTCTCCTCCT | SEQ ID NO: 33 SKA4: GTATCTTGGGCTGAAGTCACAGG | 313 | 62 |
| 10 | SEQ ID NO: 34 SKA5: GCACCAGGCCAATACTGC | SEQ ID NO: 35 SKA6: GTCTTTCTCCTGAGCCCTGTC | 290 | 64 |
| 11 | SEQ ID NO: 36 SKA7: 5'GGTTCCACTTTGGGCCTGAG | SEQ ID NO: 37 SKA8: 5'GGTAGTAGAGCATGGATGGCC | 270 | 64 |
| 12 + 13 | SEQ ID NO: 38 SKA9: CAGCTCCAGGTTTTCTCCAGG | SEQ ID NO: 39 SKA10: CACGGTGGGCTAGCGCAG | 463 | 64 |
| 14 | SEQ ID NO: 40 SKA11: CCTCGGGAGCAGACATGTTATTG | SEQ ID NO: 41 SKA12: ACCAGGGCTCGAGGGATTG | 639 | 64 |

Somatic Cell Hybrids

Lymphoblasts from several BHD patients ($2\times10^7$) were fused with mouse RAG cells ($2\times10^6$) (HPRT-deficient mouse cell line from ATCC). Hybrids were selected in hypoxanthine aminopterin thymidine (HAT) medium at 37° C. DNA was prepared from expanded colonies and genotyped to determine whether one copy or both copies of human chromosome 17 were present in the hybrids.

Full Length Clones and Sequencing cDNA was obtained from normal adult kidney, and adult and fetal lung (purchased from Clontech, Mountain View, Calif.). Gene-specific primers were designed approximately 50 bases from the 5' and 3' ends and were used to amplify a 3.2 kb transcript from each library and shotgun sequenced. Takara (Shiga, Japan) long and accurate (LA) reagents were used to amplify the transcript with recommended buffer conditions and extension times. Sequencing primers were spaced approximately 500 bp apart on both strands for overlapping, double-stranded sequencing. A minimum of 4-fold coverage was obtained for each transcript. PCR from these cDNA pools was repeated with ADVANTAGE® Polymerase Mix (purchased from Clontech, Mountain View, Calif.). The structure of the normal transcript was assembled from the consensus sequence of these extension reactions.

Several cDNA libraries were screened and a longest clone was isolated from lung. The clone was also shotgun sequenced to >4 fold, double-stranded coverage. Evidence of alternative splicing is currently under investigation for a possible role in disease or normal folliculin function. Spliced I.M.A.G.E. clones identified from the UCSC Genome Browser were purchased and examined for additional 5' end sequence. These extended the Clontech transcript sequence 106 bases. 5' and 3' RACE studies of Clontech cDNA from lung and kidney confirmed the complete sequence of the normal gene.

Results

Figure 2A:
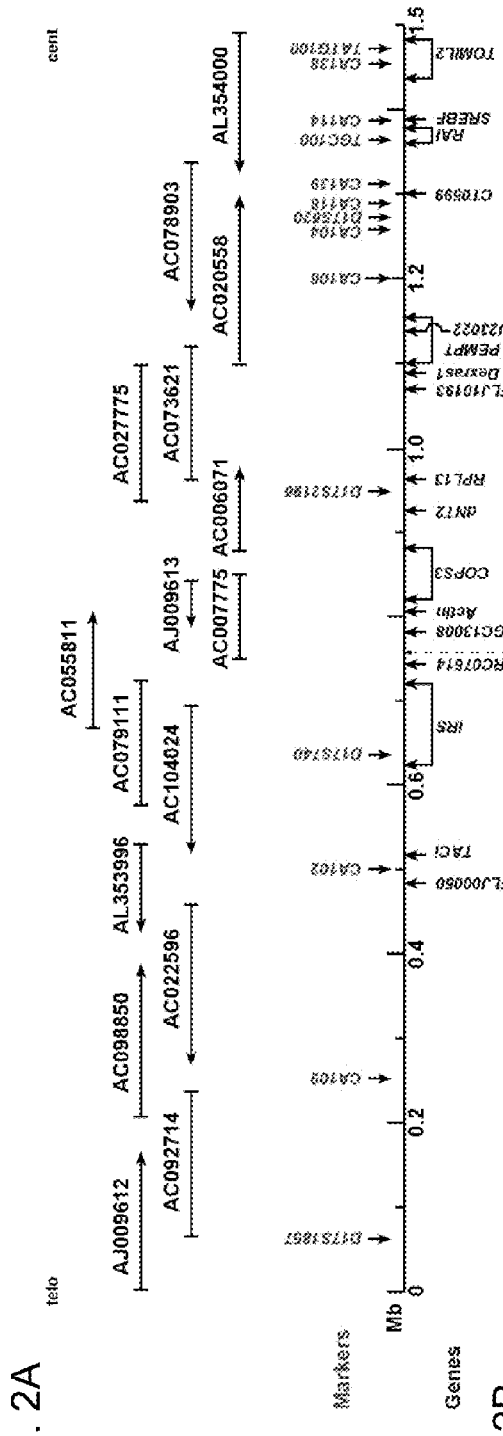
FIG. 2A is a map of the BAC tiling path, shown by black horizontal lines with arrowheads indicating directional read of completed sequence and GenBank accession numbers. BAC overlaps were confirmed by in silico and PCR methods. A single gap was spanned by exons of the COPS3 gene. Locations of polymorphic, markers and genes were confirmed in silico and by PCR amplification from BAC clones.

A comprehensive BAC tiling path map was produced by in silico methods using BLAST (Altschul et al., *J. Mol. Biol.* 215:403-410, 1990), and comparative analysis of genome assemblies, and identified locations of all known genes, uncharacterized mRNAs and spliced EST clusters in the 17p11.2 critical region (FIG. 2A). A PCR-based approach was used to confirm the locations of genes and markers on overlapping BACs. These results and fluorescence in situ hybridization data provided additional support for the BAC order. This BAC map is in agreement with the physical map of Lucas et al. (*Eur. J. Hum. Genet.* 9:892-902, 2001), but conflicts with the current UCSC Genome Browser (December, 2002), Celera and NCBI (April, 2002) genome assemblies. Difficulties with assembly of the 17p11.2 region are most likely due to the presence of low-copy number repeats [Smith-Magenis Syndrome (SMS) repeats], which cause DNA rearrangements, leading to microduplication/deletion syndromes such as Smith-Magenis Syndrome (Chen et al., *Ment. Retard. Dev. Disabil Res. Rev.* 2:122-129, 1996).

Candidate genes from the critical region were identified based on EST evidence of expression in skin, lung, and kidney. Exon/intron structure was determined and intronic primers were designed to amplify all coding sequences and splice junctions. High throughput mutation analysis was performed on a panel of patient DNA samples, representing nine BHD families. In total, 321 coding amplicons were sequenced, representing 39 known genes, uncharacterized mRNAs, and spliced EST clusters from the 4 cM region of linkage on 17p11.2.

Figure 2B:
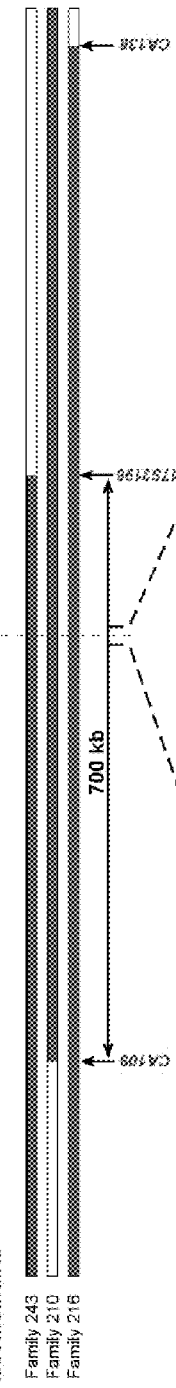
FIG. 2B is a map of the critical recombinants identified in Family 243 (D17S2196), Family 210(CA109) and Family 216 (CA138) which define the BHD minimal region to 700 kb. The nonrecombining region is shown in black shading.

In parallel with sequencing, 13 new polymorphic microsatellite markers were developed to look for new recombinants in the region of linkage. Further analysis of BHD Family 210, described previously (Schmidt et al., *Am. J. Hum. Genet.* 69:876-882, 2001), identified a recombination in the new distal marker CA109. Additional BHD families were analyzed and a proximal recombination identified in BHD Family 216 in the new marker CA138, which localized the BHD gene to a 1.3 Mb region between CA109 and CA138 (FIG. 2B). Subsequently, a proximal recombination was identified in another new BHD family, Family 243, at D1782196, which narrowed the BHD critical region further to 700 kb (FIG. 2B).

Figure 2C:
FIG. 2C is a map of the location of two overlapping, uncharacterized mRNAs from melanoma (GenBank Accession Nos. BC015725 and BC015687) shown within the 700 kb BHD candidate region. The BHD gene exon/intron structure with 14 coding exons is given.

Gene mining within the 700 kb critical region using the December, 2001 release of the UCSC Human Genome Browser identified two overlapping, uncharacterized, full-length transcripts from skin melanoma (GenBank Accession nos. BC015725 and BC015687), supported by additional ESTs (FIG. 2C). Northern blot analysis, using probes designed from either mRNA, revealed a 3.8 kb transcript in most adult and fetal tissues, indicating that these two mRNAs code for a single protein that is widely expressed (FIG. 5A).

Figure 3A:
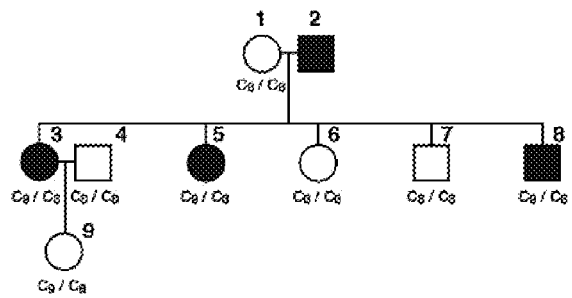
FIG. 3A. is a pedigree of Family 200. The pedigree shows cosegregation of the C insertion mutation ($C_9$) with disease (black symbols, affected status). Individual 9 is an asymptomatic mutation carrier with a history of spontaneous pneumothorax. Sequence analysis of somatic cell hybrid DNA from a BHD patient showed a C insertion in the $(C)_8$ tract (nt 1733-1740) within exon 11 on the affected chromosome and wild-type $(C)_8$ tract on the unaffected chromosome.

Sequence analysis of the 14 coding exons contained in these two mRNAs revealed mutations in 8 of 9 families on the panel (Table 2). A cytosine insertion mutation in a mononucleotide $(C)_8$ tract (nt 1733-1740) in exon 11 was identified in four BHD families (families 174, 200, 210, 216) and resulted in a frameshift (SEQ ID NO: 7) predicted to truncate the protein 26 missense amino acids downstream from the mutation (SEQ ID NO: 8). A cytosine deletion mutation in the same mononucleotide $(C)_8$ tract (SEQ ID NO: 9) was identified in one family (Family 201), which would truncate the protein 38 missense amino acids downstream from the mutation (SEQ ID NO: 10). Sequence analysis of somatic cell hybrids established from patients from several of these BHD families confirmed the presence of the $(C)_9$ allele on the affected chromosome 17 and the $(C)_8$ allele on the wild type chromosome 17 (FIG. 3A). Cosegregation of these C tract insertion/deletion mutations in BHD-affected haplotype carriers was confirmed by sequencing this amplicon in 30 affected and 28 unaffected family members.

Figure 3B:
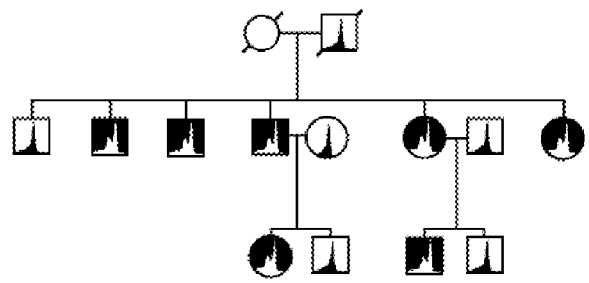
FIG. 3B. is a pedigree of Family 202. The mutation produced a unique DHPLC heteroduplex peak (insert in black symbol) which cosegregated with disease (black symbols, affected status). Unaffected individuals (white symbols, unaffected status) show a wild-type homoduplex DHPLC peak (insert in white symbol). Sequence analysis of subcloned PCR product from a BHD affected individual showed the delAGinsC mutation (nt 1087-1088) in exon 7.

A complex mutation, delAGinsC (SEQ ID NO: 3), which resulted in a frame shift and predicted protein truncation 11 missense amino acids downstream from the mutation (SEQ ID NO: 4), was identified in Family 202 in exon 7 at nt 1087-1088, and was shown to co-segregate with disease by DHPLC (FIG. 3B).

Figure 4A:
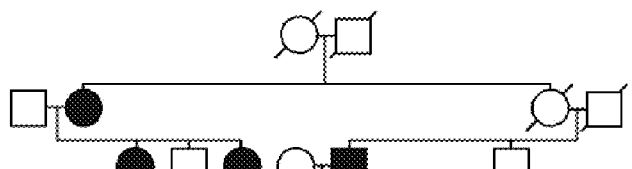
FIG. 4A. The pedigree shows cosegregation of the 28 bp allele with disease (black symbols, affected status).
Figure 4B:
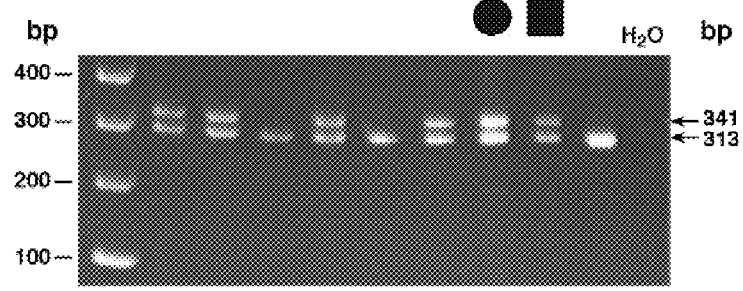
FIG. 4B. PCR products from the exon 9 amplicon were electrophoresed on a 4-20% polyacrylamide gradient gel to separate the 28 bp duplication allele (341 bp) from the wild-type allele (313 bp). Lane 1, 100 bp MW marker; lanes 2, 3, 5, 7, 8 and 9 represent affected individuals (black symbols); lanes 4, 6, and 10 represent unaffected individuals (white symbols); lane 11, water blank.

A 28-bp duplication (nt 1378-1405) was found in exon 9 of affected members of BHD Family 228 (described in Toro et al., *J. Med. Genet.* 39:E10, 2002) (SEQ ID NO: 5), which resulted in wild type and mutant allele size differences that were distinguishable on a 4-20% polyacrylamide gel (FIG. 4). The mutation created a termination codon 79 missense amino acids downstream from the end of the duplication (SEQ ID NO: 6).

Figure 3C:
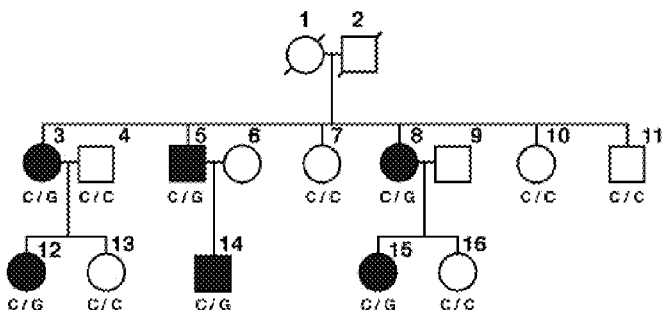
FIG. 3C is a pedigree of Family 230. The pedigree shows cosegregation of the mutation with disease (black symbols, affected status). Sequence analysis of exon 12 in BHD affected individuals showed a C->G mutation (nt 1844) which produces an in-frame termination at codon 463.

A fourth mutation was identified in BHD Family 230, a C to G transversion at nt 1844 (SEQ ID NO: 11) that produced an in-frame termination at codon 463 in exon 12 (FIG. 3C) (SEQ ID NO: 12).

Each family's mutation was present in affected haplotype carriers within that family, but was absent in non-carriers and at least 160 normal individuals.

TABLE 2

BHD gene mutations in a panel of nine families with BHD syndrome.

| Family | Exon | Mutation [a] | Predicted Result(s) | Seq. ID No: |
|---|---|---|---|---|
| 202 | 7 | 1087delAGinsC | Frameshift, protein truncation | 3 and 4 |
| 228 | 9 | 1378→1405dup | Frameshift, protein truncation | 5 and 6 |
| 174 | 11 | 1733insC | Frameshift, protein truncation | 7 and 8 |
| 200 | 11 | 1733insC | Frameshift, protein truncation | 7 and 8 |
| 210 | 11 | 1733insC | Frameshift, protein truncation | 7 and 8 |
| 216 | 11 | 1733insC | Frameshift, protein truncation | 7 and 8 |
| 201 | 11 | 1733delC | Frameshift, protein truncation | 9 and 10 |
| 230 | 12 | C1844G | Tyr463X | 11 and 12 |

[a] Mutations are named according to recommendations of the Nomenclature System for Human Gene Mutations. The GenBank mRNA sequence (accession no. AF517523, SEQ ID NO: 1) of BHD is used for reference. The A of the ATG initiator codon is located at nt 456. An additional 14 of 53 families had 1733insC, 8 of 53 families had 1733delC, and 2 of 53 families had the C1844G mutations.

Fifty-three probands from small BHD families were screened for mutations in the mononucleotide $(C)_8$ tract in exon 11 of the BHD gene (FIG. 1). C insertions or deletions were found in 22 of the 53 probands, indicating that this cytosine mononucleotide tract is hypermutable and particularly prone to disease-causing mutations. In the examples disclosed herein, a total of eighteen $(C)_9$ mutations and nine $(C)_7$ mutations have been identified in 62 BHD patient samples, a $(C)_8$ tract mutation frequency of 44%. Mutations in genes with homonucleotide tracts have been reported in other human disorders, such as NF1 mutations in neurofibromatosis (Rodenhiser et al., *Mut. Res.* 373:185-195, 1997), BRCA1 mutations in breast cancer (Rodenhiser et al., *Oncogene* 12:2623-2629, 1996), and FAA mutations in Fanconi anemia (Levran et al., *Proc. Natl. Acad. Sci. USA* 94:13051-13056, 1997). In addition, mutations in a homonucleotide G tract in the PAX2 gene have been associated with renal-coloboma syndrome (Schimmenti et al., *Human Mutation* 14:369-376, 1999). Without being bound by theory, these mutations are believed to arise through a slippage-mediated mechanism during DNA replication of single base repeats resulting in expansion or contraction of the homonucleotide tract (Streisinger et al., *Symp. Quant. Biol.* 31:77-86, 1966). In all cases, these errors result in frameshift mutations leading to protein truncation.

The disclosed examples of mutations in BHD patients are predicted to truncate the protein, which leads to a loss of function of the BHD gene product, folliculin, and to the disease phenotype. If BHD was a classic tumor suppressor gene, loss of heterozygosity (LOH) would be expected to occur in renal tumors from BHD patients. Renal tumors from BHD patients were evaluated for LOH with polymorphic markers near the BHD gene. LOH was detected in 15 of 88 (17%) renal tumors from 18 BHD patients, indicating that LOH at the BHD locus is an uncommon second event leading to tumorigenesis. Alternatively, the inactivation of the second BHD allele may occur by hypermethylation. Haploinsufficiency alone may be enough to produce the BHD phenotype. Another possibility may be that the inactive BHD allele produced by germline mutations results in a dominant-negative effect leading to BHD syndrome.

cDNA from adult kidney and adult and fetal lung (Clontech) was used to amplify 3.2 kb of the BHD transcript, which was sequenced to >4-fold coverage. Separately, a putative full-length clone was obtained by screening a normal lung cDNA library (Origene Technologies, Inc.) and was also sequenced to >4-fold coverage. The full length BHD sequence of 3674 nucleotides predicted a protein, which we have named folliculin (adapted from the BHD skin lesion, fibrofolliculoma), with an open reading frame of 579 amino acids (FIG. 5B). Programs included in SEQWEB and PROSITE predicted a 64 kDa cytoplasmic protein with a glutamic acid-rich coiled-coil domain, one site of N-glycosylation and three sites of myristoylation. Although BLAST alignment against NCBI protein databases found no significant homology with any known proteins, folliculin was found to be highly conserved across mammalian species. By way of example, the mouse ortholog (SEQ ID NO: 15; MGC37841 gene product, AAH25820 protein) is 92% identical to human folliculin (SEQ ID NO: 2), illustrating the highly conserved mammalian protein sequence. The *Drosophila melanogaster* ortholog (CG8616 gene product) is 22-36% identical (44-56% positive) to the human folliculin. Finally, the *Caenorhabditis elegans* ortholog (F22D3.2 gene product, AAK31497 protein) is 27-28% identical (44-52% positive) to the human folliculin. All of these comparisons were measured by BLASTX (Altschul et al., *Nuc. Acid Res.* 25:3389-3402, 1997) and MAST (Bailey & Gribskov, *Bioinformatics* 14:48-54, 1998). The homologies across species indicate an important biological role for folliculin in a wide range of organisms.

Germline mutations in BHD orthologs that map to syntenic locations in the dog and rat may be responsible for naturally occurring inherited renal malignancies in these species, renal cystadenoma and dermatofibroma in German Shepherd dogs (Vilafranca et al., *Vet. Pathol.* 31:713-716, 1994; Jónasdóttir et al., *Proc. Nat. Acad. Sci. USA* 97:4132-4137, 2000) and an inherited renal cancer in the Nihon rat (Hino et al., *Jpn. J. Cancer. Res.* 92:1147-1149, 2001). The discovery of germline, disease-associated mutations in BHD patients with renal neoplasia and spontaneous pneumothorax underscores the importance of the BHD gene and its product, folliculin, in kidney, lung and skin organogenesis.

Example 2

BHD Consensus Sequence

A BHD nucleic acid consensus sequence is shown in SEQ ID NO: 42. The nucleic acid sequence is identical to the wild-type BHD nucleic acid sequence, with the exception of the following nucleic acids:
  (a) the M at position 1087 of the consensus sequence can be either an A or a C,
  (b) the N at position 1088 of the consensus sequence can be either a G or no nucleotide,
  (c) the N at position 1389 of the consensus sequence can be either the sequence GTGTTGCCAGAGAGTACAGAAAGCCCCT (nucleotides 1389-1416 of SEQ ID NO: 42) or no nucleotide,
  (d) the N at position 1741 of the consensus sequence can be either a C or no nucleotide,
  (e) the N at position 1742 of the consensus sequence can be either a C or no nucleotide, and
  (f) the S at position 1846 of the consensus sequence can be either a C or a G.

Example 3

Other BHD Mutations

With the provision herein of the correlation between BHD gene mutations and BHD syndrome and associated conditions, the isolation and identification of additional BHD mutations is enabled. Any conventional method for the identification of genetic mutations in a population can be used to identify such additional mutations.

For instance, existing populations (for example, mouse or human populations) are assessed for symptoms of BHD syndrome, renal neoplasia, and/or spontaneous pneumothorax, and individuals within the population are genotyped as relates to a BHD sequence. These BHD sequences are then compared to a reference BHD sequence, such as the wild-type BHD sequence (SEQ ID NO:1), to determine the presence of one or more variant nucleotide positions. Once variant nucleotides are identified, statistical analysis of the population is used to determine whether these variants are correlated with BHD syndrome and/or associated symptoms.

BHD mutations, for example, single nucleotide alterations, can be detected by a variety of techniques. The techniques used in evaluating either somatic or germline single nucleotide alterations include allele-specific oligonucleotide hybridization (ASOH) (Stoneking et al., *Am. J. Hum. Genet.* 48:370-382, 1991) which involves hybridization of probes to the sequence, stringent washing, and signal detection. Other methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect mutations in BHD DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods.

Many mutations can occur in a BHD nucleic acid or amino acid sequence that do not alter the activity of the protein. For instance, mutations can appear in a non-coding region of the nucleic acid sequence that do not affect the activity of the folliculin protein, for example in nucleic acids 1 through 455 or nucleic acids 2058 through 3674 of SEQ ID NO: 1. In addition, mutations that do not affect folliculin function can occur in unconserved regions of the BHD amino acid sequence, for example, in regions in which the human sequence (SEQ ID NO: 2) differs from the mouse sequence (SEQ ID NO: 15). These mutations are particularly unlikely to interfere with folliculin function if they are conservative substitutions. Specific, non-limiting examples of some of the regions of SEQ ID NO: 2 that can be mutated without changing protein function include: include mutating amino acid 95 to a leucine; mutating amino acid 96 to an alanine; mutating amino acid amino acid 100 to a serine; mutating amino acid 101 to a glutamine; mutating amino acid 102 to an arginine; mutating amino acid amino 105 to a tyrosine; mutating amino acid 114 to an alanine; mutating amino acid 115 to a serine; mutating amino acid 116 to a proline; mutating amino acid 120 to a valine; mutating amino acid 121 to an alanine; mutating amino acid 122 to a leucine; mutating amino acid 159 to a serine; mutating amino acid 160 to a glutamic acid; mutating amino acid 161 to an arginine; mutating amino acid 168 to a valine; mutating amino acid 169 to an alanine; mutating amino acid 170 to a leucine; mutating amino acid 200 to a serine; mutating amino acid 201 to a glutamic acid; mutating amino acid 202 to an arginine; mutating amino acid 261 to a valine; mutating amino acid 262 to an alanine; mutating amino acid 263 to a leucine; mutating amino acid 328 to an alanine; mutating amino acid 329 to a serine; mutating amino acid 330 to an asparagine; mutating amino acid 508 to an alanine; mutating amino acid 509 to a leucine; mutating amino acid 510 to an alanine; mutating amino acid 561 to an alanine; mutating amino acid 562 to an arginine; mutating amino acid 563 to a glycine; mutating amino acid 564 to an isoleucine; mutating amino acid 565 to a leucine; mutating amino acid 566 to a glutamic acid; mutating amino acid 579 to a serine; mutating amino acid 580 to a glutamic acid; mutating amino acid 581 to an arginine; mutating amino acid 591 to an alanine; mutating amino acid 593 to an alanine; mutating amino acid 600 to a proline; mutating amino acid 601 to a histidine; mutating amino acid 602 to a glutamic acid; mutating amino acid 920 to a threonine; mutating amino acid 921 to a histidine; mutating amino acid 922 to an arginine; mutating amino acid 928 to a glycine; mutating amino acid 929 to a leucine; mutating amino acid 930 to a tyrosine; mutating amino acid 931 to an alanine; mutating amino acid 932 to a leucine; mutating amino acid 933 to an alanine; mutating amino acid 952 to a serine; mutating amino acid 953 to a glutamic acid; mutating amino acid 954 to an arginine; mutating amino acid 955 to a cysteine; mutating amino acid 956 to a tyrosine; mutating amino acid 957 to a serine; mutating amino acid 960 to a threonine; mutating amino acid 961 to a histidine; mutating amino acid 962 to an arginine; mutating amino acid 972 to a proline; mutating amino acid 973 to a histidine; mutating amino acid 974 to a glutamic acid; mutating amino acid 981 to an alanine; mutating amino acid 983 to an alanine; mutating amino acid 1001 to a proline; deleting amino acid 1003; inserting a threonine following amino acid 1009; mutating amino acid 1010 to a histidine; mutating amino acid 1012 to a glycine; mutating amino acid 1013 to a leucine; mutating amino acid 1014 to a tyrosine; mutating amino acid 1124 to an asparagine; mutating amino acid 1131 to a histidine; mutating amino acid 1132 to an isoleucine; mutating amino acid 1133 to a serine; mutating amino acid 1242 to a proline; mutating amino acid 1243 to an arginine; deleting amino acid 1244; mutating amino acid 1248 to a proline; mutating amino acid 1249 to an arginine; deleting amino acid 1250; mutating amino acid 1256 to an alanine; inserting a leucine following amino acid 1256; mutating amino acid 1257 to an alanine; mutating amino acid 1258 to a histidine; mutating amino acid 1267 to an alanine; mutating amino acid 1268 to a leucine; mutating amino acid 1269 to an alanine; mutating amino acid 1279 to a valine; mutating amino acid 1280 to an alanine; mutating amino acid 1281 to a leucine; mutating amino acid 1285 to a valine; mutating amino acid 1286 to an alanine; mutating amino acid 1287 to a leucine; mutating amino acid 1300 to a threonine; mutating amino acid 1301 to a histidine; mutating amino acid 1302 to an arginine; mutating amino acid 1306 to a threonine; mutating amino acid 1307 to a histidine; mutating amino acid 1308 to an arginine; mutating amino acid 1315 to an alanine; mutating amino acid 1316 to a serine; mutating amino acid 1317 to an asparagine; mutating amino acid 1326 to an alanine; mutating amino acid 1327 to a leucine; mutating amino acid 1328 to an alanine; mutating amino acid 1483 to an isoleucine; mutating amino acid 1484 to a leucine; mutating amino acid 1485 to a glutamic acid; mutating amino acid 1581 to a valine; mutating amino acid 1582 to an arginine; mutating amino acid 1583 to a leucine; mutating amino acid 1691 to a threonine; mutating amino acid 1692 to a histidine; mutating amino acid 1703 to a serine; mutating amino acid 1704 to a glutamic acid; and mutating amino acid 1705 to an arginine.

Example 4

Clinical Uses of BHD Mutation Sequences

To perform a diagnostic test for the presence or absence of a mutation in a BHD sequence of an individual, a suitable genomic DNA-containing sample from a subject is obtained and the DNA extracted using conventional techniques. For instance, a blood sample, a buccal swab, a hair follicle preparation, or a nasal aspirate is used as a source of cells to provide the DNA sample; similarly, a surgical specimen, biopsy, or other biological sample containing genomic DNA is used. It is particularly contemplated that tumor biopsies (for instance, renal tumor samples) or tumor DNA found in plasma or other blood products can serve as a source. The extracted DNA is then subjected to in vitro amplification, for example, according to standard procedures. The allele of the single base-pair variant can be determined by conventional methods including manual and automated fluorescent DNA sequencing, primer extension methods (Nikiforov, et al., *Nucl Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single strand conformation polymorphism (SSCP), denaturing gradient gel electrophoresis (DGGE), TAQMAN® PCR, oligonucleotide hybridization, and the like. Also, see the following U.S. patents for descriptions of methods or applications of polymorphism analysis to disease prediction and/or diagnosis: U.S. Pat. No. 4,666,828 (RFLP for Huntington's); U.S. Pat. No. 4,801,531 (prediction of atherosclerosis); U.S. Pat. No. 5,110,920 (HLA typing); U.S. Pat. No. 5,268,267 (prediction of small cell carcinoma); and U.S. Pat. No. 5,387,506 (prediction of dysautonomia).

Examples of mutations associated with BHD syndrome and/or an increased likelihood of spontaneous pneumothorax and/or renal neoplasia are the mutations of BHD listed in Table 2. The absence of these mutations indicates a relatively decreased likelihood of having BHD syndrome or related symptoms, such as renal neoplasia or spontaneous pneumothorax. In addition to these particular mutations, other sequence variations that may be associated with variable predisposition to BHD or likelihood of having spontaneous pneumothorax and/or renal neoplasia can also be detected, and used in combination with the disclosed BHD mutations to predict the probability that a subject will tend to develop BHD syndrome or be likely to display spontaneous pneumothorax and/or renal neoplasia. For example, any mutation associated with abnormal expression of the folliculin protein, such as a truncation, insertion, or deletion. Such mutations are particularly likely to occur in a mutational "hot spot" that runs from nucleotides 1733 to 1740 of SEQ ID NO: 1.

The markers of the present disclosure can be utilized for the detection of, and differentiation of, individuals who are homozygous and heterozygous for BHD mutations, including the specific mutations listed in Table 2. One value of identifying individuals who carry a disease allele of BHD (for example, individuals who are heterozygous or homozygous for the an allele that contains a BHD disease mutations, such as any one of those listed in Table 2) is that these individuals can then initiate or customize therapy to reduce the occurrence of or reverse symptoms of and associated with BHD syndrome, or reduce the likelihood of developing such symptoms, or undergo more aggressive treatment of the condition, and thereby beneficially alter its course. In addition, individuals who are heterozygous or homozygous for a BHD mutation can be on the lookout for future developments that may be indicative of developing BHD or a related condition, and for instance may benefit from heightened screening for spontaneous pneumothorax, renal (or other) neoplasia, and monitoring of possible skin lesions.

Example 5

Gene Probes and Markers

Sequences surrounding and overlapping one or more mutations in the BHD gene can be useful for a number of gene mapping, targeting, and detection procedures. For example, genetic probes can be readily prepared for hybridization and detection of a BHD mutation, such as any one of those listed in Table 2. As will be appreciated, probe sequences may be greater than about 10 or more oligonucleotides in length and possess sufficient complementarity to distinguish between the C (at amino acid residue 1844 in the wildtype allele) and G (in the C1844G early truncation mutation, SEQ ID NO: 11), or between the AG at positions 1087 and 1088 (in the wildtype allele) and the C substitution at position 1087 (in the 1087delAGinsC mutation, SEQ ID NO: 3). Similarly, sequences surrounding and overlapping any of the specifically disclosed mutations (or other mutations found in accordance with the present teachings), or longer sequences encompassing more than one of the specifically disclosed mutations, can be utilized in allele specific hybridization procedures. A similar approach can be adopted to detect other BHD mutations.

Sequences surrounding and overlapping a BHD mutation, or any portion or subset thereof that allows one to identify the mutation, are highly useful. Thus, another embodiment provides a genetic marker predictive of a mutation involving at least one insertion or deletion in the $(C)_8$ mononucleotide tract at nt residues 1733 through 1740 of BHD (SEQ ID NO: 1), comprising a partial sequence of the human BHD gene including at least about 10 contiguous nucleotide residues that overlap all or a portion of the sequence at residues 1733 through 1740 of the wildtype BHD or one of the known mutation described herein (for example, 1733insC or 1733delC, SEQ ID NOs: 7 or 9, respectively).

Another specific embodiment is a genetic marker predictive of a mutation of exon 9 of BHD, comprising a partial sequence of the human BHD gene including at least about 10 contiguous nucleotide residues that overlap position 1844 of SEQ ID NO: 1, which position is indicated with the symbol "N" in the following nucleotide sequence: GAC-CAGTCTCTCAGCAAGTANGAGTTTGTG-GTGACCAGTGG (residues 1824 to 1864 of SEQ ID NO: 1), and sequences complementary therewith, wherein "N" represents G (as in the mutant sequence shown in SEQ ID NO: 11) or another single base-pair mutation of the C that is present at N in a human allele. One example mutation is a C to G transversion, but can also include a C to A transversion or C to T transition.

Likewise, another specific embodiment is a genetic marker predictive of a mutation of exon 9 of BHD, comprising a partial sequence of the human BHD-encoding sequence including at least about 10 contiguous nucleotide residues that allow the practitioner to distinguish between the wildtype sequence and a mutation in which residues 1378-1405 of the BHD sequence (SEQ ID NO: 1) are duplicated (as shown in SEQ ID NO: 5). For instance, an oligonucleotide selected from the following sequence, and sequences complementary therewith or surrounding at least a portion thereof, such that it overlaps a portion of the duplication, can be used to determine whether a sample comprises the duplication mutation:

(residues 1378 to 1433 of SEQ ID NO: 5)
AGAAAGCCCCTGTGTTGCCAGAGAGTACAGAAAGCCCCTGTGTTGCCAG
AGAGTAC.

In each embodiment, longer oligonucleotides are contemplated, that have at least 11, at least 12, at least 13, at least 14, at least 15, at least 17, at least 18, at least 20, at least 25, or more contiguous nucleotides. Specific oligonucleotides are about 30, 35, or 40 nucleotides in length, or longer. A skilled practitioner will understand how to select specific oligonucleotide sequences from the provided sequences and the guidance provided herein, in order to generate probes for determining the presence or absence of any of these markers in a biological sample from a subject, which subject includes nucleic acids from the subjects (either genomic of mRNA nucleic acids, or both).

Example 6

Detecting Nucleotide Variants/Mutations

Many of the mutations that have been detected in the BHD gene thus far have been frameshift mutations. However, mutations in this gene, such as truncation mutations, also are linked to BHD syndrome and related symptoms, such as spontaneous pneumothorax and/or renal neoplasia. The mutations at nucleotide residue 1844, or 1733, or 1087 and 1088 (numbered as in SEQ ID NO: 1), can be detected by a variety of techniques. These techniques include allele-specific oligonucleotide hybridization (ASOH) (Stoneking et al., *Am. J. Hum. Genet.* 48:370-382, 1991), which involves hybridization of probes to the sequence, stringent washing, and signal detection. Other new methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-

994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect point mutations in DNA, which will be appreciated by those of ordinary skill in the art. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods.

The nucleotide variants can also be detected using an array of nucleic acid molecules attached to a solid support, in which the array includes an oligonucleotide that hybridizes to a nucleic acid molecule that contains a mutation associated with abnormal expression of the folliculin molecule, such as the mutations shown in SEQ ID NOs: 3, 5, 7, 9, and 11. Hybridization is performed under conditions in which the oligonucleotide will hybridize to the mutant sequence but not to the wild-type sequence (SEQ ID NO: 1). Examples of patents that disclose how to make and use such arrays include U.S. Pat. Nos. 6,344,316 and 6,551,784.

Example 7

Detection of BHD Nucleic Acid Level(s)

Individuals carrying mutations in the BHD gene, or having amplifications or heterozygous or homozygous deletions of the BHD gene, may be detected at the DNA or RNA level with the use of a variety of techniques. The detection of mutations was discussed above; in the following example, techniques are provided for detecting the level of BHD nucleic acid molecules in a sample.

For such diagnostic procedures, a biological sample of the subject (an animal, such as a mouse or a human), which biological sample contains either DNA or RNA derived from the subject, is assayed for a mutated, amplified or deleted BHD encoding sequence, such as a genomic amplification of the BHD gene or an over- or under-abundance of a BHD mRNA. Suitable biological samples include samples containing genomic DNA or mRNA obtained from, for instance, subject body cells, such as those present in peripheral blood, urine, saliva, tissue biopsy, surgical specimen, amniocentesis samples and autopsy material. The detection in the biological sample of a mutant BHD gene, a mutant or truncated BHD RNA, or an amplified or homozygously or heterozygously deleted BHD gene, may be performed by a number of methodologies.

Gene dosage (copy number) can be important in disease states, and can influence mRNA and thereby protein level; it is therefore advantageous to determine the number of copies of BHD nucleic acids in samples of tissue. Probes generated from the encoding sequence of BHD (BHD probes or primers) can be used to investigate and measure genomic dosage of the BHD gene.

Techniques for measuring gene dosage are known in the art; see for instance, U.S. Pat. No. 5,569,753 ("Cancer Detection Probes") and Pinkel et al. (*Nat. Genet.* 20:207-211, 1998) ("High Resolution Analysis of DNA Copy Number Variation using Comparative Genomic Hybridization to Microarrays").

Determination of gene copy number in cells of a patient-derived sample using other techniques is known in the art. For example, BHD amplification in immortalized cell lines as well as uncultured cells taken from a subject can be carried out using bicolor FISH analysis. By way of example, interphase FISH analysis of immortalized cell lines can be carried out as previously described (Barlund et al., *Genes Chromo. Cancer* 20:372-376, 1997). The hybridizations can be evaluated using a Zeiss or other fluorescence microscope. By way of example, approximately 20 non-overlapping nuclei with intact morphology based on DAPI counterstain are scored to determine the mean number of hybridization signals for each test and reference probe.

Likewise, FISH can be performed on tissue microarrays, as described in Kononen et al. (*Nat. Med.* 4:844-847, 1998). Briefly, consecutive sections of the array are deparaffinized, dehydrated in ethanol, denatured at 74° C. for 5 minutes in 70% formamide/2×SSC, and hybridized with test and reference probes. The specimens containing tight clusters of signals or >3-fold increase in the number of test probe as compared to chromosome 17 centromere in at least 10% of the tumor cells may be considered as amplified. Microarrays using various tissues can be constructed as described in WO9944063A2 and WO9944062A1.

Overexpression of the BHD gene can also be detected by measuring the cellular level of BHD-specific mRNA. mRNA can be measured using techniques well known to those of ordinary skill in the art, including for instance Northern analysis, RT-PCR and mRNA in situ hybridization.

Example 8

Methods of Making Human BHD cDNA

The original means by which the wildtype and mutant BHD cDNAs were identified and obtained is described above. With the provision of the sequence of the folliculin proteins (SEQ ID NOs: 2, 4, 6, 8, and 12) and cDNA (SEQ ID NOs: 1, 3, 5, 7, 9, and 11), in vitro nucleic acid amplification (such as polymerase chain reaction (PCR)) now may be utilized in a simple method for producing BHD cDNA. The following example provides techniques for preparing cDNA in this manner.

Total RNA is extracted from human cells by any one of a variety of methods well known to those of ordinary skill in the art. Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992) provide descriptions of methods for RNA isolation. Because BHD is expressed in tumors and in normal tissue, human cell lines derived from tumors or normal tissue can be used as a source of such RNA. The extracted RNA is then used as a template for performing reverse transcription-polymerase chain reaction (RT-PCR) amplification of cDNA. Methods and conditions for RT-PCR are described in Kawasaki et al. (In *PCR Protocols, A Guide* to *Methods and Applications*, Innis et al. (eds.), 21-27, Academic Press, Inc., San Diego, Calif., 1990).

The selection of amplification primers will be made according to the portion(s) of the cDNA that is to be amplified. Primers may be chosen to amplify a segment of a cDNA or the entire cDNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, the portions of the human BHD cDNA molecule may be amplified using the combination of primers discussed above, in Example 1. These primers are illustrative only; one skilled in the art will appreciate that many different primers may be derived from the provided cDNA sequence in order to amplify particular regions of BHD cDNA, as well as the complete sequence of the human BHD cDNA.

Re-sequencing of PCR products obtained by these amplification procedures is advantageous to facilitate confirmation of the amplified sequence and provide information about natural variation of this sequence in different populations or species. Oligonucleotides derived from the provided BHD sequences may be used in such sequencing methods.

Orthologs of human BHD can be cloned in a similar manner, where the starting material consists of cells taken from a non-human species. Orthologs will generally share at least 20% sequence identity with the disclosed human BHD cDNA, while exhibiting substantially greater sequence identity at the protein level due to the wobble effect. Where the non-human species is more closely related to humans, the sequence identity will in general be greater. Closely related orthologous BHD molecules may share at least 70%, at least 75%, at least 80% at least 85%, at least 90%, at least 91%, at least 93%, at least 95%, or at least 98% sequence identity with the disclosed human sequences.

Oligonucleotides derived from the human BHD cDNA, or fragments of this cDNA, are encompassed within the scope of the present disclosure. Such oligonucleotides may comprise a sequence of at least 15 consecutive nucleotides of the BHD nucleic acid sequence. If these oligonucleotides are used with an in vitro amplification procedure (such as PCR), lengthening the oligonucleotides may enhance amplification specificity. Thus, oligonucleotide primers comprising at least 25, 30, 35, 40, 45, or 50 consecutive nucleotides of these sequences may be used. These primers, for instance, may be obtained from any region of the disclosed sequences. By way of example, the human BHD cDNA, ORF and gene sequences may be apportioned into about halves or quarters based on sequence length, and the isolated nucleic acid molecules (for example, oligonucleotides) may be derived from the first or second halves of the molecules, or any of the four quarters.

Nucleic acid molecules may be selected that comprise at least 15, 20, 23, 25, 30, 35, 40, 50, or 100 consecutive nucleotides of any of these or other portions of the human BHD cDNA. Thus, representative nucleic acid molecules might comprise at least 15 consecutive nucleotides of the human BHD cDNA (SEQ ID NO: 1).

Example 9

BHD Sequence Variants

With the provision of human BHD protein (folliculin) and corresponding nucleic acid sequences herein, both wildtype and various mutants, the creation of variants of these sequences is now enabled.

Variant folliculin proteins include proteins that differ in amino acid sequence from the human folliculin sequences disclosed but that share at least 60% amino acid sequence identity with the provided human folliculin protein. Other variants will share at least 75%, at least 80%, at least 85%, at least 90%, at least 95%, or at least 98% amino acid sequence identity. Manipulation of the nucleotide sequence of BHD using standard procedures, including for instance, site-directed mutagenesis or PCR, can be used to produce such variants. The simplest modifications involve the substitution of one or more amino acids for amino acids having similar biochemical properties. These conservative substitutions are likely to have minimal impact on the activity of the resultant protein. Table 3 shows amino acids that may be substituted for an original amino acid in a protein, and which are regarded as conservative substitutions.

TABLE 3

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in enzymatic function or other protein features may be obtained by selecting amino acid substitutions that are less conservative than those listed in Table 3. Such changes include changing residues that differ more significantly in their effect on maintaining polypeptide backbone structure (for example, sheet or helical conformation) near the substitution, charge or hydrophobicity of the molecule at the target site, or bulk of a specific side chain. The following substitutions are generally expected to produce the greatest changes in protein properties: (a) a hydrophilic residue (for example, seryl or threonyl) is substituted for (or by) a hydrophobic residue (for example, leucyl, isoleucyl, phenylalanyl, valyl or alanyl); (b) a cysteine or proline is substituted for (or by) any other residue; (c) a residue having an electropositive side chain (for example, lysyl, arginyl, or histadyl) is substituted for (or by) an electronegative residue (for example, glutamyl or aspartyl); or (d) a residue having a bulky side chain (for example, phenylalanine) is substituted for (or by) one lacking a side chain (for example, glycine).

Variant folliculin encoding sequences may be produced by standard DNA mutagenesis techniques, for example, M13 primer mutagenesis. Details of these techniques are provided in Sambrook et al. (In *Molecular Cloning: A Laboratory Manual*, CSHL, New York, 1989), Ch. 15. By the use of such techniques, variants may be created that differ in minor ways from the human folliculin sequences disclosed. DNA molecules and nucleotide sequences that are derivatives of those specifically disclosed herein, and which differ from those disclosed by the deletion, addition, or substitution of nucleotides while still encoding a protein that has at least 60% sequence identity with the human folliculin encoding sequence disclosed (SEQ ID NO: 1), are comprehended by this disclosure. Also comprehended are more closely related nucleic acid molecules that share at least 70%, at least 75%, at least 80%, at least 85%, at least 90%, at least 95%, or at least 98% nucleotide sequence identity with the disclosed folliculin sequences. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed human folliculin protein sequences. For example, because of the degeneracy of the genetic code, four nucleotide codon triplets—(GCT, GCG, GCC and GCA)—code for alanine. The coding sequence of any specific alanine residue within the human folliculin protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences that encode a folliculin protein, but which vary from the disclosed nucleic acid sequences by virtue of the degeneracy of the genetic code.

Variants of the folliculin protein may also be defined in terms of their sequence identity with the prototype human folliculin protein (SEQ ID NO: 2). As described above, folliculin proteins share at least 60%, at least 75%, at least 80%, at least 85%, at least 90%, at least 95%, or at least 98% amino acid sequence identity with the human folliculin protein (SEQ ID NO: 2). Nucleic acid sequences that encode such proteins/fragments readily may be determined simply by applying the genetic code to the amino acid sequence of a folliculin protein or fragment, and such nucleic acid molecules may readily be produced by assembling oligonucleotides corresponding to portions of the sequence.

Nucleic acid molecules that are derived from the human BHD cDNA nucleic acid sequences include molecules that hybridize under stringent conditions to the disclosed prototypical BHD nucleic acid molecules, or fragments thereof. In particular embodiments, the nucleic acid molecule or fragments hybridize under conditions of low stringency, high stringency, or very high stringency as defined above.

Human BHD nucleic acid encoding molecules (including the cDNA shown in SEQ ID NOs: 1, 3, 5, 7, 9, and 11, and nucleic acids comprising this sequence), and orthologs and homologs of these sequences, may be incorporated into transformation or expression vectors.

Example 10

Expression of Folliculins

The expression and purification of proteins, such as the BHD protein, folliculin, can be performed using standard laboratory techniques. After expression, purified BHD protein may be used for functional analyses, antibody production, diagnostics, and patient therapy. Furthermore, the DNA sequence of the BHD cDNA can be manipulated in studies to understand the expression of the gene and the function of its product. Mutant forms of the human BHD gene may be isolated based upon information contained herein, and may be studied in order to detect alteration in expression patterns in terms of relative quantities, tissue specificity, and functional properties of the encoded mutant BHD protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization, and functional analysis of proteins. For example, fusion proteins consisting of amino terminal peptides encoded by a portion of the *E. coli* lacZ or trpE gene linked to BHD proteins (folliculins) may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence. Similarly, fusion proteins comprising folliculin or a fragment thereof may also be generated for use as fusion proteins, depending on the peptide or protein to which the folliculin is linked. The construction and use of fusion proteins is generally known to those of ordinary skill.

Intact native protein may also be produced in *E. coli* in large amounts for functional studies. Methods and plasmid vectors for producing fusion proteins and intact native proteins in bacteria are described in Sambrook et al. (In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). BHD fusion proteins may be isolated from protein gels, lyophilized, ground into a powder, and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous BHD cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J.* 1:841, 1982), lipofection (Feigner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). BHD encoding sequences can also be delivered to target cells in vitro via non-infectious systems, for instance liposomes.

These eukaryotic expression systems can be used for studies of folliculin-encoding nucleic acids and mutant forms of these molecules, the folliculin protein, and mutant forms of this protein. Such uses include, for example, the identification of regulatory elements located in the 5' region of the BHD gene on genomic clones that can be isolated from human genomic DNA libraries using the information contained in the present disclosure. The eukaryotic expression systems may also be used to study the function of the normal complete protein, specific portions of the protein, or of naturally occurring or artificially produced mutant proteins.

Using the above techniques, the expression vectors containing the BHD gene sequence or cDNA, or fragments or variants or mutants thereof, can be introduced into human cells, mammalian cells from other species, or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The present disclosure thus encompasses recombinant vectors that comprise all or part of the BHD gene or cDNA sequences, for expression in a suitable host. The BHD DNA is operatively linked in the vector to an expression control sequence in the recombinant DNA molecule so that the folliculin polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this disclosure, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant BHD DNA sequences, similar systems are employed to express and produce the mutant product. In addition, fragments of the BHD protein can be expressed essentially as detailed above. Such fragments include individual BHD protein domains or subdomains, as well as shorter fragments such as peptides. BHD protein fragments having therapeutic properties may be expressed in this manner also.

Example 11

Production of BHD (Folliculin) Protein Specific Binding Agents

Monoclonal or polyclonal antibodies may be produced to either the normal BHD (folliculin) protein or mutant forms of this protein. For instance, antibodies may be produced that recognize a mutant BHD protein but fail to recognize a wild-type BHD protein, or which recognize a wild-type BHD protein, but fail to recognize a mutant BHD protein (see below). Optimally, antibodies raised against these proteins or peptides would specifically detect the protein or peptide with which the antibodies are generated. That is, an antibody generated to the BHD protein or a fragment thereof would recognize and bind the BHD protein and would not substantially recognize or bind to other proteins found in human cells.

The determination that an antibody specifically detects the BHD protein is made by any one of a number of standard immunoassay methods; for instance, the Western blotting technique (Sambrook et al., In *Molecular Cloning: A Laboratory Manual*, CSHL, New York, 1989). To determine that a given antibody preparation (such as one produced in a mouse) specifically detects the BHD protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the BHD protein will, by this technique, be shown to bind to the BHD protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-BHD protein binding.

Substantially pure BHD protein or protein fragment (peptide) suitable for use as an immunogen may be isolated from the transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the BHD protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein (Example 9), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the BHD protein or peptides is to use one or more synthetic peptides synthesized on a commercially available peptide synthesizer based upon the predicted amino acid sequence of the BHD protein or peptide. Polyclonal antibodies can be generated by injecting these peptides into, for instance, rabbits.

D. Antibodies Raised by Injection of BHD Encoding Sequence

Antibodies may be raised against BHD proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the BHD encoding sequence under the transcriptional control of either the human beta-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of the BHD protein.

For administration to human patients, antibodies, for example, BHD-specific monoclonal antibodies, can be humanized by methods known in the art. Antibodies with a desired binding specificity can be commercially humanized (Scotgene, Scotland, UK; Oxford Molecular, Palo Alto, Calif.).

E. Antibodies Specific for Mutant Folliculin

With the provision of several inactivating mutant folliculin proteins, the production of antibodies that specifically recognize these proteins (and peptides derived therefrom) is enabled. In particular, production of antibodies (and fragments and engineered versions thereof) that recognize at least one folliculin variant with a higher affinity than they recognize wild type folliculin is beneficial, as the resultant antibodies can be used in diagnosis and treatment, as well as in study and examination of the folliculin proteins themselves.

In particular embodiments, it is beneficial to generate antibodies from a peptide taken from a mutation or variation-specific region of the folliculin protein. By way of example, such regions include a portion or all of exon 7, exon 9, exon 11, or exon 12 of BHD protein (folliculin). More particularly, it is beneficial to raise antibodies against peptides of four or more contiguous amino acids that overlap the mutations identified in SEQ ID NO: 4, 6, 8, 10, or 12, and particularly which comprise at least four contiguous amino acids including the residue(s) shown in positions 211-221 of SEQ ID NO: 4, positions 303-397 of SEQ ID NO: 6, positions 429-454 of SEQ ID NO: 8, positions 429-466 of SEQ ID NO: 10, or position 463 of SEQ ID NO: 12.

Longer peptides also can be used, and in some instances will produce a stronger or more reliable immunogenic response. Thus, it is contemplated in some embodiments that more than 4 amino acids are used to elicit the immune response, for instance, at least 5, at least 6, at least 8, at least 10, at least 12, at least 15, at least 18, at least 20, at least 25, or more, such as 30, 40, 50, or even longer peptides. Also, it will be understood by those of ordinary skill that it is beneficial in some instances to include adjuvants and other immune response enhancers, including passenger peptides or proteins, when using peptides to induce an immune response for production of antibodies.

Embodiments are not limited to antibodies that recognize epitopes containing the actual mutation identified in each variant. Instead, it is contemplated that variant-specific antibodies also may each recognize an epitope located anywhere throughout the folliculin variant molecule, which epitopes are changed in conformation and/or availability because of the activating mutation. Antibodies directed to any of these variant-specific epitopes are also encompassed herein.

By way of example, the following references provide descriptions of methods for making antibodies specific to mutant proteins: Hills et al., (Specific targeting of a mutant, activated EGF receptor found in glioblastoma using a monoclonal antibody. *Int. J. Cancer*, 63: 537-543, 1995); Reiter & Maihle (A 1.8 kb alternative transcript from the human epidermal growth factor receptor gene encodes a truncated form of the receptor. *Nucleic Acids Res.*, 24: 4050-4056, 1996); Okamoto et al. (Monoclonal antibody against the fusion junction of a deletion-mutant epidermal growth factor receptor. *Br. J. Cancer*, 73: 1366-1372, 1996); Nakayashiki et al., (Production of a single-chain variable fragment antibody recognizing type III mutant epidermal growth factor receptor. *Jpn. J. Cancer Res.*, 91: 1035-1043, 2000); Gannon et al. (Activating mutations in p53 produce a common conformational effect. A monoclonal antibody specific for the mutant form. *EMBO J.*, 9: 1595-1602, 1990); Wong et al. (Detection of activated Mr 21,000 protein, the product of ras oncogenes, using antibodies with specificity for amino acid 12. *Cancer Res.*, 46: 6029-6033, 1986); and Carney et al. (A monoclonal antibody reactive with an activated ras protein expressing valine at position 12. *J. Cell Biochem.*, 32: 207-214, 1986). Similar methods can be employed to generate antibodies specific to specific BHD protein (folliculin) variants.

Example 12

Protein-Based Diagnosis

An alternative method of detecting BHD gene amplification, deletion or mutation, as well as abnormal BHD expression, is to quantitate the level of BHD protein (folliculin) in the cells of an individual, or to quantitate the level of truncated BHD protein and/or the full length BHD protein. This diagnostic tool would be useful for detecting reduced levels of the BHD protein that result from, for example, mutations in the promoter regions of the BHD gene or mutations within the coding region of the gene that produced truncated, non-functional or unstable polypeptides, as well as from deletions of a portion of or the entire BHD gene. Alternatively, duplications of a BHD encoding sequence may be detected as an increase in the expression level of BHD protein. Such an increase in protein expression may also be a result of an up-regulating mutation in the promoter region or other regulatory or coding sequence within the BHD gene.

Localization and/or coordinated BHD expression (temporally or spatially) can also be examined using known techniques, such as isolation and comparison of BHD from cell or tissue specific, or time specific, samples. The determination of reduced or increased BHD protein levels, in comparison to such expression in a control cell (for example, normal, as in taken from a subject not suffering from BHD syndrome or related symptoms), would be an alternative or supplemental approach to the direct determination of BHD gene deletion, amplification or mutation status by the methods disclosed herein and equivalents.

The availability of antibodies specific to the BHD protein facilitates the detection and quantitation of cellular BHD by one of a number of immunoassay methods which are well known in the art and are presented in Harlow and Lane (*Antibodies, A Laboratory Manual*, CSHL, New York, 1988). Methods of constructing such antibodies are discussed above, in Example 10.

Any standard immunoassay format (for example, ELISA, Western blot, or RIA assay) can be used to measure BHD polypeptide or protein levels and/or size; comparison is to wild-type (normal) BHD levels and/or size, and an alteration in BHD polypeptide may be indicative of an abnormal biological condition such as BHD syndrome and/or a predilection to development of spontaneous pneumothorax and/or renal neoplasia. Immunohistochemical techniques may also be utilized for BHD polypeptide or protein detection. For example, a tissue sample may be obtained from a subject, and a section stained for the presence of BHD using a BHD-specific binding agent (for example, anti-BHD antibody) and any standard detection system (for example, one which includes a secondary antibody conjugated to horseradish peroxidase). General guidance regarding such techniques can be found in, for example, Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating a BHD protein, a biological sample of the subject (which can be any animal, for instance, a mouse or a human), which sample includes cellular proteins, is used. Such a biological sample may be obtained from body cells, such as those present in peripheral blood, urine, saliva, tissue biopsy, amniocentesis samples, surgical specimens and autopsy material, particularly breast cells. Quantitation of BHD protein can be achieved by immunoassay and compared to levels of the protein found in control cells (for example, healthy, as in from a subject known not to have BHD syndrome or related symptoms). A significant (for example, 10% or greater) reduction in the amount of BHD protein in the cells of a subject compared to the amount of BHD protein found in normal human cells could be taken as an indication that the subject may have deletions or mutations in the BHD gene, whereas a significant (for example, 10% or greater) increase would indicate that a duplication (amplification), or mutation that increases the stability of the BHD protein or mRNA, may have occurred. Deletion, mutation, and/or amplification of or within the BHD encoding sequence, and substantial under- or over-expression of BHD protein, is indicative of BHD syndrome and/or a predilection to develop spontaneous pneumothorax and/or renal neoplasia.

Example 13

Differentiation of Individuals Homozygous Versus Heterozygous for BHD Mutation(s)

As will be appreciated, the oligonucleotide ligation assay (OLA), as described at Nickerson et al. (*Proc. Natl. Acad. Sci. USA* 87:8923-8927, 1990), allows the differentiation between individuals who are homozygous versus heterozygous for specific BHD mutations, such as for instance those mutations listed in Table 3. This feature allows one to rapidly and easily determine whether an individual is homozygous for at least one BHD mutation, which mutation is linked to BHD and/or a relatively high predisposition to developing BHD syndrome and/or an increased likelihood of experiencing spontaneous pneumothorax and/or developing renal neoplasia. Alternatively, OLA can be used to determine whether a subject is homozygous for any of these mutations.

As an example of the OLA assay, when carried out in microtiter plates, one well is used for the determination of the presence of the BHD allele that contains a C at nucleotide position 1844 and a second well is used for the determination of the presence of the BHD allele that contains a G at nucleotide position 1844. Thus, the results for an individual who is heterozygous for the C1844G mutation will show a signal in each of the C and G wells, and an individual who is homozygous for the mutant C1844G mutation will show a signal in only the G well. A skilled practitioner will understand how to design other oligonucleotides for other OLA assays to be used in detecting the several mutations described herein, as well as others identified based on the specific disclosed mutations.

Example 14

Suppression of BHD Protein Expression

A reduction of BHD protein expression in a transgenic cell may be obtained by introducing into cells an antisense construct based on the BHD encoding sequence, including the human BHD cDNA (Accession number AF517523; SEQ ID NO: 1) or gene sequence or flanking regions thereof. For antisense suppression, a nucleotide sequence from a BHD encoding sequence, for example, all or a portion of the BHD cDNA or gene, is arranged in reverse orientation relative to the promoter sequence in the transformation vector. Other aspects of the vector may be chosen as discussed above (Example 9).

The introduced sequence need not be the full length human BHD cDNA or gene or reverse complement thereof, and need not be exactly homologous to the equivalent sequence found in the cell type to be transformed. Generally, however, where the introduced sequence is of shorter length, a higher degree of homology to the native BHD sequence will be needed for effective antisense suppression. The introduced antisense sequence in the vector may be at least 30 nucleotides in length, and improved antisense suppression will typically be observed as the length of the antisense sequence increases. The length of the antisense sequence in the vector advantageously may be greater than 100 nucleotides. For suppression of the BHD gene itself, transcription of an antisense construct results in the production of RNA molecules that are the reverse complement of mRNA molecules transcribed from the endogenous BHD gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous BHD expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. Several models have been put forward to explain RNAi, in particular the mechanisms by which the cleavage derived small dsRNAs or siRNAs interact with the target mRNA and thus facilitate its degradation (Hamilton et al., *Science* 286, 950, 1999; Zamore et al., *Cell* 101, 25, 2000; Hammond et al., *Nature* 404, 293, 2000; Yang et al., *Curr. Biol.* 10, 1191, 2000; Elbashir et al., *Genes Dev.* 15, 188, 2001; Bass *Cell* 101, 235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of ~21-23 nts in the region corresponding to the input dsRNA (Zamore et al., *Cell* 101, 25, 2000), with the exact cleavage sites corresponding to the middle of sequences covered by individual 21- or 22 nt small dsRNAS or siRNAs (Elbashir et al., *Genes Dev.* 15, 188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well-known genetic engineering techniques to produce dsRNAs. Double stranded RNA triggers could also be expressed from DNA based vector systems.

Finally, dominant negative mutant forms of BHD may be used to block endogenous BHD activity.

Example 15

BHD Gene Therapy

Gene therapy approaches for combating BHD syndrome and associated symptoms, or reducing the risk of developing spontaneous pneumothorax and/or renal neoplasia, in subjects are now made possible by the present disclosure.

Retroviruses have been considered a preferred vector for experiments in gene therapy, with a high efficiency of infection and stable integration and expression (Orkin et al., *Prog. Med. Genet.* 7:130-142, 1988). The full-length BHD gene or cDNA can be cloned into a retroviral vector and driven from either its endogenous promoter or from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

Recent developments in gene therapy techniques include the use of RNA-DNA hybrid oligonucleotides, as described by Cole-Strauss, et al. (*Science* 273:1386-1389, 1996). This technique may allow for site-specific integration of cloned sequences, thereby permitting accurately targeted gene replacement.

In addition to delivery of a BHD-encoding sequence to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

To reduce the level of BHD expression, gene therapy can be carried out using antisense or other suppressive constructs, the construction of which is discussed above (Example 13).

Example 16

Incorporation of Folliculin Protein into Pharmaceutical Compositions

Pharmaceutical compositions that comprise at least one folliculin protein or fragment thereof as an active ingredient will normally be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example, sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (for example, syrups, solutions or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise folliculin protein will preferably be formulated in unit dosage form, suitable for individual administration of precise dosages. One possible unit dosage contains approximately 100 µg of protein. The amount of active compound administered will be dependent on the subject being treated, the severity of the affliction, and the manner of administration, and is best left to the judgment of the prescribing clinician. Within these bounds, the formulation to be administered will contain a quantity of the active component(s) in an amount effective to achieve the desired effect in the subject being treated.

Example 17

Kits

Kits are provided which contain the necessary reagents for determining the presence or absence of mutation(s) in a BHD-encoding sequence, such as probes or primers specific for the BHD gene. Such kits can be used with the methods described herein to determine whether a subject is predisposed to BHD syndrome and/or spontaneous pneumothorax and/or renal neoplasia.

The provided kits may also include written instructions. The instructions can provide calibration curves or charts to compare with the determined (for example, experimentally measured) values. Kits are also provided to determine elevated or depressed expression of mRNA (for example, containing probes) or BHD protein (for example, containing antibodies or other folliculin specific binding agents).

A. Kits for Amplification of BHD Sequences

The nucleic acid molecules disclosed herein, and oligonucleotide probes and primers derived therefrom, can be supplied in the form of a kit for use in detection of a predisposition to BHD syndrome or spontaneous pneumothorax and/or renal neoplasia in a subject. In such a kit, an appropriate amount of one or more of the oligonucleotide primers is provided in one or more containers. Oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of a BHD mutation can be added to the individual tubes and amplification carried out directly.

The amount of each oligonucleotide primer supplied in the kit can be any appropriate amount, depending, for instance, on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may, for instance, be found in Innis et al. (PCR Protocols, A Guide to Methods and Applications, Academic Press, Inc., San Diego, Calif., 1990), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

A kit may include more than two primers, in order to facilitate the in vitro amplification of BHD sequences, for instance the BHD gene or the 5' or 3' flanking region thereof.

In some embodiments, kits may also include the reagents necessary to carry out nucleotide amplification reactions, including, for instance, DNA sample preparation reagents, appropriate buffers (for example, polymerase buffer), salts (for example, magnesium chloride), and deoxyribonucleotides (dNTPs).

Kits may in addition include either labeled or unlabeled oligonucleotide probes for use in detection of BHD mutation(s). In certain embodiments, these probes will be specific for a potential mutation that may be present in the target-amplified sequences. The appropriate sequences for such a probe will be any sequence that includes one or more of the identified mutant sites, particularly nucleotide positions (numbered as in SEQ ID NO: 1 unless otherwise stated) 1087 and/or 1088, all or a portion of positions 1378-1405 (or 1378-1405 of SEQ ID NO: 5), 1733 through 1741, and 1844, such that the sequence of the probe is complementary to a mutant site and the surrounding BHD sequence.

It may also be advantageous to provide in the kit one or more control sequences for use in the amplification reactions. The design of appropriate positive control sequences is well known to one of ordinary skill in the appropriate art.

B. Kits for Detection of BHD mRNA Expression

Kits similar to those disclosed above for the detection of BHD mutations directly can be used to detect BHD mRNA expression, such as over- or under-expression. Such kits include an appropriate amount of one or more oligonucleotide primers for use in, for instance, reverse transcription PCR reactions, similarly to those provided above with art-obvious modifications for use with RNA amplification.

In some embodiments, kits for detection of altered expression of BHD mRNA may also include some or all of the reagents necessary to carry out RT-PCR in vitro amplification reactions, including, for instance, RNA sample preparation reagents (including, for example, an RNase inhibitor), appropriate buffers (for example, polymerase buffer), salts (for example, magnesium chloride), and deoxyribonucleotides (dNTPs). Written instructions may also be included.

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential mutation that may be present in the target amplified sequences, for instance specific for the 1087delAGinsC allele (for example, capable of detecting a C residue at position 1087 of the BHD sequence instead of the AG that is found in wildtype). Other embodiment kits include probes specific for the 1378 through 1405 duplication mutation, the 1733insC and 1733delC frameshift mutations, and the C1844G premature termination mutation.

It may also be advantageous to provide in the kit one or more control sequences for use in the RT-PCR reactions. The design of appropriate positive control sequences is well known to one of ordinary skill in the appropriate art.

Alternatively, kits may be provided with the necessary reagents to carry out quantitative or semi-quantitative Northern analysis of BHD mRNA. Such kits include, for instance, at least one BHD-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme. In certain embodiments, such probes will be specific for a potential mutation that may be present in the target amplified sequences, for instance, specific for the 1087delAGinsC allele (for example, capable of detecting a C residue at position 1087 of the BHD sequence instead of the AG that is found in wildtype). Other embodiment kits include probes specific for the 1378 through 1405 duplication mutation, the 1733insC and 1733delC frameshift mutations, and the C1844G premature termination mutation.

C. Kits for Detection of BHD (Folliculin) Protein Expression

Kits for the detection of BHD protein expression (such as over- or under-expression) are also encompassed. Such kits may include at least one target protein specific binding agent (for example, a polyclonal or monoclonal antibody or antibody fragment that specifically recognizes the BHD protein, folliculin) and may include at least one control (such as a determined amount of BHD protein, or a sample containing a determined amount of BHD protein). The folliculin-protein specific binding agent and control may be contained in separate containers.

BHD protein expression detection kits may also include a means for detecting BHD:binding agent complexes, for instance, the agent may be detectably labeled. If the detectable agent is not labeled, it may be detected by second antibodies or protein A, for example, which may also be provided in some kits in one or more separate containers. Such techniques are well known.

Additional components in specific kits may include instructions for carrying out the assay. Instructions will allow the tester to determine whether BHD expression levels are elevated. Reaction vessels and auxiliary reagents such as chromogens, buffers, enzymes, etc. may also be included in the kits.

D. Kits for Detection of Homozygous Versus Heterozygous Allelism

Also provided are kits that allow differentiation between individuals who are homozygous versus heterozygous for the 1087delAGinsC, 1378→1405 dup, a 1733insC or 1733delC, or the C1844G mutations of BHD. Such kits provide the materials necessary to perform oligonucleotide ligation assays (OLA), as described by Nickerson et al. (*Proc. Natl. Acad. Sci. USA* 87:8923-8927, 1990) and herein. In specific embodiments, these kits contain one or more microtiter plate assays, designed to detect mutation(s) in the BHD sequence of a subject, as described herein.

Additional components in some of these kits may include instructions for carrying out the assay. Instructions will allow the tester to determine whether a BHD allele is homozygous or heterozygous. Reaction vessels and auxiliary reagents such as chromogens, buffers, enzymes, etc. may also be included in the kits.

It may also be advantageous to provide in the kit one or more control sequences for use in the OLA reactions. The design of appropriate positive control sequences is well known to one of ordinary skill in the appropriate art.

Example 18

BHD Knockout and Overexpression Transgenic Animals

Mutant organisms that under-express or over-express the BHD protein folliculin are useful for research, for instance.

Such mutants allow insight into the physiological and/or pathological role of BHD in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." For example, a non-BHD promoter inserted upstream of a native BHD-encoding sequence would be non-native. An extra copy of a BHD gene on a plasmid, transformed into a cell, would be non-native.

Mutants may be, for example, produced from mammals, such as mice, that either over-express folliculin or under-express folliculin, or that do not express folliculin at all. Over-expression mutants are made by increasing the number of BHD genes in the organism, or by introducing a BHD gene into the organism under the control of a constitutive or inducible or viral promoter such as the mouse mammary tumor virus (MMTV) promoter or the whey acidic protein (WAP) promoter or the metallothionein promoter. Mutants that under-express folliculin may be made by using an inducible or repressible promoter, or by deleting the BHD gene, or by destroying or limiting the function of the BHD gene, for instance by disrupting the gene by transposon insertion.

Antisense genes may be engineered into the organism, under a constitutive or inducible promoter, to decrease or prevent folliculin expression, as discussed above in Example 11.

A gene is "functionally deleted" when genetic engineering has been used to negate or reduce gene expression to negligible levels. When a mutant is referred to in this application as having the BHD gene altered or functionally deleted, this refers to the BHD gene and to any ortholog of this gene. When a mutant is referred to as having "more than the normal copy number" of a gene, this means that it has more than the usual number of genes found in the wild-type organism, for example, in the diploid mouse or human.

A mutant mouse or other mammal over-expressing folliculin may be made by constructing a plasmid having a BHD encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland, and lymphoid tissues. Many other promoters might be used to achieve various patterns of expression, for example, the metallothionein promoter.

An inducible system may be created in which the subject expression construct is driven by a promoter regulated by an agent that can be fed to the mouse, such as tetracycline. Such techniques are well known in the art.

A mutant knockout animal (for example, mouse) from which a BHD gene is deleted can be made by removing all or some of the coding regions of the BHD gene from embryonic stem cells. The methods of creating deletion mutations by using a targeting vector have been described (Thomas and Capecch, Cell 51:503-512, 1987).

A mutant knockout animal (for example, mouse) can be made by conditional BHD gene targeting using Cre/lox site-specific recombination technology and deleting the BHD gene in a tissue-(for example, skin) or time-dependent manner.

Example 19

Knock-in Organisms

In addition to knock-out systems, it is also beneficial to generate "knock-ins" that have lost expression of the wild-type protein but have gained expression of a different, usually mutant form of the same protein. By way of example, the mutant BHD proteins (folliculins) provided herein (for example, in SEQ ID NO: 4, 6, 8, 10, and 12) can be expressed in a knockout background in order to provide model systems for studying the effects of these mutants. In particular embodiments, the resultant knock-in organisms provide systems for studying neoplasia, such as renal neoplasia.

Those of ordinary skill in the relevant art know methods of producing knock-in organisms. See, for instance, Rane et al. (Germ line transmission of the Cdk4(R24C) mutation facilitates tumorigenesis and escape from cellular senescence. *Mol. Cell Biol.*, 22: 644-656, 2002); Sotillo et al. (Wide spectrum of tumors in knock-in mice carrying a Cdk4 protein insensitive to INK4 inhibitors. *EMBO J.*, 20: 6637-6647, 2001); Luo et al. (Knock-in mice with a chimeric human/murine p53 gene develop normally and show wild-type p53 responses to DNA damaging agents: a new biomedical research tool. *Oncogene*, 20: 320-328, 2001); Tomasson et al. (TEL/PDGFbetaR induces hematologic malignancies in mice that respond to a specific tyrosine kinase inhibitor. *Blood*, 93: 1707-1714, 1999); Voncken et al. (BCR/ABL P210 and P190 cause distinct leukemia in transgenic mice. *Blood*, 86: 4603-4611, 1995); Andrae et al. (A 1.8 kb GFAP-promoter fragment is active in specific regions of the embryonic CNS. *Mech. Dev.*, 107: 181-185, 2001); Reinertsen et al. (Temporal and spatial specificity of PDGF alpha receptor promoter in transgenic mice. *Gene Expr.*, 6: 301-314, 1997); Huang et al. (Expression of green fluorescent protein in oligodendrocytes in a time- and level-controllable fashion with a tetracycline-regulated system. *Mol. Med.*, 5: 129-137, 1999); Reichert et al. (Treatment of Bcr/Abl-positive acute lymphoblastic leukemia in P190 transgenic mice with the farnesyl transferase inhibitor SCH66336. *Blood*, 97: 1399-1403, 2001); and Huettner et al. (Reversibility of acute B-cell leukaemia induced by BCR-ABL1. *Nat. Genet.*, 24: 57-60, 2000), by way of example.

Example 20

Detection of Folliculin-Interacting Proteins

With the provision herein of the folliculin protein, and its link to BHD syndrome, methods of identifying proteins that interact with folliculin are now enabled. The identification and study of such proteins will help to characterize native and mutant functions of the folliculin proteins, and thus will contribute significantly understanding the native biology of the protein as well as its contribution to BHD syndrome and associated conditions.

There are many systems for the identification of protein-protein interactions, which systems will be known to those of ordinary skill in the art. Merely by way of example, the yeast two hybrid system (Song and Field, *Nature* 340(6230):245-246, 1989) and later developed systems can be used to identify proteins that interact with folliculin or fragments or domains thereof. For a review of applications of the yeast two hybrid system, see Gietz et al., ("Identification of proteins that interact with a protein of interest: Applications of the yeast two-hybrid system." *Mol. Cell Biochem.* 172:67-79, 1997). Systems for identifying protein-protein interactions are also described in the following patent documents: U.S. Pat. No. 5,637,463 "Methods to detect protein-protein interactions"; U.S. Pat. No. 5,925,523 "Interaction trap assay, reagents, and uses thereof"; U.S. Pat. No. 5,928,868 "Three hybrid screening assay"; U.S. Pat. No. 5,955,280 "Reverse two-hybrid system"; U.S. Pat. No. 5,965,368 "Reverse two-hybrid system"; U.S. Pat. No. 6,200,759 "Interaction trap assay, reagents, and uses thereof"; and U.S. Pat. No. 6,342,345 "Detection of molecular interactions by reporter subunit complementation"

Merely by way of example, the HYBRID HUNTER™ yeast two-hybrid system from Invitrogen (Carlsbad, Calif.) can be used to screen a human cDNA library for folliculin-binding or interacting proteins. Bait plasmids are generated by PCR cloning full-length BHD encoding sequence or a portion thereof in-frame with the DNA-binding domain of LexA from the pHybLex/Zeo. The prey plasmid library can be generated by cloning a human cDNA library downstream of the B42 activator domain in the pYESTrp2 vector.

Bait plasmid is transformed into a yeast strain, such as L40 [MATa his3Δ200 trp1-901 leu2-3112 ade2 LYS2::(4lexAop-HIS3) URA3::(8lexAop-lacZ) GAL4] (Invitrogen, Carlsbad, Calif.) using the PEG/Li-acetate (Gietz et al., *Nucleic Acids Res.* 20:1425, 1992) or another standard method. The cDNA library is then transformed into these cells. Transformants growing on his⁻ media are tested using a β-galactosidase filter lift assay (Invitrogen, Carlsbad, Calif.). Putative positive clones are indicated by blue colonies after 25 minutes in the 30° C. incubator. Putative positive clones are selected for further testing. Plasmid DNA extracted from the clones can be transformed into *E. coli* XL10-gold cells (Stratagene, La Jolla, Calif.), and then subjected to restriction analysis and/or sequence analysis. Each putative interactor can be checked for autoactivation and histidine prototrophy. Additional analysis using standard techniques can be performed to test for and eliminate false positives.

In addition to the HYBRID HUNTER™ two-hybrid system, commercial two-hybrid systems are also available from other sources, including the MATCHMAKER™ LexA two-hybrid system from Clontech (Mountain View, Calif.), the DUPLEX-A™ two-hybrid system from OriGene Technologies, Inc. (Rockville, Md.), and the DISPLAYGREEN™ Two-Hybrid Kit from Display Systems Biotech (Vista, Calif.).

Another method of identification of folliculin binding proteins is by GST-folliculin pull down assays (Kaelin et al., *Cell* 70:351, 1992). Another method is the use of peptide phage display technology (Sche et al., *Chemistry & Biology* 6:707, 1999).

This disclosure provides a new nucleic acid molecule, BHD, and the protein encoded thereby (folliculin), along with several specific mutant BHD sequences and folliculin proteins that are linked to BHD syndrome, and more particularly to predisposition to or the condition of spontaneous pneumothorax and/or renal neoplasia. The disclosure further provides methods for identifying these mutations or mutant proteins in a subject, and using them to determine or predict a subject's BHD disease state. It will be apparent that the precise details of the methods described may be varied or modified without departing from the spirit of the described disclosure. We claim all such modifications and variations that fall within the scope and spirit of the claims below.

We claim:

1. An isolated cDNA molecule consisting of a nucleic acid sequence encoding a polypeptide:
   having an amino acid sequence consisting of the sequence of SEQ ID NO: 2;
   having an amino acid sequence consisting of a sequence having at least 95% sequence identity to the sequence of SEQ ID NO: 2;
   wherein the isolated cDNA molecule hybridizes with a nucleic acid probe comprising the sequence shown in SEQ ID NO: 1 under wash conditions of 55° C., 1.0×SSC for 20 minutes.

2. The isolated cDNA molecule of claim 1, wherein the isolated nucleic acid molecule hybridizes with a nucleic acid probe comprising the sequence shown in SEQ ID NO: 1 under wash conditions of 55° C., 0.2×SSC for 30 minutes.

3. An isolated single-stranded oligonucleotide comprising a fragment of SEQ ID NO: 3, 5, 7, 9, or 11 or the reverse complement thereof, consisting of:
   at least 30 contiguous nucleotides that overlap position 1087 of SEQ ID NO: 3 ;
   at least 100 contiguous nucleotides that overlap the duplication of positions 1378-1405 of SEQ ID NO: 5;
   at least 30 contiguous nucleotides that comprise the mononucleotide $(C)_8$ tract at positions 1733-1740 of SEQ ID NO: 7 and the 1733insC frameshift mutation of SEQ ID NO: 7;
   at least 40 contiguous nucleotides of SEQ ID NO: 9 comprising the 1733delC cytosine deletion mutation within the mononucleotide $(C)_8$ tract corresponding to positions 1733-1740 of SEQ ID NO: 1; or
   at least 30 contiguous nucleotides that overlap position 1844 of SEQ ID NO: 11, wherein the oligonucleotide is labeled with a radioactive isotope, a chemiluminescent or fluorescent agent, a hapten, or an enzyme.

4. A kit for detecting a BHD mutation, comprising at least one oligonucleotide of claim 3.

5. A kit for detection of a genetic mutation in a sample of nucleic acid, comprising:
   a first container containing the oligonucleotide of claim 3; and
   a second container containing a labeled nucleic acid probe that is complementary to the oligonucleotide.

6. The kit of claim 5, wherein the labeled nucleic acid probe has a length of between 30 and 500 nucleotides.

7. An array of nucleic acid molecules attached to a solid support, the array comprising the oligonucleotide of claim 3.

8. The isolated single-stranded oligonucleotide fragment of claim 3, consisting of:
   at least 30 contiguous nucleotides that overlap position 1087 of SEQ ID NO: 3 ;
   at least 100 contiguous nucleotides that comprise positions 1378-1433 of SEQ ID NO: 5;
   at least 30 contiguous nucleotides that comprise the mononucleotide $(C)_8$ tract at positions 1733-1740 of SEQ ID NO: 7 and the 1733insC frameshift mutation of SEQ ID NO: 7;
   at least 40 contiguous nucleotides of SEQ ID NO: 9 comprising the 1733delC cytosine deletion mutation within the mononucleotide $(C)_8$ tract corresponding to positions 1733-1740 of SEQ ID NO: 1; or at least 30 contiguous nucleotides that overlap position 1844 of SEQ ID NO: 11.

9. The isolated single-stranded oligonucleotide fragment of claim 3, consisting of:

at least 40 contiguous nucleotides that overlap position 1087 of SEQ ID NO: 3;

at least 200 contiguous nucleotides that overlap the duplication of positions 1378-1405 of SEQ ID NO: 5;

at least 40 contiguous nucleotides that comprise the mononucleotide $(C)_8$ tract at positions 1733-1740 of SEQ ID NO: 7 and the 1733insC frameshift mutation of SEQ ID NO: 7;

at least 40 contiguous nucleotides of SEQ ID NO: 9 comprising 1733delC cytosine deletion mutation within the mononucleotide $(C)_8$ tract corresponding to positions 1733-1740 of SEQ ID NO: 1; or at least 40 contiguous nucleotides that overlap position 1844 of SEQ ID NO: 11.

10. The isolated single-stranded oligonucleotide fragment of claim 9, consisting of:

at least 50 contiguous nucleotides that overlap position 1087 of SEQ ID NO: 3 ;

at least 50 contiguous nucleotides that comprise the mononucleotide $(C)_8$ tract at positions 1733-1740 of SEQ ID NO: 7 and the 1733insC frameshift mutation of SEQ ID NO: 7;

at least 50 contiguous nucleotides of SEQ ID NO: 9 comprising 1733delC cytosine deletion mutation within the mononucleotide $(C)_8$ tract corresponding to positions 1733-1740 of SEQ ID NO: 1; or at least 50 contiguous nucleotides that overlap position 1844 of SEQ ID NO: 11.

11. An isolated cDNA molecule comprising the sequence of SEQ ID NO: 42.

* * * * *

SEQUENCE LISTING

```
<160> NUMBER OF SEQ ID NOS: 42

<210> SEQ ID NO 1
<211> LENGTH: 3674
<212> TYPE: DNA
<213> ORGANISM: Homo sapiens
<220> FEATURE:
<221> NAME/KEY: CDS
<222> LOCATION: (456)..(2195)

<400> SEQUENCE: 1
ggtcgctcct ggttctgcca gctccctga gagcctgaac ccgggcttga gagcctcgcc      60
accccgggtg acatccctgc cgtgggcttg ggggctctgg gtgtgattcc gccggtccgg     120
gtcccgcagc gaccacctac ccagcgcagt caggggtggg gctgggaccc agagcgggac    180
cccggctgcc gagtccaggt gtcccgcggg cctcgatttg gggagcagaa aacgccaggt    240
cttcaagggt gtctgccacc accatgcctg acccatttgg cagcagcctc gtgtgtggtg    300
gtctggtgtg gacggtggaa gcgtgattct gctgagtgtc agtgtgacca ctcgtgctca    360
gccgtatctc agcaggagga caggtgccgg agcagctcgt gcagctaagc agccaactgc    420
agaaacgtca ggcctgttgc agtctccaag gcacc atg aat gcc atc gtg gct       473
                                     Met Asn Ala Ile Val Ala
                                       1               5 ctc tgc cac ttc tgc gag ctc cac ggc ccc cgc act ctc ttc tgc acg     521
Leu Cys His Phe Cys Glu Leu His Gly Pro Arg Thr Leu Phe Cys Thr
             10                  15                  20 gag gtg ctg cac gcc cca ctt cct caa ggg gat ggg aat gag gac agt     569
Glu Val Leu His Ala Pro Leu Pro Gln Gly Asp Gly Asn Glu Asp Ser
         25                  30                  35
```

```
cct ggc cag ggt gag cag gcg gaa gaa gag gaa ggt ggc att cag atg      617
Pro Gly Gln Gly Glu Gln Ala Glu Glu Glu Glu Gly Gly Ile Gln Met
    40                  45                  50 aac agt cgg atg cgt gcg cac agc ccc gca gag ggg gcc agc gtc gag      665
Asn Ser Arg Met Arg Ala His Ser Pro Ala Glu Gly Ala Ser Val Glu
55                  60                  65                  70 tcc agc agc ccg ggg ccc aaa aag tcg gac atg tgc gag ggc tgc cgg      713
Ser Ser Ser Pro Gly Pro Lys Lys Ser Asp Met Cys Glu Gly Cys Arg
                75                  80                  85 tca ctt gct gca ggg cac ccg gga tat atc agc cat gat aaa gag acc      761
Ser Leu Ala Ala Gly His Pro Gly Tyr Ile Ser His Asp Lys Glu Thr
        90                  95                  100 tcc att aaa tac gtc agc cac cag cac ccc agc cac ccc cag ctc ttc      809
Ser Ile Lys Tyr Val Ser His Gln His Pro Ser His Pro Gln Leu Phe
            105                 110                 115 agc att gtc cgc cag gcc tgt gtc cgg agc ctg agc tgt gag gtc tgc      857
Ser Ile Val Arg Gln Ala Cys Val Arg Ser Leu Ser Cys Glu Val Cys
    120                 125                 130 cct ggc cgt gaa ggc ccc atc ttc ttc gga gat gag cag cac ggc ttt      905
Pro Gly Arg Glu Gly Pro Ile Phe Phe Gly Asp Glu Gln His Gly Phe
135                 140                 145                 150 gtg ttc agc cac acc ttc ttc atc aag gac agc ctg gcc agg ggc ttc      953
Val Phe Ser His Thr Phe Phe Ile Lys Asp Ser Leu Ala Arg Gly Phe
                155                 160                 165 cag cgc tgg tac agc atc atc acc atc atg atg gac cgg atc tac ctc     1001
Gln Arg Trp Tyr Ser Ile Ile Thr Ile Met Met Asp Arg Ile Tyr Leu
        170                 175                 180 atc aac tcc tgg ccc ttc ctg ctg ggg aag gtc cgg gga atc atc gat     1049
Ile Asn Ser Trp Pro Phe Leu Leu Gly Lys Val Arg Gly Ile Ile Asp
            185                 190                 195 gag ctc cag ggc aag gcg ctc aag gtg ttt gag gca gag cag ttt gga     1097
Glu Leu Gln Gly Lys Ala Leu Lys Val Phe Glu Ala Glu Gln Phe Gly
    200                 205                 210 tgc cca cag cgt gct cag agg atg aac aca gcc ttc acg cca ttc cta     1145
Cys Pro Gln Arg Ala Gln Arg Met Asn Thr Ala Phe Thr Pro Phe Leu
215                 220                 225                 230 cac cag agg aac ggc aac gcc gcc cgc tcg ctg aca tcg ctg aca agt     1193
His Gln Arg Asn Gly Asn Ala Ala Arg Ser Leu Thr Ser Leu Thr Ser
                235                 240                 245 gat gac aac ctg tgg gcg tgc ctg cac acc tcc ttt gcc tgg ctc ctg     1241
Asp Asp Asn Leu Trp Ala Cys Leu His Thr Ser Phe Ala Trp Leu Leu
        250                 255                 260 aag gcg tgt ggc agc cgg ctg acc gag aag ctc ctg gaa ggt gct ccg     1289
Lys Ala Cys Gly Ser Arg Leu Thr Glu Lys Leu Leu Glu Gly Ala Pro
            265                 270                 275 acc gag gat acc ttg gtc cag atg gag aag ctc gct gat tta gaa gag     1337
Thr Glu Asp Thr Leu Val Gln Met Glu Lys Leu Ala Asp Leu Glu Glu
    280                 285                 290 gaa tca gaa agc tgg gac aac tct gag gct gaa gag gag gag aaa gcc     1385
Glu Ser Glu Ser Trp Asp Asn Ser Glu Ala Glu Glu Glu Glu Lys Ala
295                 300                 305                 310 cct gtg ttg cca gag agt aca gaa ggg cgg gag ctg acc cag ggc ccg     1433
Pro Val Leu Pro Glu Ser Thr Glu Gly Arg Glu Leu Thr Gln Gly Pro
                315                 320                 325 gca gag tcc tcc tct ctc tca ggc tgt ggg agc tgg cag ccc cgg aag     1481
Ala Glu Ser Ser Ser Leu Ser Gly Cys Gly Ser Trp Gln Pro Arg Lys
        330                 335                 340 ctg cca gtc ttc aag tcc ctc cgg cac atg agg cag gtc ctg ggt gcc     1529
Leu Pro Val Phe Lys Ser Leu Arg His Met Arg Gln Val Leu Gly Ala
            345                 350                 355
```

```
cct tct ttc cgc atg ctg gcc tgg cac gtt ctc atg ggg aac cag gtg    1577
Pro Ser Phe Arg Met Leu Ala Trp His Val Leu Met Gly Asn Gln Val
    360                 365                 370 atc tgg aaa agc aga gac gtg gac ctc gtc cag tca gct ttt gaa gta    1625
Ile Trp Lys Ser Arg Asp Val Asp Leu Val Gln Ser Ala Phe Glu Val
375                 380                 385                 390 ctt cgg acc atg ctt ccc gtg ggc tgc gtc cgc atc atc cca tac agc    1673
Leu Arg Thr Met Leu Pro Val Gly Cys Val Arg Ile Ile Pro Tyr Ser
                395                 400                 405 agc cag tac gag gag gcc tat cgg tgc aac ttc ctg ggg ctc agc ccg    1721
Ser Gln Tyr Glu Glu Ala Tyr Arg Cys Asn Phe Leu Gly Leu Ser Pro
            410                 415                 420 cac gtg cag atc ccc ccc cac gtg ctc tcc tca gag ttt gct gtc atc    1769
His Val Gln Ile Pro Pro His Val Leu Ser Ser Glu Phe Ala Val Ile
        425                 430                 435 gtg gag gtc cac gca gcc gca cgt tcc acc ctc cac cct gtg ggg tgt    1817
Val Glu Val His Ala Ala Ala Arg Ser Thr Leu His Pro Val Gly Cys
    440                 445                 450 gag gat gac cag tct ctc agc aag tac gag ttt gtg gtg acc agt ggg    1865
Glu Asp Asp Gln Ser Leu Ser Lys Tyr Glu Phe Val Val Thr Ser Gly
455                 460                 465                 470 agc cct gta gct gca gac cga gtg ggc ccc acc atc ctg aat aag att    1913
Ser Pro Val Ala Ala Asp Arg Val Gly Pro Thr Ile Leu Asn Lys Ile
                475                 480                 485 gaa gcg gct ctg acc aac cag aac ctg tct gtg gat gtg gtg gac cag    1961
Glu Ala Ala Leu Thr Asn Gln Asn Leu Ser Val Asp Val Val Asp Gln
            490                 495                 500 tgc ctc gtc tgc ctc aag gag gag tgg atg aac aaa gtg aag gtg ctt    2009
Cys Leu Val Cys Leu Lys Glu Glu Trp Met Asn Lys Val Lys Val Leu
        505                 510                 515 ttt aag ttc acc aag gtg gac agt cga ccc aaa gag gac aca cag aag    2057
Phe Lys Phe Thr Lys Val Asp Ser Arg Pro Lys Glu Asp Thr Gln Lys
    520                 525                 530 ctg ctg agc atc ctg ggt gcg tcc gag gag gac aat gtc aag ctg ctg    2105
Leu Leu Ser Ile Leu Gly Ala Ser Glu Glu Asp Asn Val Lys Leu Leu
535                 540                 545                 550 aag ttc tgg atg act ggc ctg agc aag acc tac aag tca cac ctc atg    2153
Lys Phe Trp Met Thr Gly Leu Ser Lys Thr Tyr Lys Ser His Leu Met
                555                 560                 565 tcc acg gtc cgc agc ccc aca gcc tcg gag tct cgg aac tga              2195
Ser Thr Val Arg Ser Pro Thr Ala Ser Glu Ser Arg Asn
            570                 575 cccgtcacac acacctgcct aaagacaggg atggctgtcc acaggatcct ccagccccgt    2255
gagagggact gtcccttgag tttctcaact gctggaagga gctgtgtccc agcaaggaag    2315
ggaaaccatc agggctgggc tcggcccgtg caggtttggg gcctgtgtgc ttcccagact    2375
ctccctccag ccgttggaat cgctgaagat ggcaatgaaa ggcggaggga tgatgggctc    2435
tctctgtgtt caaactcctt ggagagacga ctaggaggac agcttgcctc ccaggcccct    2495
tgtggactta gactcaaaac ccgcaggaga aacaggtccg actcagtatg cagtcgcaat    2555
aacatgtctg ctcccgaggt taacattcaa gcgtttctac tttgaaattc agcaagagtt    2615
tctgggcctt atgtttgagg gtacctttg ctgcagttgt gaatattcag tacattgcca    2675
gctcttggtc actgagtgat tgagttaggg ctccgcaaga gactttgggg agtgaagtgg    2735
atctcttcct catcttctgg tcctctgaaa tgtgtgttct gaagccatgg ggctcgtctt    2795
ctggggtgtt cccctgcagg tgctggtgaa ggtaacctgg ggcttaatga tggagtccct    2855
```

```
gatcattttt gcacaagaca ggttgctgag gggtcggcaa gcatctgact tgcccaatcc   2915
cctggatatg gtgagccccg ccatgctttt attctgtatc gcttttgtct ttattgctgc   2975
tttcaacatt tacgtttggt tacagttaac tattttcgga gtgtggtgat tgaagacaat   3035
ttcatcatcc cactgtactt ttttttttga gagggagttt cactcttgtt gcccaggctg   3095
gagtgcaatg gcacgatctt ggctcactgc aacctctgcc tcctgggttc aagcaattct   3155
cctgcctcag cctccagagt agctggaact acaggtgccc gccactatgc ccagctaatt   3215
tttgtatttt ttagtagaga cggggtttca ccgtgttggc cgggctggtc tcaaactcct   3275
gacctcaggt gatccaccca cctcagcctc ccaaagtgct gggattacaa gcgtgagcca   3335
ctgtgcctgg cccttttttt tttttttttt tttttttta aagagatggc atcttgctat   3395
gtcgtccagg ctggtcttga actcctgagt tcaagcagtc ctcctgcttc aacatacagc   3455
tacaggtacc ccccactata cattttttaat aaggattcat ggctcagagg gattttctga   3515
tggttttgct gatttgtttc tagtttttttt gtgtttatat ttaacatgaa gaccaagttt   3575
atataactag gtatctgtat aatgcaacaa cattggaaca caataaagat gtattttgt    3635 aaaaaaaaaa aaaaaaaaaa aaaaaaaaaa aaaaaaaa                           3674
```

<210> SEQ ID NO 2
<211> LENGTH: 579
<212> TYPE: PRT
<213> ORGANISM: Homo sapiens

<400> SEQUENCE: 2

```
Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
            20                  25                  30

Asp Gly Asn Glu Asp Ser Pro Gly Gln Gly Glu Gln Ala Glu Glu Glu
        35                  40                  45

Glu Gly Gly Ile Gln Met Asn Ser Arg Met Arg Ala His Ser Pro Ala
    50                  55                  60

Glu Gly Ala Ser Val Glu Ser Ser Ser Pro Gly Pro Lys Lys Ser Asp
65                  70                  75                  80

Met Cys Glu Gly Cys Arg Ser Leu Ala Ala Gly His Pro Gly Tyr Ile
                85                  90                  95

Ser His Asp Lys Glu Thr Ser Ile Lys Tyr Val Ser His Gln His Pro
            100                 105                 110

Ser His Pro Gln Leu Phe Ser Ile Val Arg Gln Ala Cys Val Arg Ser
        115                 120                 125

Leu Ser Cys Glu Val Cys Pro Gly Arg Glu Gly Pro Ile Phe Phe Gly
    130                 135                 140

Asp Glu Gln His Gly Phe Val Phe Ser His Thr Phe Phe Ile Lys Asp
145                 150                 155                 160

Ser Leu Ala Arg Gly Phe Gln Arg Trp Tyr Ser Ile Ile Thr Ile Met
                165                 170                 175

Met Asp Arg Ile Tyr Leu Ile Asn Ser Trp Pro Phe Leu Leu Gly Lys
            180                 185                 190

Val Arg Gly Ile Ile Asp Glu Leu Gln Gly Lys Ala Leu Lys Val Phe
        195                 200                 205

Glu Ala Glu Gln Phe Gly Cys Pro Gln Arg Ala Gln Arg Met Asn Thr
    210                 215                 220

Ala Phe Thr Pro Phe Leu His Gln Arg Asn Gly Asn Ala Ala Arg Ser
```

|  |  |  |  |  | 225 |  |  |  |  | 230 |  |  |  |  | 235 |  |  |  |  | 240 |

Leu Thr Ser Leu Thr Ser Asp Asp Asn Leu Trp Ala Cys Leu His Thr
                        245                 250                 255

Ser Phe Ala Trp Leu Leu Lys Ala Cys Gly Ser Arg Leu Thr Glu Lys
            260                 265                 270

Leu Leu Glu Gly Ala Pro Thr Glu Asp Thr Leu Val Gln Met Glu Lys
        275                 280                 285

Leu Ala Asp Leu Glu Glu Glu Ser Glu Ser Trp Asp Asn Ser Glu Ala
    290                 295                 300

Glu Glu Glu Glu Lys Ala Pro Val Leu Pro Glu Ser Thr Glu Gly Arg
305                 310                 315                 320

Glu Leu Thr Gln Gly Pro Ala Glu Ser Ser Leu Ser Gly Cys Gly
                325                 330                 335

Ser Trp Gln Pro Arg Lys Leu Pro Val Phe Lys Ser Leu Arg His Met
                340                 345                 350

Arg Gln Val Leu Gly Ala Pro Ser Phe Arg Met Leu Ala Trp His Val
            355                 360                 365

Leu Met Gly Asn Gln Val Ile Trp Lys Ser Arg Asp Val Asp Leu Val
        370                 375                 380

Gln Ser Ala Phe Glu Val Leu Arg Thr Met Leu Pro Val Gly Cys Val
385                 390                 395                 400

Arg Ile Ile Pro Tyr Ser Ser Gln Tyr Glu Glu Ala Tyr Arg Cys Asn
                405                 410                 415

Phe Leu Gly Leu Ser Pro His Val Gln Ile Pro Pro His Val Leu Ser
                420                 425                 430

Ser Glu Phe Ala Val Ile Val Glu Val His Ala Ala Arg Ser Thr
            435                 440                 445

Leu His Pro Val Gly Cys Glu Asp Asp Gln Ser Leu Ser Lys Tyr Glu
    450                 455                 460

Phe Val Val Thr Ser Gly Ser Pro Val Ala Ala Asp Arg Val Gly Pro
465                 470                 475                 480

Thr Ile Leu Asn Lys Ile Glu Ala Ala Leu Thr Asn Gln Asn Leu Ser
                485                 490                 495

Val Asp Val Val Asp Gln Cys Leu Val Cys Leu Lys Glu Glu Trp Met
                500                 505                 510

Asn Lys Val Lys Val Leu Phe Lys Phe Thr Lys Val Ala Ser Arg Pro
            515                 520                 525

Lys Glu Asp Thr Gln Lys Leu Leu Ser Ile Leu Gly Ala Ser Glu Glu
        530                 535                 540

Asp Asn Val Lys Leu Leu Lys Phe Trp Met Thr Gly Leu Ser Lys Thr
545                 550                 555                 560

Tyr Lys Ser His Leu Met Ser Thr Val Arg Ser Pro Thr Ala Ser Glu
                565                 570                 575

Ser Arg Asn

<210> SEQ ID NO 3
<211> LENGTH: 3673
<212> TYPE: DNA
<213> ORGANISM: Homo sapiens
<220> FEATURE:
<221> NAME/KEY: CDS
<222> LOCATION: (456)..(1121)

<400> SEQUENCE: 3
ggtcgctcct ggttctgcca gctcccctga gagcctgaac ccgggcttga gagcctcgcc    60

```
acccegggtg acatccctgc cgtgggcttg ggggctctgg gtgtgattcc gccggtccgg      120
gtcccgcagc gaccacctac ccagcgcagt caggggtggg gctgggaccc agagcgggac      180
cccggctgcc gagtccaggt gtcccgcggg cctcgatttg gggagcagaa aacgccaggt      240
cttcaagggt gtctgccacc accatgcctg acccatttgg cagcagcctc gtgtgtggtg      300
gtctggtgtg gacggtggaa gcgtgattct gctgagtgtc agtgtgacca ctcgtgctca      360
gccgtatctc agcaggagga caggtgccgg agcagctcgt gcagctaagc agccaactgc      420
agaaacgtca ggcctgttgc agtctccaag gcacc atg aat gcc atc gtg gct        473
                                        Met Asn Ala Ile Val Ala
                                         1               5 ctc tgc cac ttc tgc gag ctc cac ggc ccc gc act ctc ttc tgc acg        521
Leu Cys His Phe Cys Glu Leu His Gly Pro Arg Thr Leu Phe Cys Thr
            10                  15                  20 gag gtg ctg cac gcc cca ctt cct caa ggg gat ggg aat gag gac agt        569
Glu Val Leu His Ala Pro Leu Pro Gln Gly Asp Gly Asn Glu Asp Ser
        25                  30                  35 cct ggc cag ggt gag cag gcg gaa gaa gag gaa ggt ggc att cag atg        617
Pro Gly Gln Gly Glu Gln Ala Glu Glu Glu Glu Gly Gly Ile Gln Met
    40                  45                  50 aac agt cgg atg cgt gcg cac agc ccc gca gag ggg gcc agc gtc gag        665
Asn Ser Arg Met Arg Ala His Ser Pro Ala Glu Gly Ala Ser Val Glu
55                  60                  65                  70 tcc agc agc ccg ggg ccc aaa aag tcg gac atg tgc gag ggc tgc cgg        713
Ser Ser Ser Pro Gly Pro Lys Lys Ser Asp Met Cys Glu Gly Cys Arg
                75                  80                  85 tca ctt gct gca ggg cac ccg gga tat atc agc cat gat aaa gag acc        761
Ser Leu Ala Ala Gly His Pro Gly Tyr Ile Ser His Asp Lys Glu Thr
            90                  95                 100 tcc att aaa tac gtc agc cac cag cac ccc agc cac ccc cag ctc ttc        809
Ser Ile Lys Tyr Val Ser His Gln His Pro Ser His Pro Gln Leu Phe
        105                 110                 115 agc att gtc cgc cag gcc tgt gtc cgg agc ctg agc tgt gag gtc tgc        857
Ser Ile Val Arg Gln Ala Cys Val Arg Ser Leu Ser Cys Glu Val Cys
    120                 125                 130 cct ggc cgt gaa ggc ccc atc ttc ttc gga gat gag cag cac ggc ttt        905
Pro Gly Arg Glu Gly Pro Ile Phe Phe Gly Asp Glu Gln His Gly Phe
135                 140                 145                 150 gtg ttc agc cac acc ttc ttc atc aag gac agc ctg gcc agg ggc ttc        953
Val Phe Ser His Thr Phe Phe Ile Lys Asp Ser Leu Ala Arg Gly Phe
                155                 160                 165 cag cgc tgg tac agc atc atc acc atc atg atg gac cgg atc tac ctc       1001
Gln Arg Trp Tyr Ser Ile Ile Thr Ile Met Met Asp Arg Ile Tyr Leu
            170                 175                 180 atc aac tcc tgg ccc ttc ctg ctg ggg aag gtc cgg gga atc atc gat       1049
Ile Asn Ser Trp Pro Phe Leu Leu Gly Lys Val Arg Gly Ile Ile Asp
        185                 190                 195 gag ctc cag ggc aag gcg ctc aag gtg ttt gag gca gcc agt ttg gat       1097
Glu Leu Gln Gly Lys Ala Leu Lys Val Phe Glu Ala Ala Ser Leu Asp
    200                 205                 210 gcc cac agc gtg ctc aga gga tga acacagcctt cacgccattc ctacaccaga      1151
Ala His Ser Val Leu Arg Gly
215                 220 ggaacggcaa cgccgcccgc tcgctgacat cgctgacaag tgatgacaac ctgtgggcgt     1211
gcctgcacac ctcctttgcc tggctcctga aggcgtgtgg cagccggctg accgagaagc     1271
tcctggaagg tgctccgacc gaggatacct tggtccagat ggagaagctc gctgatttag     1331
```

```
aagaggaatc agaaagctgg acaaactctg aggctgaaga ggaggagaaa gcccctgtgt      1391
tgccagagag tacagaaggg cgggagctga cccaggcccc ggcagagtcc tcctctctct      1451
caggctgtgg gagctggcag ccccggaagc tgccagtctt caagtccctc ggcacatga      1511
ggcaggtcct gggtgcccct tctttccgca tgctggcctg gcacgttctc atggggaacc      1571
aggtgatctg gaaaagcaga gacgtggacc tcgtccagtc agcttttgaa gtacttcgga      1631
ccatgcttcc cgtgggctgc gtccgcatca tcccatacag cagccagtac gaggaggcct      1691
atcggtgcaa cttcctgggg ctcagcccgc acgtgcagat ccccccccac gtgctctcct      1751
cagagtttgc tgtcatcgtg gaggtccacg cagccgcacg ttccaccctc caccctgtgg      1811
ggtgtgagga tgaccagtct ctcagcaagt acagtttgt ggtgaccagt gggagccctg       1871
tagctgcaga ccgagtgggc cccaccatcc tgaataagat tgaagcggct ctgaccaacc      1931
agaacctgtc tgtggatgtg gtggaccagt gcctcgtctg cctcaaggag gagtggatga      1991
acaaagtgaa ggtgcttttt aagttcacca aggtggacag tcgacccaaa gaggacacac      2051
agaagctgct gagcatcctg ggtgcgtccg aggaggacaa tgtcaagctg ctgaagttct      2111
ggatgactgg cctgagcaag acctacaagt cacacctcat gtccacggtc cgcagcccca      2171
cagcctcgga gtctcggaac tgaccccgtca cacacacctg cctaaagaca gggatggctg      2231
tccacaggat cctccagccc cgtgagaggg actgtcccett gagtttctca actgctggaa      2291
ggagctgtgt cccagcaagg aagggaaacc atcagggctg gctcggccc tgtcaggttt       2351
ggggcctgtg tgcttcccag actctccctc cagccgttgg aatcgctgaa gatggcaatg      2411
aaaggcggag ggatgatggg ctctctctgt gttcaaactc cttggagaga cgactaggag      2471
gacagcttgc ctcccaggcc ccttgtggac ttagactcaa acccgcagg agaaacaggt       2531
ccgactcagt atgcagtcgc aataacatgt ctgctcccga ggttaacatt caagcgtttc      2591
tactttgaaa ttcagcaaga gtttctgggc cttatgtttg agggtacctt ttgctgcagt      2651
tgtgaatatt cagtacattg ccagctcttg gtcactgagt gattgagtta gggctccgca     2711
agagactttg gggagtgaag tggatctctt cctcatcttc tggtcctctg aaatgtgtgt      2771
tctgaagcca tggggctcgt cttctgggt gttcccctgc aggtgctggt gaaggtaacc       2831
tgggcttaa tgatggagtc cctgatcatt tttgcacaag acaggttgct gaggggtcgg       2891
caagcatctg acttgcccaa tcccctggat atggtgagcc ccgccatgct tttattctgt      2951
atcgcttttg tctttattgc tgctttcaac atttacgttt ggttacagtt aactattttc      3011
ggagtgtggt gattgaagac aatttcatca tcccactgta cttttttttt tgagagggag      3071
tttcactctt gttgcccagg ctggagtgca atggcacgat cttggctcac tgcaacctct      3131
gcctcctggg ttcaagcaat tctcctgcct cagcctccag agtagctgga actacaggtg      3191
cccgccacta tgcccagcta attttttgtat ttttagtag acgggggtt tcaccgtgtt       3251
ggccgggctg gtctcaaact cctgacctca ggtgatccac ccacctcagc ctcccaaagt      3311
gctgggatta caagcgtgag ccactgtgcc tggcccttt ttttttttt tttttttt         3371
ttaaagagat ggcatcttgc tatgtcgtcc aggctggtct tgaactcctg agttcaagca     3431
gtcctcctgc ttcaacatac agctacaggt accccccact atacattttt aataaggatt      3491
catggctcag agggattttc tgatggtttt gctgatttgt ttctagtttt tttgtgttta      3551
tatttaacat gaagaccaag tttatataac taggtatctg tataatgcaa caacattgga     3611
acacaataaa gatgtatttt tgtaaaaaaa aaaaaaaaaa aaaaaaaaaa aaaaaaaaaa      3671
aa                                                                    3673
```

<210> SEQ ID NO 4
<211> LENGTH: 221
<212> TYPE: PRT
<213> ORGANISM: Homo sapiens

<400> SEQUENCE: 4

Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
            20                  25                  30

Asp Gly Asn Glu Asp Ser Pro Gly Gln Gly Glu Gln Ala Glu Glu Glu
        35                  40                  45

Glu Gly Gly Ile Gln Met Asn Ser Arg Met Arg Ala His Ser Pro Ala
    50                  55                  60

Glu Gly Ala Ser Val Glu Ser Ser Ser Pro Gly Pro Lys Lys Ser Asp
65                  70                  75                  80

Met Cys Glu Gly Cys Arg Ser Leu Ala Ala Gly His Pro Gly Tyr Ile
                85                  90                  95

Ser His Asp Lys Glu Thr Ser Ile Lys Tyr Val Ser His Gln His Pro
            100                 105                 110

Ser His Pro Gln Leu Phe Ser Ile Val Arg Gln Ala Cys Val Arg Ser
        115                 120                 125

Leu Ser Cys Glu Val Cys Pro Gly Arg Glu Gly Pro Ile Phe Phe Gly
    130                 135                 140

Asp Glu Gln His Gly Phe Val Phe Ser His Thr Phe Phe Ile Lys Asp
145                 150                 155                 160

Ser Leu Ala Arg Gly Phe Gln Arg Trp Tyr Ser Ile Ile Thr Ile Met
                165                 170                 175

Met Asp Arg Ile Tyr Leu Ile Asn Ser Trp Pro Phe Leu Leu Gly Lys
            180                 185                 190

Val Arg Gly Ile Ile Asp Glu Leu Gln Gly Lys Ala Leu Lys Val Phe
        195                 200                 205

Glu Ala Ala Ser Leu Asp Ala His Ser Val Leu Arg Gly
    210                 215                 220

<210> SEQ ID NO 5
<211> LENGTH: 3702
<212> TYPE: DNA
<213> ORGANISM: Homo sapiens
<220> FEATURE:
<221> NAME/KEY: CDS
<222> LOCATION: (456)..(1649)

<400> SEQUENCE: 5
ggtcgctcct ggttctgcca gctcccctga gagcctgaac ccgggcttga gagcctcgcc      60
accccgggtg acatccctgc cgtgggcttg ggggctctgg gtgtgattcc gccggtccgg     120
gtcccgcagc gaccacctac ccagcgcagt caggggtggg gctgggaccc agagcgggac     180
cccggctgcc gagtccaggt gtcccgcggg cctcgatttg ggagcagaa aacgccaggt      240 cttcaagggt gtctgccacc accatgcctg acccatttgg cagcagcctc gtgtgtggtg     300
gtctggtgtg gacggtggaa gcgtgattct gctgagtgtc agtgtgacca ctcgtgctca     360
gccgtatctc agcaggagga caggtgccgg agcagctcgt gcagctaagc agccaactgc     420
agaaacgtca ggcctgttgc agtctccaag gcacc atg aat gcc atc gtg gct         473
                                     Met Asn Ala Ile Val Ala
                                     1               5

| | | |
|---|---|---|
| ctc tgc cac ttc tgc gag ctc cac ggc ccc cgc act ctc ttc tgc acg<br>Leu Cys His Phe Cys Glu Leu His Gly Pro Arg Thr Leu Phe Cys Thr<br>          10                    15                    20 | 521 |
| gag gtg ctg cac gcc cca ctt cct caa ggg gat ggg aat gag gac agt<br>Glu Val Leu His Ala Pro Leu Pro Gln Gly Asp Gly Asn Glu Asp Ser<br>      25                    30                    35 | 569 |
| cct ggc cag ggt gag cag gcg gaa gaa gag gaa ggt ggc att cag atg<br>Pro Gly Gln Gly Glu Gln Ala Glu Glu Glu Glu Gly Gly Ile Gln Met<br>40                    45                    50 | 617 |
| aac agt cgg atg cgt gcg cac agc ccc gca gag ggg gcc agc gtc gag<br>Asn Ser Arg Met Arg Ala His Ser Pro Ala Glu Gly Ala Ser Val Glu<br>55                    60                    65                    70 | 665 |
| tcc agc agc ccg ggg ccc aaa aag tcg gac atg tgc gag ggc tgc cgg<br>Ser Ser Ser Pro Gly Pro Lys Lys Ser Asp Met Cys Glu Gly Cys Arg<br>                    75                    80                    85 | 713 |
| tca ctt gct gca ggg cac ccg gga tat atc agc cat gat aaa gag acc<br>Ser Leu Ala Ala Gly His Pro Gly Tyr Ile Ser His Asp Lys Glu Thr<br>      90                    95                    100 | 761 |
| tcc att aaa tac gtc agc cac cag cac ccc agc cac ccc cag ctc ttc<br>Ser Ile Lys Tyr Val Ser His Gln His Pro Ser His Pro Gln Leu Phe<br>105                    110                    115 | 809 |
| agc att gtc cgc cag gcc tgt gtc cgg agc ctg agc tgt gag gtc tgc<br>Ser Ile Val Arg Gln Ala Cys Val Arg Ser Leu Ser Cys Glu Val Cys<br>        120                    125                    130 | 857 |
| cct ggc cgt gaa ggc ccc atc ttc ttc gga gat gag cag cac ggc ttt<br>Pro Gly Arg Glu Gly Pro Ile Phe Phe Gly Asp Glu Gln His Gly Phe<br>135                    140                    145                    150 | 905 |
| gtg ttc agc cac acc ttc ttc atc aag gac agc ctg gcc agg ggc ttc<br>Val Phe Ser His Thr Phe Phe Ile Lys Asp Ser Leu Ala Arg Gly Phe<br>                155                    160                    165 | 953 |
| cag cgc tgg tac agc atc atc acc atc atg atg gac cgg atc tac ctc<br>Gln Arg Trp Tyr Ser Ile Ile Thr Ile Met Met Asp Arg Ile Tyr Leu<br>                170                    175                    180 | 1001 |
| atc aac tcc tgg ccc ttc ctg ctg ggg aag gtc cgg gga atc atc gat<br>Ile Asn Ser Trp Pro Phe Leu Leu Gly Lys Val Arg Gly Ile Ile Asp<br>                    185                    190                    195 | 1049 |
| gag ctc cag ggc aag gcg ctc aag gtg ttt gag gca gag cag ttt gga<br>Glu Leu Gln Gly Lys Ala Leu Lys Val Phe Glu Ala Glu Gln Phe Gly<br>200                    205                    210 | 1097 |
| tgc cca cag cgt gct cag agg atg aac aca gcc ttc acg cca ttc cta<br>Cys Pro Gln Arg Ala Gln Arg Met Asn Thr Ala Phe Thr Pro Phe Leu<br>215                    220                    225                    230 | 1145 |
| cac cag agg aac ggc aac gcc gcc cgc tcg ctg aca tcg ctg aca agt<br>His Gln Arg Asn Gly Asn Ala Ala Arg Ser Leu Thr Ser Leu Thr Ser<br>                    235                    240                    245 | 1193 |
| gat gac aac ctg tgg gcg tgc ctg cac acc tcc ttt gcc tgg ctc ctg<br>Asp Asp Asn Leu Trp Ala Cys Leu His Thr Ser Phe Ala Trp Leu Leu<br>              250                    255                    260 | 1241 |
| aag gcg tgt ggc agc cgg ctg acc gag aag ctc ctg gaa ggt gct ccg<br>Lys Ala Cys Gly Ser Arg Leu Thr Glu Lys Leu Leu Glu Gly Ala Pro<br>              265                    270                    275 | 1289 |
| acc gag gat acc ttg gtc cag atg gag aag ctc gct gat tta gaa gag<br>Thr Glu Asp Thr Leu Val Gln Met Glu Lys Leu Ala Asp Leu Glu Glu<br>280                    285                    290 | 1337 |
| gaa tca gaa agc tgg gac aac tct gag gct gaa gag gag gag aaa gcc<br>Glu Ser Glu Ser Trp Asp Asn Ser Glu Ala Glu Glu Glu Glu Lys Ala<br>295                    300                    305                    310 | 1385 |
| cct gtg ttg cca gag agt aca gaa agc ccc tgt gtt gcc aga gag tac<br>Pro Val Leu Pro Glu Ser Thr Glu Ser Pro Cys Val Ala Arg Glu Tyr | 1433 |

|  |  |  |  |  |  |  |  |  |  |  |  |  |  |  |  |
|---|---|---|---|---|---|---|---|---|---|---|---|---|---|---|---|
|  |  |  | 315 |  |  |  | 320 |  |  |  | 325 |  |  |  |  |
| aga | agg | gcg | gga | gct | gac | cca | ggg | ccc | ggc | aga | gtc | ctc | ctc | tct | ctc | 1481 |
| Arg | Arg | Ala | Gly | Ala | Asp | Pro | Gly | Pro | Gly | Arg | Val | Leu | Leu | Ser | Leu |  |
|  |  |  | 330 |  |  |  | 335 |  |  |  | 340 |  |  |  |  |
| agg | ctg | tgg | gag | ctg | gca | gcc | ccg | gaa | gct | gcc | agt | ctt | caa | gtc | cct | 1529 |
| Arg | Leu | Trp | Glu | Leu | Ala | Ala | Pro | Glu | Ala | Ala | Ser | Leu | Gln | Val | Pro |  |
|  |  |  |  | 345 |  |  |  | 350 |  |  |  | 355 |  |  |  |
| ccg | gca | cat | gag | gca | ggt | cct | ggg | tgc | ccc | ttc | ttt | ccg | cat | gct | ggc | 1577 |
| Pro | Ala | His | Glu | Ala | Gly | Pro | Gly | Cys | Pro | Phe | Phe | Pro | His | Ala | Gly |  |
|  | 360 |  |  |  |  | 365 |  |  |  |  | 370 |  |  |  |  |
| ctg | gca | cgt | tct | cat | ggg | gaa | cca | ggt | gat | ctg | gaa | aag | cag | aga | cgt | 1625 |
| Leu | Ala | Arg | Ser | His | Gly | Glu | Pro | Gly | Asp | Leu | Glu | Lys | Gln | Arg | Arg |  |
| 375 |  |  |  |  | 380 |  |  |  |  | 385 |  |  |  |  | 390 |
| gga | cct | cgt | cca | gtc | agc | ttt | tga | agtacttcgg accatgcttc cgtgggctg |  |  |  |  |  |  | 1679 |
| Gly | Pro | Arg | Pro | Val | Ser | Phe |  |  |  |  |  |  |  |  |  |  |
|  |  |  |  | 395 |  |  |  |  |  |  |  |  |  |  |  |

```
cgtccgcatc atcccataca gcagccagta cgaggaggcc tatcggtgca acttcctggg   1739
gctcagcccg cacgtgcaga tccccccca cgtgctctcc tcagagtttg ctgtcatcgt    1799
ggaggtccac gcagccgcac gttccaccct ccaccctgtg gggtgtgagg atgaccagtc   1859
tctcagcaag tacgagtttg tggtgaccag tgggagccct gtagctgcag accgagtggg   1919
ccccaccatc ctgaataaga ttgaagcggc tctgaccaac cagaacctgt ctgtggatgt   1979
ggtggaccag tgcctcgtct gcctcaagga ggagtggatg aacaaagtga aggtgctttt   2039
taagttcacc aaggtggaca gtcgacccaa agaggacaca cagaagctgc tgagcatcct   2099
gggtgcgtcc gaggaggaca atgtcaagct gctgaagttc tggatgactg gcctgagcaa   2159
gacctacaag tcacacctca tgtccacggt ccgcagcccc acagcctcgg agtctcggaa   2219
ctgacccgtc acacacacct gcctaaagac agggatggct gtccacagga tcctccagcc   2279
ccgtgagagg gactgtccct tgagtttctc aactgctgga aggagctgtg tcccagcaag   2339
gaagggaaac catcagggct gggctcggcc ctgtcaggtt tggggcctgt gtgcttccca   2399
gactctccct ccagccgttg aatcgctga agatggcaat gaaaggcgga gggatgatgg   2459
gctctctctg tgttcaaact ccttggagag acgactagga ggacagcttg cctcccaggc   2519
cccttgtgga cttagactca aaacccgcag agaaacagg tccgactcag tatgcagtcg    2579
caataacatg tctgctcccg aggttaacat tcaagcgttt ctactttgaa attcagcaag   2639
agtttctggg cctatgtttt gagggtacct tttgctgcag ttgtgaatat tcagtacatt   2699
gccagctctt ggtcactgag tgattgagtt agggctccgc aagagacttt ggggagtgaa   2759
gtggatctct tcctcatctt ctggtcctct gaaatgtgtg ttctgaagcc atggggctcg   2819
tcttctgggg tgttccctg caggtgctgg tgaaggtaac ctggggctta atgatggagt    2879
ccctgatcat ttttgcacaa gacaggttgc tgaggggtcg gcaagcatct gacttgccca   2939
atcccctgga tatggtgagc cccgccatgc ttttattctg tatcgctttt gtctttattg   2999
ctgctttcaa catttacgtt tggttacagt taactatttt cggagtgtgg tgattgaaga   3059
caatttcatc atcccactgt acttttttttt ttgagaggga gtttcactct tgttgcccag   3119
gctggagtgc aatggcacga tcttggctca ctgcaacctc tgcctcctgg gttcaagcaa   3179
ttctcctgcc tcagcctcca gagtagctgg aactacaggt gcccgccact atgcccagct   3239
aattttttgta ttttttagta gagacggggt ttcaccgtgt tggccgggct ggtctcaaac   3299
tcctgaccctc aggtgatcca cccacctcag cctcccaaag tgctgggatt acaagcgtga   3359
gccactgtgc ctggcccttt tttttttttt tttttttttt tttaaagaga tggcatcttg    3419
```

```
ctatgtcgtc caggctggtc ttgaactcct gagttcaagc agtcctcctg cttcaacata    3479
cagctacagg tacccccac tatacatttt taataaggat tcatggctca gagggatttt    3539
ctgatggttt tgctgatttg tttctagttt ttttgtgttt atatttaaca tgaagaccaa    3599
gtttatataa ctaggtatct gtataatgca acaacattgg aacacaataa agatgtattt    3659
ttgtaaaaaa aaaaaaaaaa aaaaaaaaaa aaaaaaaaaa aaa                       3702
```

<210> SEQ ID NO 6
<211> LENGTH: 397
<212> TYPE: PRT
<213> ORGANISM: Homo sapiens

<400> SEQUENCE: 6

```
Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
                20                  25                  30

Asp Gly Asn Glu Asp Ser Pro Gly Gln Gly Glu Gln Ala Glu Glu Glu
            35                  40                  45

Glu Gly Gly Ile Gln Met Asn Ser Arg Met Arg Ala His Ser Pro Ala
    50                  55                  60

Glu Gly Ala Ser Val Glu Ser Ser Pro Gly Pro Lys Lys Ser Asp
65                  70                  75                  80

Met Cys Glu Gly Cys Arg Ser Leu Ala Ala Gly His Pro Gly Tyr Ile
                85                  90                  95

Ser His Asp Lys Glu Thr Ser Ile Lys Tyr Val Ser Gln His Pro
                100                 105                 110

Ser His Pro Gln Leu Phe Ser Ile Val Arg Gln Ala Cys Val Arg Ser
            115                 120                 125

Leu Ser Cys Glu Val Cys Pro Gly Arg Glu Gly Pro Ile Phe Phe Gly
    130                 135                 140

Asp Glu Gln His Gly Phe Val Phe Ser His Thr Phe Phe Ile Lys Asp
145                 150                 155                 160

Ser Leu Ala Arg Gly Phe Gln Arg Trp Tyr Ser Ile Ile Thr Ile Met
                165                 170                 175

Met Asp Arg Ile Tyr Leu Ile Asn Ser Trp Pro Phe Leu Leu Gly Lys
            180                 185                 190

Val Arg Gly Ile Ile Asp Glu Leu Gln Gly Lys Ala Leu Lys Val Phe
    195                 200                 205

Glu Ala Glu Gln Phe Gly Cys Pro Gln Arg Ala Gln Arg Met Asn Thr
210                 215                 220

Ala Phe Thr Pro Phe Leu His Gln Arg Asn Gly Asn Ala Ala Arg Ser
225                 230                 235                 240

Leu Thr Ser Leu Thr Ser Asp Asp Asn Leu Trp Ala Cys Leu His Thr
                245                 250                 255

Ser Phe Ala Trp Leu Leu Lys Ala Cys Gly Ser Arg Leu Thr Glu Lys
            260                 265                 270

Leu Leu Glu Gly Ala Pro Thr Glu Asp Thr Leu Val Gln Met Glu Lys
    275                 280                 285

Leu Ala Asp Leu Glu Glu Glu Ser Glu Ser Trp Asp Asn Ser Glu Ala
290                 295                 300

Glu Glu Glu Glu Lys Ala Pro Val Leu Pro Glu Ser Thr Glu Ser Pro
305                 310                 315                 320
```

```
Cys Val Ala Arg Glu Tyr Arg Arg Ala Gly Ala Asp Pro Gly Pro Gly
            325                 330                 335

Arg Val Leu Leu Ser Leu Arg Leu Trp Glu Leu Ala Ala Pro Glu Ala
        340                 345                 350

Ala Ser Leu Gln Val Pro Pro Ala His Glu Ala Gly Pro Gly Cys Pro
        355                 360                 365

Phe Phe Pro His Ala Gly Leu Ala Arg Ser His Gly Glu Pro Gly Asp
    370                 375                 380

Leu Glu Lys Gln Arg Arg Gly Pro Arg Pro Val Ser Phe
385                 390                 395

<210> SEQ ID NO 7
<211> LENGTH: 3675
<212> TYPE: DNA
<213> ORGANISM: Homo sapiens
<220> FEATURE:
<221> NAME/KEY: CDS
<222> LOCATION: (456)..(1820)

<400> SEQUENCE: 7
ggtcgctcct ggttctgcca gctcccctga gagcctgaac ccgggcttga gagcctcgcc      60
accccgggtg acatccctgc cgtgggcttg ggggctctgg gtgtgattcc gccggtccgg     120
gtcccgcagc gaccacctac ccagcgcagt caggggtggg gctgggaccc agagcgggac     180
cccggctgcc gagtccaggt gtcccgcggg cctcgatttg gggagcagaa acgccaggt     240 cttcaagggt gtctgccacc accatgcctg acccatttgg cagcagcctc gtgtgtggtg     300
gtctggtgtg gacggtggaa gcgtgattct gctgagtgtc agtgtgacca ctcgtgctca     360
gccgtatctc agcaggagga caggtgccgg agcagctcgt gcagctaagc agccaactgc     420
agaaacgtca ggcctgttgc agtctccaag gcacc atg aat gcc atc gtg gct        473
                                    Met Asn Ala Ile Val Ala
                                     1               5 ctc tgc cac ttc tgc gag ctc cac ggc ccc cgc act ctc ttc tgc acg        521
Leu Cys His Phe Cys Glu Leu His Gly Pro Arg Thr Leu Phe Cys Thr
            10                  15                  20 gag gtg ctg cac gcc cca ctt cct caa ggg gat ggg aat gag gac agt        569
Glu Val Leu His Ala Pro Leu Pro Gln Gly Asp Gly Asn Glu Asp Ser
        25                  30                  35 cct ggc cag ggt gag cag gcg gaa gaa gag gaa ggt ggc att cag atg        617
Pro Gly Gln Gly Glu Gln Ala Glu Glu Glu Glu Gly Gly Ile Gln Met
    40                  45                  50 aac agt cgg atg cgt gcg cac agc ccc gca gag ggg gcc agc gtc gag        665
Asn Ser Arg Met Arg Ala His Ser Pro Ala Glu Gly Ala Ser Val Glu
55                  60                  65                  70 tcc agc agc ccg ggg ccc aaa aag tcg gac atg tgc gag ggc tgc cgg        713
Ser Ser Ser Pro Gly Pro Lys Lys Ser Asp Met Cys Glu Gly Cys Arg
                75                  80                  85 tca ctt gct gca ggg cac ccg gga tat atc agc cat gat aaa gag acc        761
Ser Leu Ala Ala Gly His Pro Gly Tyr Ile Ser His Asp Lys Glu Thr
            90                  95                 100 tcc att aaa tac gtc agc cac cag cac ccc agc cac ccc cag ctc ttc        809
Ser Ile Lys Tyr Val Ser His Gln His Pro Ser His Pro Gln Leu Phe
        105                 110                 115 agc att gtc cgc cag gcc tgt gtc cgg agc ctg agc tgt gag gtc tgc        857
Ser Ile Val Arg Gln Ala Cys Val Arg Ser Leu Ser Cys Glu Val Cys
    120                 125                 130 cct ggc cgt gaa ggc ccc atc ttc ttc gga gat gag cag cac ggc ttt        905
Pro Gly Arg Glu Gly Pro Ile Phe Phe Gly Asp Glu Gln His Gly Phe
135                 140                 145                 150
```

-continued

| | | |
|---|---|---|
| gtg ttc agc cac acc ttc ttc atc aag gac agc ctg gcc agg ggc ttc<br>Val Phe Ser His Thr Phe Phe Ile Lys Asp Ser Leu Ala Arg Gly Phe<br>                155                    160                    165 | | 953 |
| cag cgc tgg tac agc atc atc acc atc atg atg gac cgg atc tac ctc<br>Gln Arg Trp Tyr Ser Ile Ile Thr Ile Met Met Asp Arg Ile Tyr Leu<br>                170                    175                    180 | | 1001 |
| atc aac tcc tgg ccc ttc ctg ctg ggg aag gtc cgg gga atc atc gat<br>Ile Asn Ser Trp Pro Phe Leu Leu Gly Lys Val Arg Gly Ile Ile Asp<br>                185                    190                    195 | | 1049 |
| gag ctc cag ggc aag gcg ctc aag gtg ttt gag gca gag cag ttt gga<br>Glu Leu Gln Gly Lys Ala Leu Lys Val Phe Glu Ala Glu Gln Phe Gly<br>                200                    205                    210 | | 1097 |
| tgc cca cag cgt gct cag agg atg aac aca gcc ttc acg cca ttc cta<br>Cys Pro Gln Arg Ala Gln Arg Met Asn Thr Ala Phe Thr Pro Phe Leu<br>215                    220                    225                    230 | | 1145 |
| cac cag agg aac ggc aac gcc gcc cgc tcg ctg aca tcg ctg aca agt<br>His Gln Arg Asn Gly Asn Ala Ala Arg Ser Leu Thr Ser Leu Thr Ser<br>                    235                    240                    245 | | 1193 |
| gat gac aac ctg tgg gcg tgc ctg cac acc tcc ttt gcc tgg ctc ctg<br>Asp Asp Asn Leu Trp Ala Cys Leu His Thr Ser Phe Ala Trp Leu Leu<br>                250                    255                    260 | | 1241 |
| aag gcg tgt ggc agc cgg ctg acc gag aag ctc ctg gaa ggt gct ccg<br>Lys Ala Cys Gly Ser Arg Leu Thr Glu Lys Leu Leu Glu Gly Ala Pro<br>                265                    270                    275 | | 1289 |
| acc gag gat acc ttg gtc cag atg gag aag ctc gct gat tta gaa gag<br>Thr Glu Asp Thr Leu Val Gln Met Glu Lys Leu Ala Asp Leu Glu Glu<br>        280                    285                    290 | | 1337 |
| gaa tca gaa agc tgg gac aac tct gag gct gaa gag gag aaa gcc<br>Glu Ser Glu Ser Trp Asp Asn Ser Glu Ala Glu Glu Glu Lys Ala<br>295                    300                    305                    310 | | 1385 |
| cct gtg ttg cca gag agt aca gaa ggg cgg gag ctg acc cag ggc ccg<br>Pro Val Leu Pro Glu Ser Thr Glu Gly Arg Glu Leu Thr Gln Gly Pro<br>                315                    320                    325 | | 1433 |
| gca gag tcc tcc tct ctc tca ggc tgt ggg agc tgg cag ccc cgg aag<br>Ala Glu Ser Ser Ser Leu Ser Gly Cys Gly Ser Trp Gln Pro Arg Lys<br>                330                    335                    340 | | 1481 |
| ctg cca gtc ttc aag tcc ctc cgg cac atg agg cag gtc ctg ggt gcc<br>Leu Pro Val Phe Lys Ser Leu Arg His Met Arg Gln Val Leu Gly Ala<br>              345                    350                    355 | | 1529 |
| cct tct ttc cgc atg ctg gcc tgg cac gtt ctc atg ggg aac cag gtg<br>Pro Ser Phe Arg Met Leu Ala Trp His Val Leu Met Gly Asn Gln Val<br>        360                    365                    370 | | 1577 |
| atc tgg aaa agc aga gac gtg gac ctc gtc cag tca gct ttt gaa gta<br>Ile Trp Lys Ser Arg Asp Val Asp Leu Val Gln Ser Ala Phe Glu Val<br>375                    380                    385                    390 | | 1625 |
| ctt cgg acc atg ctt ccc gtg ggc tgc gtc cgc atc atc cca tac agc<br>Leu Arg Thr Met Leu Pro Val Gly Cys Val Arg Ile Ile Pro Tyr Ser<br>                    395                    400                    405 | | 1673 |
| agc cag tac gag gag gcc tat cgg tgc aac ttc ctg ggg ctc agc ccg<br>Ser Gln Tyr Glu Glu Ala Tyr Arg Cys Asn Phe Leu Gly Leu Ser Pro<br>                    410                    415                    420 | | 1721 |
| cac gtg cag atc ccc ccc cca cgt gct ctc ctc aga gtt tgc tgt cat<br>His Val Gln Ile Pro Pro Pro Arg Ala Leu Leu Arg Val Cys Cys His<br>                425                    430                    435 | | 1769 |
| cgt gga ggt cca cgc agc cgc acg ttc cac cct cca ccc tgt ggg gtg<br>Arg Gly Gly Pro Arg Ser Arg Thr Phe His Pro Pro Pro Cys Gly Val<br>        440                    445                    450 | | 1817 |
| tga ggatgaccag tctctcagca agtacgagtt tgtggtgacc agtgggagcc | | 1870 |

-continued

```
ctgtagctgc agaccgagtg ggccccacca tcctgaataa gattgaagcg gctctgacca    1930
accagaacct gtctgtggat gtggtggacc agtgcctcgt ctgcctcaag gaggagtgga    1990
tgaacaaagt gaaggtgctt tttaagttca ccaaggtgga cagtcgaccc aaagaggaca    2050
cacagaagct gctgagcatc ctgggtgcgt ccgaggagga caatgtcaag ctgctgaagt    2110
tctggatgac tggcctgagc aagacctaca agtcacacct catgtccacg gtccgcagcc    2170
ccacagcctc ggagtctcgg aactgacccg tcacacacac ctgcctaaag cagggatgg    2230
ctgtccacag gatcctccag ccccgtgaga gggactgtcc cttgagtttc tcaactgctg    2290
gaaggagctg tgtcccagca aggaagggaa accatcaggg ctgggctcgg ccctgtcagg    2350
tttggggcct gtgtgcttcc cagactctcc ctccagccgt tggaatcgct gaagatggca    2410
atgaaaggcg gagggatgat gggctctctc tgtgttcaaa ctccttggag agacgactag    2470
gaggacagct tgcctcccag gccccttgtg gacttagact caaaacccgc aggagaaaca    2530
ggtccgactc agtatgcagt cgcaataaca tgtctgctcc cgaggttaac attcaagcgt    2590
ttctactttg aaattcagca agagtttctg ggccttatgt ttgagggtac cttttgctgc    2650
agttgtgaat attcagtaca ttgccagctc ttggtcactg agtgattgag ttagggctcc    2710
gcaagagact ttggggagtg aagtggatct cttcctcatc ttctggtcct ctgaaatgtg    2770
tgttctgaag ccatgggggct cgtcttctgg ggtgttcccc tgcaggtgct ggtgaaggta    2830
acctggggct taatgatgga gtccctgatc atttttgcac aagacaggtt gctgagggg    2890
cggcaagcat ctgacttgcc caatcccctg gatatggtga gccccgccat gctttattc    2950
tgtatcgctt ttgtctttat tgctgctttc aacatttacg tttggttaca gttaactatt    3010
ttcggagtgt ggtgattgaa gacaatttca tcatcccact gtactttttt ttttgagagg    3070
gagtttcact cttgttgccc aggctggagt gcaatggcac gatcttggct cactgcaacc    3130
tctgcctcct gggttcaagc aattctcctg cctcagcctc cagagtagct ggaactacag    3190
gtgcccgcca ctatgcccag ctaattttg tattttttag tagagacggg gtttcaccgt    3250
gttggccggg ctggtctcaa actcctgacc tcaggtgatc cacccacctc agcctcccaa    3310
agtgctggga ttacaagcgt gagccactgt gcctggcccc ttttttttt tttttttt    3370
tttttaaaga gatggcatct tgctatgtcg tccaggctgg tcttgaactc ctgagttcaa    3430
gcagtcctcc tgcttcaaca tacagctaca ggtacccccc actatacatt tttaataagg    3490
attcatggct cagagggatt ttctgatggt tttgctgatt tgtttctagt ttttttgtgt    3550
ttatattaa catgaagacc aagtttatat aactaggtat ctgtataatg caacaacatt    3610
ggaacacaat aaagatgtat ttttgtaaaa aaaaaaaaa aaaaaaaaa aaaaaaaaa    3670
aaaaa                                                                3675
```

<210> SEQ ID NO 8
<211> LENGTH: 454
<212> TYPE: PRT
<213> ORGANISM: Homo sapiens

<400> SEQUENCE: 8

```
Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
            20                  25                  30

Asp Gly Asn Glu Asp Ser Pro Gly Gln Gly Glu Gln Ala Glu Glu Glu
        35                  40                  45
```

-continued

```
Glu Gly Gly Ile Gln Met Asn Ser Arg Met Arg Ala His Ser Pro Ala
 50                  55                  60
Glu Gly Ala Ser Val Glu Ser Ser Ser Pro Gly Pro Lys Lys Ser Asp
 65                  70                  75                  80
Met Cys Glu Gly Cys Arg Ser Leu Ala Ala Gly His Pro Gly Tyr Ile
                     85                  90                  95
Ser His Asp Lys Glu Thr Ser Ile Lys Tyr Val Ser His Gln His Pro
                100                 105                 110
Ser His Pro Gln Leu Phe Ser Ile Val Arg Gln Ala Cys Val Arg Ser
                115                 120                 125
Leu Ser Cys Glu Val Cys Pro Gly Arg Glu Gly Pro Ile Phe Phe Gly
130                 135                 140
Asp Glu Gln His Gly Phe Val Phe Ser His Thr Phe Phe Ile Lys Asp
145                 150                 155                 160
Ser Leu Ala Arg Gly Phe Gln Arg Trp Tyr Ser Ile Ile Thr Ile Met
                165                 170                 175
Met Asp Arg Ile Tyr Leu Ile Asn Ser Trp Pro Phe Leu Leu Gly Lys
                180                 185                 190
Val Arg Gly Ile Ile Asp Glu Leu Gln Gly Lys Ala Leu Lys Val Phe
                195                 200                 205
Glu Ala Glu Gln Phe Gly Cys Pro Gln Arg Ala Gln Arg Met Asn Thr
210                 215                 220
Ala Phe Thr Pro Phe Leu His Gln Arg Asn Gly Asn Ala Ala Arg Ser
225                 230                 235                 240
Leu Thr Ser Leu Thr Ser Asp Asp Asn Leu Trp Ala Cys Leu His Thr
                245                 250                 255
Ser Phe Ala Trp Leu Leu Lys Ala Cys Gly Ser Arg Leu Thr Glu Lys
                260                 265                 270
Leu Leu Glu Gly Ala Pro Thr Glu Asp Thr Leu Val Gln Met Glu Lys
                275                 280                 285
Leu Ala Asp Leu Glu Glu Glu Ser Glu Ser Trp Asp Asn Ser Glu Ala
                290                 295                 300
Glu Glu Glu Glu Lys Ala Pro Val Leu Pro Glu Ser Thr Glu Gly Arg
305                 310                 315                 320
Glu Leu Thr Gln Gly Pro Ala Glu Ser Ser Leu Ser Gly Cys Gly
                325                 330                 335
Ser Trp Gln Pro Arg Lys Leu Pro Val Phe Lys Ser Leu Arg His Met
                340                 345                 350
Arg Gln Val Leu Gly Ala Pro Ser Phe Arg Met Leu Ala Trp His Val
                355                 360                 365
Leu Met Gly Asn Gln Val Ile Trp Lys Ser Arg Asp Val Asp Leu Val
                370                 375                 380
Gln Ser Ala Phe Glu Val Leu Arg Thr Met Leu Pro Val Gly Cys Val
385                 390                 395                 400
Arg Ile Ile Pro Tyr Ser Ser Gln Tyr Glu Glu Ala Tyr Arg Cys Asn
                405                 410                 415
Phe Leu Gly Leu Ser Pro His Val Gln Ile Pro Pro Arg Ala Leu
                420                 425                 430
Leu Arg Val Cys Cys His Arg Gly Gly Pro Arg Ser Arg Thr Phe His
                435                 440                 445
Pro Pro Pro Cys Gly Val
450
```

-continued

```
<210> SEQ ID NO 9
<211> LENGTH: 3673
<212> TYPE: DNA
<213> ORGANISM: Homo sapiens
<220> FEATURE:
<221> NAME/KEY: CDS
<222> LOCATION: (456)..(1856)

<400> SEQUENCE: 9
ggtcgctcct ggttctgcca gctcccctga gagcctgaac ccgggcttga gagcctcgcc      60
accccgggtg acatccctgc cgtgggcttg ggggctctgg gtgtgattcc gccggtccgg     120
gtcccgcagc gaccacctac ccagcgcagt caggggtggg gctgggaccc agagcgggac     180
cccggctgcc gagtccaggt gtcccgcggg cctcgatttg gggagcagaa aacgccaggt     240
cttcaagggt gtctgccacc accatgcctg acccatttgg cagcagcctc gtgtgtggtg     300
gtctggtgtg gacggtggaa gcgtgattct gctgagtgtc agtgtgacca ctcgtgctca     360
gccgtatctc agcaggagga caggtgccgg agcagctcgt gcagctaagc agccaactgc     420
agaaacgtca ggcctgttgc agtctccaag gcacc atg aat gcc atc gtg gct       473
                                    Met Asn Ala Ile Val Ala
                                      1               5 ctc tgc cac ttc tgc gag ctc cac ggc ccc cgc act ctc ttc tgc acg       521
Leu Cys His Phe Cys Glu Leu His Gly Pro Arg Thr Leu Phe Cys Thr
         10                  15                  20 gag gtg ctg cac gcc cca ctt cct caa ggg gat ggg aat gag gac agt       569
Glu Val Leu His Ala Pro Leu Pro Gln Gly Asp Gly Asn Glu Asp Ser
     25                  30                  35 cct ggc cag ggt gag cag gcg gaa gaa gag gaa ggt ggc att cag atg       617
Pro Gly Gln Gly Glu Gln Ala Glu Glu Glu Glu Gly Gly Ile Gln Met
 40                  45                  50 aac agt cgg atg cgt gcg cac agc ccc gca gag ggg gcc agc gtc gag       665
Asn Ser Arg Met Arg Ala His Ser Pro Ala Glu Gly Ala Ser Val Glu
 55                  60                  65                  70 tcc agc agc ccg ggg ccc aaa aag tcg gac atg tgc gag ggc tgc cgg       713
Ser Ser Ser Pro Gly Pro Lys Lys Ser Asp Met Cys Glu Gly Cys Arg
                 75                  80                  85 tca ctt gct gca ggg cac ccg gga tat atc agc cat gat aaa gag acc       761
Ser Leu Ala Ala Gly His Pro Gly Tyr Ile Ser His Asp Lys Glu Thr
             90                  95                 100 tcc att aaa tac gtc agc cac cag cac ccc agc cac ccc cag ctc ttc       809
Ser Ile Lys Tyr Val Ser His Gln His Pro Ser His Pro Gln Leu Phe
        105                 110                 115 agc att gtc cgc cag gcc tgt gtc cgg agc ctg agc tgt gag gtc tgc       857
Ser Ile Val Arg Gln Ala Cys Val Arg Ser Leu Ser Cys Glu Val Cys
    120                 125                 130 cct ggc cgt gaa ggc ccc atc ttc ttc gga gat gag cag cac ggc ttt       905
Pro Gly Arg Glu Gly Pro Ile Phe Phe Gly Asp Glu Gln His Gly Phe
135                 140                 145                 150 gtg ttc agc cac acc ttc ttc atc aag gac agc ctg gcc agg ggc ttc       953
Val Phe Ser His Thr Phe Phe Ile Lys Asp Ser Leu Ala Arg Gly Phe
                155                 160                 165 cag cgc tgg tac agc atc atc acc atc atg atg gac cgg atc tac ctc      1001
Gln Arg Trp Tyr Ser Ile Ile Thr Ile Met Met Asp Arg Ile Tyr Leu
            170                 175                 180 atc aac tcc tgg ccc ttc ctg ctg ggg aag gtc cgg gga atc atc gat      1049
Ile Asn Ser Trp Pro Phe Leu Leu Gly Lys Val Arg Gly Ile Ile Asp
        185                 190                 195 gag ctc cag ggc aag gcg ctc aag gtg ttt gag gca gag cag ttt gga      1097
Glu Leu Gln Gly Lys Ala Leu Lys Val Phe Glu Ala Glu Gln Phe Gly
    200                 205                 210
```

| | |
|---|---|
| tgc cca cag cgt gct cag agg atg aac aca gcc ttc acg cca ttc cta<br>Cys Pro Gln Arg Ala Gln Arg Met Asn Thr Ala Phe Thr Pro Phe Leu<br>215                220                225              230 | 1145 |
| cac cag agg aac ggc aac gcc gcc cgc tcg ctg aca tcg ctg aca agt<br>His Gln Arg Asn Gly Asn Ala Ala Arg Ser Leu Thr Ser Leu Thr Ser<br>                235                240              245 | 1193 |
| gat gac aac ctg tgg gcg tgc ctg cac acc tcc ttt gcc tgg ctc ctg<br>Asp Asp Asn Leu Trp Ala Cys Leu His Thr Ser Phe Ala Trp Leu Leu<br>          250                255              260 | 1241 |
| aag gcg tgt ggc agc cgg ctg acc gag aag ctc ctg gaa ggt gct ccg<br>Lys Ala Cys Gly Ser Arg Leu Thr Glu Lys Leu Leu Glu Gly Ala Pro<br>265                270                275 | 1289 |
| acc gag gat acc ttg gtc cag atg gag aag ctc gct gat tta gaa gag<br>Thr Glu Asp Thr Leu Val Gln Met Glu Lys Leu Ala Asp Leu Glu Glu<br>          280                285              290 | 1337 |
| gaa tca gaa agc tgg gac aac tct gag gct gaa gag gag gag aaa gcc<br>Glu Ser Glu Ser Trp Asp Asn Ser Glu Ala Glu Glu Glu Glu Lys Ala<br>295                300                305              310 | 1385 |
| cct gtg ttg cca gag agt aca gaa ggg cgg gag ctg acc cag ggc ccg<br>Pro Val Leu Pro Glu Ser Thr Glu Gly Arg Glu Leu Thr Gln Gly Pro<br>                315                320              325 | 1433 |
| gca gag tcc tcc tct ctc tca ggc tgt ggg agc tgg cag ccc cgg aag<br>Ala Glu Ser Ser Ser Leu Ser Gly Cys Gly Ser Trp Gln Pro Arg Lys<br>          330                335              340 | 1481 |
| ctg cca gtc ttc aag tcc ctc cgg cac atg agg cag gtc ctg ggt gcc<br>Leu Pro Val Phe Lys Ser Leu Arg His Met Arg Gln Val Leu Gly Ala<br>345                350                355 | 1529 |
| cct tct ttc cgc atg ctg gcc tgg cac gtt ctc atg ggg aac cag gtg<br>Pro Ser Phe Arg Met Leu Ala Trp His Val Leu Met Gly Asn Gln Val<br>          360                365              370 | 1577 |
| atc tgg aaa agc aga gac gtg gac ctc gtc cag tca gct ttt gaa gta<br>Ile Trp Lys Ser Arg Asp Val Asp Leu Val Gln Ser Ala Phe Glu Val<br>375                380                385              390 | 1625 |
| ctt cgg acc atg ctt ccc gtg ggc tgc gtc cgc atc atc cca tac agc<br>Leu Arg Thr Met Leu Pro Val Gly Cys Val Arg Ile Ile Pro Tyr Ser<br>                395                400              405 | 1673 |
| agc cag tac gag gag gcc tat cgg tgc aac ttc ctg ggg ctc agc ccg<br>Ser Gln Tyr Glu Glu Ala Tyr Arg Cys Asn Phe Leu Gly Leu Ser Pro<br>          410                415              420 | 1721 |
| cac gtg cag atc ccc ccc acg tgc tct cct cag agt ttg ctg tca tcg<br>His Val Gln Ile Pro Pro Thr Cys Ser Pro Gln Ser Leu Leu Ser Ser<br>                425                430              435 | 1769 |
| tgg agg tcc acg cag ccg cac gtt cca ccc tcc acc ctg tgg ggt gtg<br>Trp Arg Ser Thr Gln Pro His Val Pro Pro Ser Thr Leu Trp Gly Val<br>          440                445              450 | 1817 |
| agg atg acc agt ctc tca gca agt acg agt ttg tgg tga ccagtgggag<br>Arg Met Thr Ser Leu Ser Ala Ser Thr Ser Leu Trp<br>455                460                465 | 1866 |
| ccctgtagct gcagaccgag tgggccccac catcctgaat aagattgaag cggctctgac | 1926 |
| caaccagaac ctgtctgtgg atgtggtgga ccagtgcctc gtctgcctca aggaggagtg | 1986 |
| gatgaacaaa gtgaaggtgc tttttaagtt caccaaggtg gacagtcgac ccaaagagga | 2046 |
| cacacagaag ctgctgagca tcctgggtgc gtccgaggag acaatgtca agctgctgaa | 2106 |
| gttctggatg actggcctga gcaagaccta caagtcacac ctcatgtcca cggtccgcag | 2166 |
| ccccacagcc tcggagtctc ggaactgacc cgtcacacac acctgcctaa agacagggat | 2226 |
| ggctgtccac aggatcctcc agccccgtga gagggactgt cccttgagtt ctcaactgc | 2286 |

```
tggaaggagc tgtgtcccag caaggaaggg aaaccatcag ggctgggctc ggccctgtca    2346 ggtttgggc  ctgtgtgctt cccagactct ccctccagcc gttggaatcg ctgaagatgg    2406
caatgaaagg cggagggatg atgggctctc tctgtgttca aactccttgg agagacgact    2466
aggaggacag cttgcctccc aggcccttg  tggacttaga ctcaaaaccc gcaggagaaa    2526
caggtccgac tcagtatgca gtcgcaataa catgtctgct cccgaggtta acattcaagc    2586
gtttctactt tgaaattcag caagagtttc tgggccttat gtttgagggt acctttgct    2646 gcagttgtga atattcagta cattgccagc tcttggtcac tgagtgattg agttagggct    2706
ccgcaagaga ctttggggag tgaagtggat ctcttcctca tcttctggtc ctctgaaatg    2766
tgtgttctga agccatgggg ctcgtcttct ggggtgttcc cctgcaggtg ctggtgaagg    2826
taacctgggg cttaatgatg gagtccctga tcattttgc  acaagacagg ttgctgaggg    2886
gtcggcaagc atctgacttg cccaatcccc tggatatggt gagccccgcc atgctttat     2946 tctgtatcgc ttttgtcttt attgctgctt tcaacattta cgtttggtta cagttaacta    3006
ttttcggagt gtggtgattg aagacaattt catcatccca ctgtacttt  ttttttgaga    3066 gggagtttca ctcttgttgc ccaggctgga gtgcaatggc acgatcttgg ctcactgcaa    3126
cctctgcctc ctgggttcaa gcaattctcc tgcctcagcc tccagagtag ctggaactac    3186
aggtgcccgc cactatgccc agctaatttt tgtatttttt agtagagacg gggtttcacc    3246
gtgttggccg gctggtctc  aaactcctga cctcaggtga tccacccacc tcagcctccc    3306
aaagtgctgg gattacaagc gtgagccact gtgcctggcc ctttttttt  tttttttttt    3366 ttttttaaa  gagatggcat cttgctatgt cgtccaggct ggtcttgaac tcctgagttc    3426
aagcagtcct cctgcttcaa catacagcta caggtacccc ccactataca tttttaataa    3486
ggattcatgg ctcagaggga ttttctgatg gttttgctga tttgtttcta gttttttgt     3546 gtttatattt aacatgaaga ccaagtttat ataactaggt atctgtataa tgcaacaaca    3606
ttggaacaca ataagatgt  attttgtaa  aaaaaaaaa  aaaaaaaaa  aaaaaaaaa     3666 aaaaaaa                                                              3673
```

<210> SEQ ID NO 10
<211> LENGTH: 466
<212> TYPE: PRT
<213> ORGANISM: Homo sapiens

<400> SEQUENCE: 10

```
Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
            20                  25                  30

Asp Gly Asn Glu Asp Ser Pro Gly Gln Gly Glu Gln Ala Glu Glu Glu
        35                  40                  45

Glu Gly Gly Ile Gln Met Asn Ser Arg Met Arg Ala His Ser Pro Ala
    50                  55                  60

Glu Gly Ala Ser Val Glu Ser Ser Pro Gly Pro Lys Lys Ser Asp
65                  70                  75                  80

Met Cys Glu Gly Cys Arg Ser Leu Ala Ala Gly His Pro Gly Tyr Ile
                85                  90                  95

Ser His Asp Lys Glu Thr Ser Ile Lys Tyr Val Ser His Gln His Pro
            100                 105                 110

Ser His Pro Gln Leu Phe Ser Ile Val Arg Gln Ala Cys Val Arg Ser
        115                 120                 125
```

```
Leu Ser Cys Glu Val Cys Pro Gly Arg Glu Gly Pro Ile Phe Phe Gly
130                 135                 140

Asp Glu Gln His Gly Phe Val Phe Ser His Thr Phe Phe Ile Lys Asp
145                 150                 155                 160

Ser Leu Ala Arg Gly Phe Gln Arg Trp Tyr Ser Ile Ile Thr Ile Met
                165                 170                 175

Met Asp Arg Ile Tyr Leu Ile Asn Ser Trp Pro Phe Leu Leu Gly Lys
                180                 185                 190

Val Arg Gly Ile Ile Asp Glu Leu Gln Gly Lys Ala Leu Lys Val Phe
                195                 200                 205

Glu Ala Glu Gln Phe Gly Cys Pro Gln Arg Ala Gln Arg Met Asn Thr
210                 215                 220

Ala Phe Thr Pro Phe Leu His Gln Arg Asn Gly Asn Ala Ala Arg Ser
225                 230                 235                 240

Leu Thr Ser Leu Thr Ser Asp Asp Asn Leu Trp Ala Cys Leu His Thr
                245                 250                 255

Ser Phe Ala Trp Leu Leu Lys Ala Cys Gly Ser Arg Leu Thr Glu Lys
                260                 265                 270

Leu Leu Glu Gly Ala Pro Thr Glu Asp Thr Leu Val Gln Met Glu Lys
                275                 280                 285

Leu Ala Asp Leu Glu Glu Glu Ser Glu Ser Trp Asp Asn Ser Glu Ala
290                 295                 300

Glu Glu Glu Glu Lys Ala Pro Val Leu Pro Glu Ser Thr Glu Gly Arg
305                 310                 315                 320

Glu Leu Thr Gln Gly Pro Ala Glu Ser Ser Ser Leu Ser Gly Cys Gly
                325                 330                 335

Ser Trp Gln Pro Arg Lys Leu Pro Val Phe Lys Ser Leu Arg His Met
                340                 345                 350

Arg Gln Val Leu Gly Ala Pro Ser Phe Arg Met Leu Ala Trp His Val
                355                 360                 365

Leu Met Gly Asn Gln Val Ile Trp Lys Ser Arg Asp Val Asp Leu Val
370                 375                 380

Gln Ser Ala Phe Glu Val Leu Arg Thr Met Leu Pro Val Gly Cys Val
385                 390                 395                 400

Arg Ile Ile Pro Tyr Ser Ser Gln Tyr Glu Glu Ala Tyr Arg Cys Asn
                405                 410                 415

Phe Leu Gly Leu Ser Pro His Val Gln Ile Pro Pro Thr Cys Ser Pro
                420                 425                 430

Gln Ser Leu Leu Ser Ser Trp Arg Ser Thr Gln Pro His Val Pro Pro
                435                 440                 445

Ser Thr Leu Trp Gly Val Arg Met Thr Ser Leu Ser Ala Ser Thr Ser
450                 455                 460

Leu Trp
465

<210> SEQ ID NO 11
<211> LENGTH: 3674
<212> TYPE: DNA
<213> ORGANISM: Homo sapiens
<220> FEATURE:
<221> NAME/KEY: CDS
<222> LOCATION: (456)..(1844)

<400> SEQUENCE: 11
ggtcgctcct ggttctgcca gctcccctga gagcctgaac ccgggcttga gagcctcgcc    60
```

```
accccgggtg acatccctgc cgtgggcttg ggggctctgg gtgtgattcc gccggtccgg     120
gtcccgcagc gaccacctac ccagcgcagt caggggtggg gctgggaccc agagcgggac     180
cccggctgcc gagtccaggt gtcccgcggg cctcgatttg gggagcagaa aacgccaggt     240
cttcaagggt gtctgccacc accatgcctg acccatttgg cagcagcctc gtgtgtggtg     300
gtctggtgtg gacggtggaa gcgtgattct gctgagtgtc agtgtgacca ctcgtgctca     360
gccgtatctc agcaggagga caggtgccgg agcagctcgt gcagctaagc agccaactgc     420
agaaacgtca ggcctgttgc agtctccaag gcacc atg aat gcc atc gtg gct        473
                                       Met Asn Ala Ile Val Ala
                                        1               5
```

| ctc tgc cac ttc tgc gag ctc cac ggc ccc cgc act ctc ttc tgc acg | 521 |
| Leu Cys His Phe Cys Glu Leu His Gly Pro Arg Thr Leu Phe Cys Thr | |
|     10              15              20 | |

```
gag gtg ctg cac gcc cca ctt cct caa ggg gat ggg aat gag gac agt     569
Glu Val Leu His Ala Pro Leu Pro Gln Gly Asp Gly Asn Glu Asp Ser
         25                  30                  35 cct ggc cag ggt gag cag gcg gaa gaa gag gaa ggt ggc att cag atg     617
Pro Gly Gln Gly Glu Gln Ala Glu Glu Glu Glu Gly Gly Ile Gln Met
 40                  45                  50 aac agt cgg atg cgt gcg cac agc ccc gca gag ggg gcc agc gtc gag     665
Asn Ser Arg Met Arg Ala His Ser Pro Ala Glu Gly Ala Ser Val Glu
 55                  60                  65                  70 tcc agc agc ccg ggg ccc aaa aag tcg gac atg tgc gag ggc tgc cgg     713
Ser Ser Ser Pro Gly Pro Lys Lys Ser Asp Met Cys Glu Gly Cys Arg
                 75                  80                  85 tca ctt gct gca ggg cac ccg gga tat atc agc cat gat aaa gag acc     761
Ser Leu Ala Ala Gly His Pro Gly Tyr Ile Ser His Asp Lys Glu Thr
         90                  95                 100 tcc att aaa tac gtc agc cac cag cac ccc agc cac ccc cag ctc ttc     809
Ser Ile Lys Tyr Val Ser His Gln His Pro Ser His Pro Gln Leu Phe
            105                 110                 115 agc att gtc cgc cag gcc tgt gtc cgg agc ctg agc tgt gag gtc tgc     857
Ser Ile Val Arg Gln Ala Cys Val Arg Ser Leu Ser Cys Glu Val Cys
120                 125                 130 cct ggc cgt gaa ggc ccc atc ttc ttc gga gat gag cag cac ggc ttt     905
Pro Gly Arg Glu Gly Pro Ile Phe Phe Gly Asp Glu Gln His Gly Phe
135                 140                 145                 150 gtg ttc agc cac acc ttc ttc atc aag gac agc ctg gcc agg ggc ttc     953
Val Phe Ser His Thr Phe Phe Ile Lys Asp Ser Leu Ala Arg Gly Phe
                155                 160                 165 cag cgc tgg tac agc atc atc acc atc atg atg gac cgg atc tac ctc     1001
Gln Arg Trp Tyr Ser Ile Ile Thr Ile Met Met Asp Arg Ile Tyr Leu
            170                 175                 180 atc aac tcc tgg ccc ttc ctg ctg ggg aag gtc cgg gga atc atc gat     1049
Ile Asn Ser Trp Pro Phe Leu Leu Gly Lys Val Arg Gly Ile Ile Asp
185                 190                 195 gag ctc cag ggc aag gcg ctc aag gtg ttt gag gca gag cag ttt gga     1097
Glu Leu Gln Gly Lys Ala Leu Lys Val Phe Glu Ala Glu Gln Phe Gly
200                 205                 210 tgc cca cag cgt gct cag agg atg aac aca gcc ttc acg cca ttc cta     1145
Cys Pro Gln Arg Ala Gln Arg Met Asn Thr Ala Phe Thr Pro Phe Leu
215                 220                 225                 230 cac cag agg aac ggc aac gcc gcc cgc tcg ctg aca tcg ctg aca agt     1193
His Gln Arg Asn Gly Asn Ala Ala Arg Ser Leu Thr Ser Leu Thr Ser
                235                 240                 245 gat gac aac ctg tgg gcg tgc ctg cac acc tcc ttt gcc tgg ctc ctg     1241
Asp Asp Asn Leu Trp Ala Cys Leu His Thr Ser Phe Ala Trp Leu Leu
```

|  |  |  |  |  |  |  |  |  |  |  |  |  |  |  |  |  |
|---|---|---|---|---|---|---|---|---|---|---|---|---|---|---|---|---|
|  |  | 250 |  |  |  |  | 255 |  |  |  |  | 260 |  |  |  |  |
| aag | gcg | tgt | ggc | agc | cgg | ctg | acc | gag | aag | ctc | ctg | gaa | ggt | gct | ccg | 1289 |
| Lys | Ala | Cys | Gly | Ser | Arg | Leu | Thr | Glu | Lys | Leu | Leu | Glu | Gly | Ala | Pro |  |
|  |  |  | 265 |  |  |  |  | 270 |  |  |  |  | 275 |  |  |  |
| acc | gag | gat | acc | ttg | gtc | cag | atg | gag | aag | ctc | gct | gat | tta | gaa | gag | 1337 |
| Thr | Glu | Asp | Thr | Leu | Val | Gln | Met | Glu | Lys | Leu | Ala | Asp | Leu | Glu | Glu |  |
|  | 280 |  |  |  |  | 285 |  |  |  |  | 290 |  |  |  |  |  |
| gaa | tca | gaa | agc | tgg | gac | aac | tct | gag | gct | gaa | gag | gag | gag | aaa | gcc | 1385 |
| Glu | Ser | Glu | Ser | Trp | Asp | Asn | Ser | Glu | Ala | Glu | Glu | Glu | Glu | Lys | Ala |  |
| 295 |  |  |  |  | 300 |  |  |  |  | 305 |  |  |  |  | 310 |  |
| cct | gtg | ttg | cca | gag | agt | aca | gaa | ggg | cgg | gag | ctg | acc | cag | ggc | ccg | 1433 |
| Pro | Val | Leu | Pro | Glu | Ser | Thr | Glu | Gly | Arg | Glu | Leu | Thr | Gln | Gly | Pro |  |
|  |  |  |  | 315 |  |  |  |  | 320 |  |  |  |  | 325 |  |  |
| gca | gag | tcc | tcc | tct | ctc | tca | ggc | tgt | ggg | agc | tgg | cag | ccc | cgg | aag | 1481 |
| Ala | Glu | Ser | Ser | Ser | Leu | Ser | Gly | Cys | Gly | Ser | Trp | Gln | Pro | Arg | Lys |  |
|  |  |  | 330 |  |  |  |  | 335 |  |  |  |  | 340 |  |  |  |
| ctg | cca | gtc | ttc | aag | tcc | ctc | cgg | cac | atg | agg | cag | gtc | ctg | ggt | gcc | 1529 |
| Leu | Pro | Val | Phe | Lys | Ser | Leu | Arg | His | Met | Arg | Gln | Val | Leu | Gly | Ala |  |
|  |  | 345 |  |  |  |  | 350 |  |  |  |  | 355 |  |  |  |  |
| cct | tct | ttc | cgc | atg | ctg | gcc | tgg | cac | gtt | ctc | atg | ggg | aac | cag | gtg | 1577 |
| Pro | Ser | Phe | Arg | Met | Leu | Ala | Trp | His | Val | Leu | Met | Gly | Asn | Gln | Val |  |
|  | 360 |  |  |  |  | 365 |  |  |  |  | 370 |  |  |  |  |  |
| atc | tgg | aaa | agc | aga | gac | gtg | gac | ctc | gtc | cag | tca | gct | ttt | gaa | gta | 1625 |
| Ile | Trp | Lys | Ser | Arg | Asp | Val | Asp | Leu | Val | Gln | Ser | Ala | Phe | Glu | Val |  |
| 375 |  |  |  |  | 380 |  |  |  |  | 385 |  |  |  |  | 390 |  |
| ctt | cgg | acc | atg | ctt | ccc | gtg | ggc | tgc | gtc | cgc | atc | atc | cca | tac | agc | 1673 |
| Leu | Arg | Thr | Met | Leu | Pro | Val | Gly | Cys | Val | Arg | Ile | Ile | Pro | Tyr | Ser |  |
|  |  |  | 395 |  |  |  |  | 400 |  |  |  |  | 405 |  |  |  |
| agc | cag | tac | gag | gag | gcc | tat | cgg | tgc | aac | ttc | ctg | ggg | ctc | agc | ccg | 1721 |
| Ser | Gln | Tyr | Glu | Glu | Ala | Tyr | Arg | Cys | Asn | Phe | Leu | Gly | Leu | Ser | Pro |  |
|  |  | 410 |  |  |  |  | 415 |  |  |  |  | 420 |  |  |  |  |
| cac | gtg | cag | atc | ccc | ccc | cac | gtg | ctc | tcc | tca | gag | ttt | gct | gtc | atc | 1769 |
| His | Val | Gln | Ile | Pro | Pro | His | Val | Leu | Ser | Ser | Glu | Phe | Ala | Val | Ile |  |
|  | 425 |  |  |  |  | 430 |  |  |  |  | 435 |  |  |  |  |  |
| gtg | gag | gtc | cac | gca | gcc | gca | cgt | tcc | acc | ctc | cac | cct | gtg | ggg | tgt | 1817 |
| Val | Glu | Val | His | Ala | Ala | Ala | Arg | Ser | Thr | Leu | His | Pro | Val | Gly | Cys |  |
| 440 |  |  |  |  | 445 |  |  |  |  | 450 |  |  |  |  |  |  |
| gag | gat | gac | cag | tct | ctc | agc | aag | tag | gagtttgtgg | tgaccagtgg |  |  |  |  |  | 1864 |
| Glu | Asp | Asp | Gln | Ser | Leu | Ser | Lys |  |  |  |  |  |  |  |  |  |
| 455 |  |  |  | 460 |  |  |  |  |  |  |  |  |  |  |  |  |

| | |
|---|---|
| gagccctgta gctgcagacc gagtgggccc caccatcctg aataagattg aagcggctct | 1924 |
| gaccaaccag aacctgtctg tggatgtggt ggaccagtgc ctcgtctgcc tcaaggagga | 1984 |
| gtggatgaac aaagtgaagg tgcttttttaa gttcaccaag gtggacagtc gacccaaaga | 2044 |
| ggacacacag aagctgctga gcatcctggg tgcgtccgag gaggacaatg tcaagctgct | 2104 |
| gaagttctgg atgactggcc tgagcaagac ctacaagtca cacctcatgt ccacggtccg | 2164 |
| cagccccaca gcctcggagt ctcggaactg accgtcaca cacacctgcc taaagacagg | 2224 |
| gatggctgtc cacaggatcc tccagccccg tgagagggac tgtcccttga gtttctcaac | 2284 |
| tgctggaagg agctgtgtcc cagcaaggaa gggaaaccat cagggctggg ctcggccctg | 2344 |
| tcaggtttgg ggcctgtgtg cttcccagac tctccctcca gccgttggaa tgctgaaga | 2404 |
| tggcaatgaa aggcggaggg atgatgggct ctctctgtgt caaactcct tggagagacg | 2464 |
| actaggagga cagcttgcct cccaggcccc ttgtggactt agactcaaaa cccgcaggag | 2524 |
| aaacaggtcc gactcagtat gcagtcgcaa taacatgtct gctcccgagg ttaacattca | 2584 |
| agcgtttcta ctttgaaatt cagcaagagt ttctgggcct tatgtttgag ggtaccttttt | 2644 |

```
gctgcagttg tgaatattca gtacattgcc agctcttggt cactgagtga ttgagttagg    2704
gctccgcaag agactttggg gagtgaagtg gatctcttcc tcatcttctg gtcctctgaa    2764
atgtgtgttc tgaagccatg gggctcgtct tctggggtgt tcccctgcag gtgctggtga    2824
aggtaacctg gggcttaatg atggagtccc tgatcatttt tgcacaagac aggttgctga    2884
ggggtcggca agcatctgac ttgcccaatc ccctggatat ggtgagcccc gccatgcttt    2944
tattctgtat cgcttttgtc tttattgctg ctttcaacat ttacgtttgg ttacagttaa    3004
ctattttcgg agtgtggtga ttgaagacaa tttcatcatc ccactgtact ttttttttg     3064 agagggagtt tcactcttgt tgcccaggct ggagtgcaat ggcacgatct ggctcactg     3124 caacctctgc ctcctgggtt caagcaattc tcctgcctca gcctccagag tagctggaac    3184
tacaggtgcc cgccactatg cccagctaat ttttgtattt tttagtagag acggggtttc    3244
accgtgttgg ccgggctggt ctcaaactcc tgacctcagg tgatccaccc acctcagcct    3304
cccaaagtgc tgggattaca agcgtgagcc actgtgcctg gcccttttt ttttttttt     3364 ttttttttt aaagagatgg catcttgcta tgtcgtccag gctggtcttg aactcctgag     3424
ttcaagcagt cctcctgctt caacatacag ctacaggtac ccccactat acattttaa     3484 taaggattca tggctcagag ggatttctg atggttttgc tgatttgttt ctagtttttt    3544
tgtgtttata tttaacatga agaccaagtt tatataacta ggtatctgta taatgcaaca    3604
acattggaac acaataaaga tgtatttttg taaaaaaaaa aaaaaaaaaa aaaaaaaaa    3664 aaaaaaaaaa                                                          3674

<210> SEQ ID NO 12
<211> LENGTH: 462
<212> TYPE: PRT
<213> ORGANISM: Homo sapiens

<400> SEQUENCE: 12

Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
            20                  25                  30

Asp Gly Asn Glu Asp Ser Pro Gly Gln Gly Glu Gln Ala Glu Glu Glu
        35                  40                  45

Glu Gly Gly Ile Gln Met Asn Ser Arg Met Arg Ala His Ser Pro Ala
    50                  55                  60

Glu Gly Ala Ser Val Glu Ser Ser Pro Gly Pro Lys Lys Ser Asp
65                  70                  75                  80

Met Cys Glu Gly Cys Arg Ser Leu Ala Ala Gly His Pro Gly Tyr Ile
                85                  90                  95

Ser His Asp Lys Glu Thr Ser Ile Lys Tyr Val Ser His Gln His Pro
            100                 105                 110

Ser His Pro Gln Leu Phe Ser Ile Val Arg Gln Ala Cys Val Arg Ser
        115                 120                 125

Leu Ser Cys Glu Val Cys Pro Gly Arg Glu Gly Pro Ile Phe Phe Gly
    130                 135                 140

Asp Glu Gln His Gly Phe Val Phe Ser His Thr Phe Ile Lys Asp
145                 150                 155                 160

Ser Leu Ala Arg Gly Phe Gln Arg Trp Tyr Ser Ile Ile Thr Ile Met
                165                 170                 175

Met Asp Arg Ile Tyr Leu Ile Asn Ser Trp Pro Phe Leu Leu Gly Lys
```

```
            180                 185                 190
Val Arg Gly Ile Ile Asp Glu Leu Gln Gly Lys Ala Leu Lys Val Phe
            195                 200                 205

Glu Ala Glu Gln Phe Gly Cys Pro Gln Arg Ala Gln Arg Met Asn Thr
        210                 215                 220

Ala Phe Thr Pro Phe Leu His Gln Arg Asn Gly Asn Ala Ala Arg Ser
225                 230                 235                 240

Leu Thr Ser Leu Thr Ser Asp Asp Asn Leu Trp Ala Cys Leu His Thr
                245                 250                 255

Ser Phe Ala Trp Leu Leu Lys Ala Cys Gly Ser Arg Leu Thr Glu Lys
            260                 265                 270

Leu Leu Glu Gly Ala Pro Thr Glu Asp Thr Leu Val Gln Met Glu Lys
        275                 280                 285

Leu Ala Asp Leu Glu Glu Glu Ser Glu Ser Trp Asp Asn Ser Glu Ala
290                 295                 300

Glu Glu Glu Glu Lys Ala Pro Val Leu Pro Glu Ser Thr Gly Arg
305                 310                 315                 320

Glu Leu Thr Gln Gly Pro Ala Glu Ser Ser Leu Ser Gly Cys Gly
                325                 330                 335

Ser Trp Gln Pro Arg Lys Leu Pro Val Phe Lys Ser Leu Arg His Met
            340                 345                 350

Arg Gln Val Leu Gly Ala Pro Ser Phe Arg Met Leu Ala Trp His Val
        355                 360                 365

Leu Met Gly Asn Gln Val Ile Trp Lys Ser Arg Asp Val Asp Leu Val
370                 375                 380

Gln Ser Ala Phe Glu Val Leu Arg Thr Met Leu Pro Val Gly Cys Val
385                 390                 395                 400

Arg Ile Ile Pro Tyr Ser Ser Gln Tyr Glu Ala Tyr Arg Cys Asn
                405                 410                 415

Phe Leu Gly Leu Ser Pro His Val Gln Ile Pro Pro His Val Leu Ser
            420                 425                 430

Ser Glu Phe Ala Val Ile Val Glu Val His Ala Ala Arg Ser Thr
        435                 440                 445

Leu His Pro Val Gly Cys Glu Asp Asp Gln Ser Leu Ser Lys
450                 455                 460
```

<210> SEQ ID NO 13
<211> LENGTH: 208
<212> TYPE: DNA
<213> ORGANISM: Homo sapiens
<220> FEATURE:
<221> NAME/KEY: miscellaneous
<222> LOCATION: (1)..(208)
<223> OTHER INFORMATION: BHD exon in some embodiments, originally
      identified in a lung cancer sample

<400> SEQUENCE: 13
gttttgtctt cgctctgttt ggaggagagg gtgtgtgtca tcctcttctc ccagtttggc        60
gttcaggagg gtcctctgat gcgctaatag ggtagcaccg tgtcctccag ggagggtgga       120
agaccgcgct tctctccagt tgagagtact gtcagtcgcg tccttgtctc ctggaaagaa       180
tggattggct tgtggattga agtccaag                                          208

<210> SEQ ID NO 14
<211> LENGTH: 2287
<212> TYPE: DNA
<213> ORGANISM: Mus musculus

```
<220> FEATURE:
<221> NAME/KEY: CDS
<222> LOCATION: (325)..(2064)

<400> SEQUENCE: 14
```

| | |
|---|---|
| gcgggtcacg cgctaaggct cagtgcaagg gcctgcggaa cgggctagca cttgcccgag | 60 |
| gggcagaaca gtggcgacag ccccaggaca gttgcgagcg ggttccggcc cagcatccgg | 120 |
| gagacggcgg caagcgcccc agctgggttg gtgttgggcc atagggctga atggaaagcg | 180 |
| cggatgacaa cctcaagtct ttgaattcga atagtgcagc ttgcttacct gactcttccg | 240 |
| gcgggcctcg tacatgttct gctctaggcg ggatggtgca gttgtgatgt gctaagcata | 300 |

```
aggcctcggc cattctccag cacc atg aac gcc ata gtc gcc ctc tgc cac      351
                             Met Asn Ala Ile Val Ala Leu Cys His
                              1               5 ttc tgc gag ctc cat ggc ccc cgc acg ctc ttc tgc acg gaa gtt cta      399
Phe Cys Glu Leu His Gly Pro Arg Thr Leu Phe Cys Thr Glu Val Leu
 10              15                  20                  25 cac gct ccc ctg ccc cag ggg gcc gga agt ggg gac agt cct gac cag      447
His Ala Pro Leu Pro Gln Gly Ala Gly Ser Gly Asp Ser Pro Asp Gln
                 30                  35                  40 gtt gag cag gct gag gag gag gag ggt ggc att cag atg agc agc cgg      495
Val Glu Gln Ala Glu Glu Glu Glu Gly Gly Ile Gln Met Ser Ser Arg
             45                  50                  55 gtc cgt gcc cac agc cca gcc gag ggt gcc agc agt gag tcc agc agc      543
Val Arg Ala His Ser Pro Ala Glu Gly Ala Ser Ser Glu Ser Ser Ser
         60                  65                  70 ccg ggg ccc aag aag tcg gac atg tgt gag ggc tgc cgg tca ctt gcc      591
Pro Gly Pro Lys Lys Ser Asp Met Cys Glu Gly Cys Arg Ser Leu Ala
     75                  80                  85 gta ggg cac cca ggc tat atc agt cat gat aaa gag acc tct att aag      639
Val Gly His Pro Gly Tyr Ile Ser His Asp Lys Glu Thr Ser Ile Lys
 90                  95                 100                 105 tac gtc agt cac cag cac ccc aac cac ccg cag ctc ttc agc atc gtc      687
Tyr Val Ser His Gln His Pro Asn His Pro Gln Leu Phe Ser Ile Val
                110                 115                 120 cgc cag gcc tgt gtc cgg agc ctg agc tgt gag gta tgc cct ggt cgt      735
Arg Gln Ala Cys Val Arg Ser Leu Ser Cys Glu Val Cys Pro Gly Arg
            125                 130                 135 gaa ggc ccc atc ttc ttt ggt gat gag cag cac ggc ttt gtg ttc agc      783
Glu Gly Pro Ile Phe Phe Gly Asp Glu Gln His Gly Phe Val Phe Ser
        140                 145                 150 cac acc ttc ttc atc aaa gac agc ctg gcc aga ggc ttc cag cgc tgg      831
His Thr Phe Phe Ile Lys Asp Ser Leu Ala Arg Gly Phe Gln Arg Trp
    155                 160                 165 tac agc atc atc gcc atc atg atg gat cgg atc tac ctc atc aac tcc      879
Tyr Ser Ile Ile Ala Ile Met Met Asp Arg Ile Tyr Leu Ile Asn Ser
170                 175                 180                 185 tgg ccc ttc ctg ctg ggg agg atc cgc ggc atc atc agt gag ctc cag      927
Trp Pro Phe Leu Leu Gly Arg Ile Arg Gly Ile Ile Ser Glu Leu Gln
                190                 195                 200 gcc aag gcc ttc aag gtg ttt gag gca gag cag ttt gga tgt cca cag      975
Ala Lys Ala Phe Lys Val Phe Glu Ala Glu Gln Phe Gly Cys Pro Gln
            205                 210                 215 cgt gcc cag agg atg aac act gcc ttc acg ccc ttc ctg cac cag agg     1023
Arg Ala Gln Arg Met Asn Thr Ala Phe Thr Pro Phe Leu His Gln Arg
        220                 225                 230 aac ggc aac gct gcc cgc tct ctg acc tcc ttg acc agt gat gac aac     1071
Asn Gly Asn Ala Ala Arg Ser Leu Thr Ser Leu Thr Ser Asp Asp Asn
    235                 240                 245
```

-continued

```
ttg tgg gcg tgt ctg cac act tcc ttt gcc tgg ctc ctg aag gca tgc    1119
Leu Trp Ala Cys Leu His Thr Ser Phe Ala Trp Leu Leu Lys Ala Cys
250                 255                 260                 265 ggt agc agg ctg aca gaa aag ctc tta gag ggc gct ccc aca gag gac    1167
Gly Ser Arg Leu Thr Glu Lys Leu Leu Glu Gly Ala Pro Thr Glu Asp
                270                 275                 280 acc ctg gtc cag atg gag aag ctt gct gac ttg gag gaa gaa tca gaa    1215
Thr Leu Val Gln Met Glu Lys Leu Ala Asp Leu Glu Glu Glu Ser Glu
            285                 290                 295 agt tgg gac aat tct gag gct gag gag gag gag aaa gct cct gtt aca    1263
Ser Trp Asp Asn Ser Glu Ala Glu Glu Glu Glu Lys Ala Pro Val Thr
        300                 305                 310 cca gag ggt gct gaa ggg cga gag ctg acc agt tgc cca aca gag tca    1311
Pro Glu Gly Ala Glu Gly Arg Glu Leu Thr Ser Cys Pro Thr Glu Ser
    315                 320                 325 tcc ttt ctc tca gcc tgt ggg agc tgg cag ccc cca aag ctt acc ggc    1359
Ser Phe Leu Ser Ala Cys Gly Ser Trp Gln Pro Pro Lys Leu Thr Gly
330                 335                 340                 345 ttc aag tct ctt cga cac atg aga cag gtc ttg ggt gct cca tcc ttc    1407
Phe Lys Ser Leu Arg His Met Arg Gln Val Leu Gly Ala Pro Ser Phe
                350                 355                 360 cgt atg ttg gct tgg cat gtc ctc atg ggg aat cag gtg atc tgg aaa    1455
Arg Met Leu Ala Trp His Val Leu Met Gly Asn Gln Val Ile Trp Lys
            365                 370                 375 agc aga gat gtg aac ctg gtc cat tca gcg ttt gaa gtc ctc cgg acc    1503
Ser Arg Asp Val Asn Leu Val His Ser Ala Phe Glu Val Leu Arg Thr
        380                 385                 390 atg ctg cct gtg ggc tgt gtc cgc atc atc cct tac agc agc cag tat    1551
Met Leu Pro Val Gly Cys Val Arg Ile Ile Pro Tyr Ser Ser Gln Tyr
    395                 400                 405 gag gag gcc tat cgc tgc aac ttc ctg ggg ctc agc cct ccc gtg cct    1599
Glu Glu Ala Tyr Arg Cys Asn Phe Leu Gly Leu Ser Pro Pro Val Pro
410                 415                 420                 425 atc cct gcc cat gtt ctg gcc tca gag ttc gta gtt gtc gtg gag gtc    1647
Ile Pro Ala His Val Leu Ala Ser Glu Phe Val Val Val Val Glu Val
                430                 435                 440 cac acg gcc act cgc tca aac ctc cac cct gct ggg tgc gag gat gac    1695
His Thr Ala Thr Arg Ser Asn Leu His Pro Ala Gly Cys Glu Asp Asp
            445                 450                 455 cag tcc ctc agc aag tat gag ttt gtg gtg acc agt ggt agc cct gtg    1743
Gln Ser Leu Ser Lys Tyr Glu Phe Val Val Thr Ser Gly Ser Pro Val
        460                 465                 470 gct gca gac aga gtt ggg ccc act atc ctg aat aag att gaa gca gct    1791
Ala Ala Asp Arg Val Gly Pro Thr Ile Leu Asn Lys Ile Glu Ala Ala
    475                 480                 485 ctg acc aac cag aac ctg tct gtg gat gtg gtg gac caa tgt ctc atc    1839
Leu Thr Asn Gln Asn Leu Ser Val Asp Val Val Asp Gln Cys Leu Ile
490                 495                 500                 505 tgc ctc aag gag gaa tgg atg aac aaa gtg aaa gtc ctg ttt aaa ttc    1887
Cys Leu Lys Glu Glu Trp Met Asn Lys Val Lys Val Leu Phe Lys Phe
                510                 515                 520 acc aag gta gac agt cgc ccc aag gag gac aca cag aag ctc cta agc    1935
Thr Lys Val Asp Ser Arg Pro Lys Glu Asp Thr Gln Lys Leu Leu Ser
            525                 530                 535 gtc cta ggc gca tca gag gag gac aac gtc aaa ctg ctg aag ttc tgg    1983
Val Leu Gly Ala Ser Glu Glu Asp Asn Val Lys Leu Leu Lys Phe Trp
        540                 545                 550 atg acg gga ctg agc aaa acc tac aag tcc cat ctc atg tcc acc gtc    2031
Met Thr Gly Leu Ser Lys Thr Tyr Lys Ser His Leu Met Ser Thr Val
```

```
                555              560              565
cga agc ccc aca gct aca gag tca cgg agc tga ctccgagaac tccttctgga    2084
Arg Ser Pro Thr Ala Thr Glu Ser Arg Ser
570                 575 aggtggtgta cagaccagct ctgtgggaaa aactgccctt gggtttctga cttctggggt    2144
gaggccctgt ttatggccta gggttcaccc tccttgtaag actctatcag cccatgttga    2204
aatgtagggg acacagagac agtggtccct ttgcatcaaa ctgcgctgtc aggacctggc    2264
gagatgtgtt ctgtgccccg tga                                            2287

<210> SEQ ID NO 15
<211> LENGTH: 579
<212> TYPE: PRT
<213> ORGANISM: Mus musculus

<400> SEQUENCE: 15

Met Asn Ala Ile Val Ala Leu Cys His Phe Cys Glu Leu His Gly Pro
1               5                   10                  15

Arg Thr Leu Phe Cys Thr Glu Val Leu His Ala Pro Leu Pro Gln Gly
            20                  25                  30

Ala Gly Ser Gly Asp Ser Pro Asp Gln Val Glu Gln Ala Glu Glu
        35                  40                  45

Glu Gly Gly Ile Gln Met Ser Ser Arg Val Arg Ala His Ser Pro Ala
    50                  55                  60

Glu Gly Ala Ser Ser Glu Ser Ser Pro Gly Pro Lys Lys Ser Asp
65                  70                  75                  80

Met Cys Glu Gly Cys Arg Ser Leu Ala Val Gly His Pro Gly Tyr Ile
                85                  90                  95

Ser His Asp Lys Glu Thr Ser Ile Lys Tyr Val Ser Gln His Pro
            100                 105                 110

Asn His Pro Gln Leu Phe Ser Ile Val Arg Gln Ala Cys Val Arg Ser
        115                 120                 125

Leu Ser Cys Glu Val Cys Pro Gly Arg Glu Gly Pro Ile Phe Phe Gly
    130                 135                 140

Asp Glu Gln His Gly Phe Val Phe Ser His Thr Phe Ile Lys Asp
145                 150                 155                 160

Ser Leu Ala Arg Gly Phe Gln Arg Trp Tyr Ser Ile Ile Ala Ile Met
                165                 170                 175

Met Asp Arg Ile Tyr Leu Ile Asn Ser Trp Pro Phe Leu Leu Gly Arg
            180                 185                 190

Ile Arg Gly Ile Ile Ser Glu Leu Gln Ala Lys Ala Phe Lys Val Phe
        195                 200                 205

Glu Ala Glu Gln Phe Gly Cys Pro Gln Arg Ala Gln Arg Met Asn Thr
    210                 215                 220

Ala Phe Thr Pro Phe Leu His Gln Arg Asn Gly Asn Ala Ala Arg Ser
225                 230                 235                 240

Leu Thr Ser Leu Thr Ser Asp Asp Asn Leu Trp Ala Cys Leu His Thr
                245                 250                 255

Ser Phe Ala Trp Leu Leu Lys Ala Cys Gly Ser Arg Leu Thr Glu Lys
            260                 265                 270

Leu Leu Glu Gly Ala Pro Thr Glu Asp Thr Leu Val Gln Met Glu Lys
        275                 280                 285

Leu Ala Asp Leu Glu Glu Glu Ser Glu Ser Trp Asp Asn Ser Glu Ala
    290                 295                 300
```

Glu Glu Glu Lys Ala Pro Val Thr Pro Glu Gly Ala Glu Gly Arg
305                 310                 315                 320

Glu Leu Thr Ser Cys Pro Thr Glu Ser Ser Phe Leu Ser Ala Cys Gly
            325                 330                 335

Ser Trp Gln Pro Pro Lys Leu Thr Gly Phe Lys Ser Leu Arg His Met
            340                 345                 350

Arg Gln Val Leu Gly Ala Pro Ser Phe Arg Met Leu Ala Trp His Val
            355                 360                 365

Leu Met Gly Asn Gln Val Ile Trp Lys Ser Arg Asp Val Asn Leu Val
    370                 375                 380

His Ser Ala Phe Glu Val Leu Arg Thr Met Leu Pro Val Gly Cys Val
385                 390                 395                 400

Arg Ile Ile Pro Tyr Ser Ser Gln Tyr Glu Glu Ala Tyr Arg Cys Asn
                405                 410                 415

Phe Leu Gly Leu Ser Pro Pro Val Pro Ile Pro Ala His Val Leu Ala
            420                 425                 430

Ser Glu Phe Val Val Val Glu Val His Thr Ala Thr Arg Ser Asn
        435                 440                 445

Leu His Pro Ala Gly Cys Glu Asp Asp Gln Ser Leu Ser Lys Tyr Glu
    450                 455                 460

Phe Val Val Thr Ser Gly Ser Pro Val Ala Ala Asp Arg Val Gly Pro
465                 470                 475                 480

Thr Ile Leu Asn Lys Ile Glu Ala Ala Leu Thr Asn Gln Asn Leu Ser
                485                 490                 495

Val Asp Val Asp Gln Cys Leu Ile Cys Leu Lys Glu Glu Trp Met
        500                 505                 510

Asn Lys Val Lys Val Leu Phe Lys Phe Thr Lys Val Asp Ser Arg Pro
    515                 520                 525

Lys Glu Asp Thr Gln Lys Leu Leu Ser Val Leu Gly Ala Ser Glu Glu
            530                 535                 540

Asp Asn Val Lys Leu Leu Lys Phe Trp Met Thr Gly Leu Ser Lys Thr
545                 550                 555                 560

Tyr Lys Ser His Leu Met Ser Thr Val Arg Ser Pro Thr Ala Thr Glu
                565                 570                 575

Ser Arg Ser

<210> SEQ ID NO 16
<211> LENGTH: 19
<212> TYPE: DNA
<213> ORGANISM: Artificial sequence
<220> FEATURE:
<223> OTHER INFORMATION: primer

<400> SEQUENCE: 16
ggactctggc cctaaaccc                                                19

<210> SEQ ID NO 17
<211> LENGTH: 19
<212> TYPE: DNA
<213> ORGANISM: Artificial sequence
<220> FEATURE:
<223> OTHER INFORMATION: primer

<400> SEQUENCE: 17
gtacggctca gggagtcac                                                19

<210> SEQ ID NO 18

```
<211> LENGTH: 20
<212> TYPE: DNA
<213> ORGANISM: Artificial sequence
<220> FEATURE:
<223> OTHER INFORMATION: primer

<400> SEQUENCE: 18
gacagcaagc ctgggccaag                                              20

<210> SEQ ID NO 19
<211> LENGTH: 22
<212> TYPE: DNA
<213> ORGANISM: Artificial sequence
<220> FEATURE:
<223> OTHER INFORMATION: primer

<400> SEQUENCE: 19
catgctacga aggcctctaa tc                                           22

<210> SEQ ID NO 20
<211> LENGTH: 20
<212> TYPE: DNA
<213> ORGANISM: Artificial sequence
<220> FEATURE:
<223> OTHER INFORMATION: primer

<400> SEQUENCE: 20
aaggacgatg tgcatggtgg                                              20

<210> SEQ ID NO 21
<211> LENGTH: 19
<212> TYPE: DNA
<213> ORGANISM: Artificial sequence
<220> FEATURE:
<223> OTHER INFORMATION: primer

<400> SEQUENCE: 21
cactgccagc ccagctaag                                               19

<210> SEQ ID NO 22
<211> LENGTH: 19
<212> TYPE: DNA
<213> ORGANISM: Artificial sequence
<220> FEATURE:
<223> OTHER INFORMATION: primer

<400> SEQUENCE: 22
cactgctctc aggtcctcc                                               19

<210> SEQ ID NO 23
<211> LENGTH: 23
<212> TYPE: DNA
<213> ORGANISM: Artificial sequence
<220> FEATURE:
<223> OTHER INFORMATION: primer

<400> SEQUENCE: 23
ggaggtttca tggagtcaat agg                                          23

<210> SEQ ID NO 24
<211> LENGTH: 19
<212> TYPE: DNA
<213> ORGANISM: Artificial sequence
<220> FEATURE:
<223> OTHER INFORMATION: primer

<400> SEQUENCE: 24
```
agtgcctgcc tccctgtgc                                        19

<210> SEQ ID NO 25
<211> LENGTH: 23
<212> TYPE: DNA
<213> ORGANISM: Artificial sequence
<220> FEATURE:
<223> OTHER INFORMATION: primer

<400> SEQUENCE: 25
acctaagaga gtttgtcgcc ctg                                   23

<210> SEQ ID NO 26
<211> LENGTH: 20
<212> TYPE: DNA
<213> ORGANISM: Artificial sequence
<220> FEATURE:
<223> OTHER INFORMATION: primer

<400> SEQUENCE: 26
tcagcacaga gcggctcatg                                       20

<210> SEQ ID NO 27
<211> LENGTH: 24
<212> TYPE: DNA
<213> ORGANISM: Artificial sequence
<220> FEATURE:
<223> OTHER INFORMATION: primer

<400> SEQUENCE: 27
gaagaggctt tgatttggtg tcac                                  24

<210> SEQ ID NO 28
<211> LENGTH: 24
<212> TYPE: DNA
<213> ORGANISM: Artificial sequence
<220> FEATURE:
<223> OTHER INFORMATION: primer

<400> SEQUENCE: 28
ccaatgtatc gtgactgctc tatc                                  24

<210> SEQ ID NO 29
<211> LENGTH: 18
<212> TYPE: DNA
<213> ORGANISM: Artificial sequence
<220> FEATURE:
<223> OTHER INFORMATION: primer

<400> SEQUENCE: 29
ggtccgagct gctggcag                                         18

<210> SEQ ID NO 30
<211> LENGTH: 19
<212> TYPE: DNA
<213> ORGANISM: Artificial sequence
<220> FEATURE:
<223> OTHER INFORMATION: primer

<400> SEQUENCE: 30
gccccagatc aggaacctg                                        19

<210> SEQ ID NO 31
<211> LENGTH: 21
<212> TYPE: DNA

```
<213> ORGANISM: Artificial sequence
<220> FEATURE:
<223> OTHER INFORMATION: primer

<400> SEQUENCE: 31
ctgggtgagc gtcaggtttg c                                              21

<210> SEQ ID NO 32
<211> LENGTH: 20
<212> TYPE: DNA
<213> ORGANISM: Artificial sequence
<220> FEATURE:
<223> OTHER INFORMATION: primer

<400> SEQUENCE: 32
ccatgactgg ctctcctcct                                                20

<210> SEQ ID NO 33
<211> LENGTH: 23
<212> TYPE: DNA
<213> ORGANISM: Artificial sequence
<220> FEATURE:
<223> OTHER INFORMATION: primer

<400> SEQUENCE: 33
gtatcttggg ctgaagtcac agg                                            23

<210> SEQ ID NO 34
<211> LENGTH: 18
<212> TYPE: DNA
<213> ORGANISM: Artificial sequence
<220> FEATURE:
<223> OTHER INFORMATION: primer

<400> SEQUENCE: 34
gcaccaggcc aatactgc                                                  18

<210> SEQ ID NO 35
<211> LENGTH: 21
<212> TYPE: DNA
<213> ORGANISM: Artificial sequence
<220> FEATURE:
<223> OTHER INFORMATION: primer

<400> SEQUENCE: 35
gtctttctcc tgagccctgt c                                              21

<210> SEQ ID NO 36
<211> LENGTH: 20
<212> TYPE: DNA
<213> ORGANISM: Artificial sequence
<220> FEATURE:
<223> OTHER INFORMATION: primer

<400> SEQUENCE: 36
ggttccactt tgggcctgag                                                20

<210> SEQ ID NO 37
<211> LENGTH: 21
<212> TYPE: DNA
<213> ORGANISM: Artificial sequence
<220> FEATURE:
<223> OTHER INFORMATION: primer

<400> SEQUENCE: 37
ggtagtagag catggatggc c                                              21
```

```
<210> SEQ ID NO 38
<211> LENGTH: 21
<212> TYPE: DNA
<213> ORGANISM: Artificial sequence
<220> FEATURE:
<223> OTHER INFORMATION: primer

<400> SEQUENCE: 38
cagctccagg ttttctccag g                                              21

<210> SEQ ID NO 39
<211> LENGTH: 18
<212> TYPE: DNA
<213> ORGANISM: Artificial sequence
<220> FEATURE:
<223> OTHER INFORMATION: primer

<400> SEQUENCE: 39
cacggtgggc tagcgcag                                                  18

<210> SEQ ID NO 40
<211> LENGTH: 23
<212> TYPE: DNA
<213> ORGANISM: Artificial sequence
<220> FEATURE:
<223> OTHER INFORMATION: primer

<400> SEQUENCE: 40
cctcgggagc agacatgtta ttg                                            23

<210> SEQ ID NO 41
<211> LENGTH: 19
<212> TYPE: DNA
<213> ORGANISM: Artificial sequence
<220> FEATURE:
<223> OTHER INFORMATION: primer

<400> SEQUENCE: 41
accagggctc gagggattg                                                 19

<210> SEQ ID NO 42
<211> LENGTH: 3660
<212> TYPE: DNA
<213> ORGANISM: Homo sapiens
<220> FEATURE:
<221> NAME/KEY: misc_feature
<222> LOCATION: (1087)..(1087)
<223> OTHER INFORMATION: m is a or c
<220> FEATURE:
<221> NAME/KEY: misc_feature
<222> LOCATION: (1088)..(1088)
<223> OTHER INFORMATION: n is g or no nucleotide
<220> FEATURE:
<221> NAME/KEY: misc_feature
<222> LOCATION: (1389)..(1416)
<223> OTHER INFORMATION: These nucleotides may be all present or all
      absent
<220> FEATURE:
<221> NAME/KEY: misc_feature
<222> LOCATION: (1768)..(1769)
<223> OTHER INFORMATION: n is c or no nucleotide
<220> FEATURE:
<221> NAME/KEY: misc_feature
<222> LOCATION: (1873)..(1873)
<223> OTHER INFORMATION: s is g or c

<400> SEQUENCE: 42
ggtcgctcct ggttctgcca gctcccctga gagcctgaac ccgggcttga gagcctcgcc    60
```

```
acccegggtg acatccctgc cgtgggcttg ggggctctgg gtgtgattcc gccggtccgg    120
gtcccgcagc gaccacctac ccagcgcagt caggggtggg gctgggaccc agagcgggac    180
cccggctgcc gagtccaggt gtcccgcggg cctcgatttg gggagcagaa aacgccaggt    240
cttcaagggt gtctgccacc accatgcctg acccatttgg cagcagcctc gtgtgtggtg    300
gtctggtgtg gacggtggaa gcgtgattct gctgagtgtc agtgtgacca ctcgtgctca    360
gccgtatctc agcaggagga caggtgccgg agcagctcgt gcagctaagc agccaactgc    420
agaaacgtca ggcctgttgc agtctccaag gcaccatgaa tgccatcgtg gctctctgcc    480
acttctgcga gctccacggc ccccgcactc tcttctgcac ggaggtgctg cacgccccac    540
ttcctcaagg ggatgggaat gaggacagtc ctggccaggg tgagcaggcg aagaagagg    600 aaggtggcat tcagatgaac agtcggatgc gtgcgcacag cccgcagag ggggccagcg    660 tcgagtccag cagcccgggg cccaaaaagt cggacatgtg cgagggctgc cggtcacttg    720
ctgcagggca cccgggatat atcagccatg ataaagagac ctccattaaa tacgtcagcc    780
accagcaccc cagccacccc cagctcttca gcattgtccg ccaggcctgt gtccggagcc    840
tgagctgtga ggtctgccct ggccgtgaag gccccatctt cttcggagat gagcagcacg    900
gctttgtgtt cagccacacc ttcttcatca aggacagcct ggccaggggc ttccagcgct    960
ggtacagcat catcaccatc atgatggacc ggatctacct catcaactcc tggcccttcc   1020
tgctggggaa ggtccgggga tcatcgatg agctccaggg caaggcgctc aaggtgtttg   1080
aggcagmnca gtttggatgc ccacagcgtg ctcagaggat gaacacagcc ttcacgccat   1140
tcctacacca gaggaacggc aacgccgccc gctcgctgac atcgctgaca agtgatgaca   1200
acctgtgggc gtgcctgcac acctcctttg cctggctcct gaaggcgtgt ggcagccggc   1260
tgaccgagaa gctcctggaa ggtgctccga ccgaggatac cttggtccag atggagaagc   1320
tcgctgattt agaagaggaa tcagaaagct gggacaactc tgaggctgaa gaggaggaga   1380
aagcccctgt gttgccagag agtacagaaa gcccctgtgt tgccagagag tacagaaggg   1440
cgggagctga cccagggccc ggcagagtcc tcctctctct caggctgtgg gagctggcag   1500
ccccggaagc tgccagtctt caagtccctc cggcacatga ggcaggtcct gggtgccect   1560 tctttccgca tgctggcctg gcacgttctc atggggaacc aggtgatctg gaaaagcaga   1620
gacgtggacc tcgtccagtc agcttttgaa gtacttcgga ccatgcttcc cgtgggctgc   1680
gtccgcatca tcccatacag cagccagtac gaggaggcct atcggtgcaa cttcctgggg   1740
ctcagcccgc acgtgcagat ccccccnna cgtgctctcc tcagagtttg ctgtcatcgt   1800
ggaggtccac gcagccgcac gttccaccct ccaccctgtg gggtgtgagg atgaccagtc   1860
tctcagcaag tasgagtttg tggtgaccag tgggagccct gtagctgcag accgagtggg   1920
ccccaccatc ctgaataaga ttgaagcggc tctgaccaac cagaacctgt ctgtggatgt   1980
ggtggaccag tgcctcgtct gcctcaagga ggagtggatg aacaaagtga aggtgctttt   2040
taagttcacc aaggtggaca gtcgacccaa agaggacaca cagaagctgc tgagcatcct   2100
gggtgcgtcc gaggaggaca atgtcaagct gctgaagttc tggatgactg gcctgagcaa   2160
gacctacaag tcacacctca gtccacggt ccgcagcccc acagcctcgg agtctcggaa   2220
ctgacccgtc acacacacct gcctaaagac agggatggct gtccacagga tcctccagcc   2280
ccgtgagagg gactgtccct tgagtttctc aactgctgga aggagctgtg tcccagcaag   2340
gaagggaaac catcagggct gggctcggcc ctgtcaggtt tggggcctgt gtgcttccca   2400
```

-continued

```
gactctccct ccagccgttg gaatcgctga agatggcaat gaaaggcgga gggatgatgg    2460
gctctctctg tgttcaaact ccttggagag acgactagga ggacagcttg cctcccaggc    2520
cccttgtgga cttagactca aaacccgcag gagaaacagg tccgactcag tatgcagtcg    2580
caataacatg tctgctcccg aggttaacat tcaagcgttt ctactttgaa attcagcaag    2640
agtttctggg ccttatgttt gagggtacct tttgctgcag ttgtgaatat tcagtacatt    2700
gccagctctt ggtcactgag tgattgagtt agggctccgc aagagacttt ggggagtgaa    2760
gtggatctct tcctcatctt ctggtcctct gaaatgtgtg ttctgaagcc atgggctcg     2820 tcttctgggg tgttcccctg caggtgctgg tgaaggtaac ctggggctta atgatggagt    2880
ccctgatcat ttttgcacaa gacaggttgc tgaggggtcg gcaagcatct gacttgccca    2940
atcccctgga tatggtgagc cccgccatgc ttttattctg tatcgctttt gtctttattg    3000
ctgctttcaa catttacgtt tggttacagt taactatttt cggagtgtgg tgattgaaga    3060
caatttcatc atcccactgt acttttttttt ttgagaggga gtttcactct tgttgcccag    3120
gctggagtgc aatggcacga tcttggctca ctgcaacctc tgcctcctgg gttcaagcaa    3180
ttctcctgcc tcagcctcca gagtagctgg aactacaggt gcccgccact atgcccagct    3240 aattttttgta ttttttagta gagacggggt ttcaccgtgt tggccgggct ggtctcaaac   3300
tcctgacctc aggtgatcca cccacctcag cctcccaaag tgctgggatt acaagcgtga    3360
gccactgtgc ctggcccttt ttttttttttt tttttttttt tttaaagaga tggcatcttg    3420
ctatgtcgtc caggctggtc ttgaactcct gagttcaagc agtcctcctg cttcaacata    3480
cagctacagg tacccccccac tatacatttt taataaggat tcatggctca gagggatttt    3540
ctgatggttt tgctgatttg tttctagttt ttttgtgttt atatttaaca tgaagaccaa    3600
gtttatataa ctaggtatct gtataatgca acaacattgg aacacaataa agatgtattt    3660
```